United States Patent [19]
Kinders et al.

[11] Patent Number: 6,017,703
[45] Date of Patent: Jan. 25, 2000

[54] METHODS AND COMPOSITIONS FOR SCREENING FOR OR MODULATING A TUMOR ASSOCIATED ANTIGEN

[75] Inventors: Robert J. Kinders, Woodinville; David L. Enfield, Bothell; G. Michael Hass, Issaquah, all of Wash.

[73] Assignee: Bard Diagnostic Sciences, Inc., Redmond, Wash.

[21] Appl. No.: 08/824,692

[22] Filed: Apr. 8, 1997

Related U.S. Application Data

[60] Provisional application No. 60/015,083, Apr. 9, 1996, and provisional application No. 60/038,614, Mar. 6, 1997.

[51] Int. Cl.$^7$ .............................. G01N 33/574; C12Q 1/68
[52] U.S. Cl. ................................ 435/6; 435/7.23; 436/63; 436/64; 436/813
[58] Field of Search ......................... 435/6, 7.23; 436/63, 436/64, 813

[56] References Cited

FOREIGN PATENT DOCUMENTS 222 611 A2  5/1987  European Pat. Off. .

OTHER PUBLICATIONS

Bangma et al., "Prostate specific antigen: its clinical use and application in screening for prostate cancer," *Scand. J. Clin. Lab. Invest. Suppl.* 55(Suppl. 221): 35–44, 1995.

Bates, "Clinical applications of serum tumor markers," *Annals of Internal Medicine* 115(8): 623–638, 1991.

Juhl, "New Approaches in Gastric Cancer Research: I. Monoclonal Antibodies in Diagnosis and Therapy," *Hepato–Gastroenterology* 36(1): 27–32, 1989.

McCarley and Weiner, "Diagnostic and Therapeutic Utility of Monoclonal Antibodies in Urologic Oncology," *Seminars in Surgical Oncology* 5(4): 293–301, 1989.

Ollert et al., "Classical Complement Pathway Activation on Nucleated Cells," *The Journal of Immunology* 155: 4955–4962, 1995.

Pangburn and Muller–Eberhard, "The Alternative Pathway of Complement," *Springer Seminars in Immunopathology* 7(2/3): 163–192, 1984.

Pangburn et al., "Formation Of The Initial C3 Convertase Of The Alternative Complement Pathway. Acquisition of C3b–like Activities by Spontaneous Hydrolysis of the Putative Thioester in Native C3," *J. Exp. Med.* 154: 856–867, 1981.

Reid, *Molecular Immunology*, Second Edition, Oxford University Press, New York, 1996, Chapter 8, "The Complement System," pp. 326–381.

Ripoche et al., "The complete amino acid sequence of human complement factor H," *Biochem. J.* 249: 593–602, 1988.

Van Den Dobbelsteen et al., "Regulation of C3 and factor H synthesis of human glomerular mesangial cells by IL–1 and interferon gamma," *Clin. Exp. Immunol.* 95:173–180, 1994.

Gasque, et al., *J. Immunol.*, vol. 149, No. 4, pp. 1381–1387, 1992, Abstract only.

*Primary Examiner*—Toni R. Scheiner
*Attorney, Agent, or Firm*—Seed and Berry LLP

[57] ABSTRACT

Methods of screening for or treating cancer are disclosed. The screening methods are based on the detection of an antigen, or a nucleic acid molecule encoding the antigen, found by the present invention to be associated with the presence of cancer. Preferred embodiments of the methods include detection of the antigen based on immunological properties, physical properties, enzymatic properties and combinations thereof, or detection of a nucleic acid molecule encoding the antigen based on nucleic acid amplification.

9 Claims, 15 Drawing Sheets

```
                            420        430        440        450        460        470
                             |          |          |          |          |          |
huCFH 4.4kb cDNAseq   ACATGTAATGAGGGGTATCAATTGCTAGGTGAGATTAATTACCGTGAATGTGACACAGA
pRBB9FH410#2.1        ACATGTAATGAGGGGTATCAATTGCTAGGTGAGATTAATTACCGTGAATGTGACACAGA 480        490        500        510        520        530
                             |          |          |          |          |          |
huCFH 4.4kb cDNAseq   TGGATGGACCAATGATATTCCTATATGTGAAGTTGTGAAGTGTTTACCAGTGACAGCAC
pRBB9FH410#2.1        TGGATGGACCAATGATATTCCTATATGTGAAGTTGTGAAGTGTTTACCAGTGACAGCAC 540        550        560        570        580        590
                             |          |          |          |          |          |
huCFH 4.4kb cDNAseq   CAGAGAATGGAAAAATTGTCAGTAGTGCAATGGAACCAGATCGGGAATACCATTTTGGA
pRBB9FH410#2.1        CAGAGAATGGAAAAATTGTCAGTAGTGCAATGGAACCAGATCGGGAATACCATTTTGGA 600        610        620        630        640
                             |          |          |          |          |
huCFH 4.4kb cDNAseq   CAAGCAGTACGGTTTGTATGTAACTCAGGCTACAAGATTGAAGGAGATGAAGAAATGCA
pRBB9FH410#2.1        CAAGCAGTACGGTTTGTATGTAACTCAGGCTACAAGATTGAAGGAGATGAAGAAATGCA 650        660        670        680        690        700
                        |          |          |          |          |          |
huCFH 4.4kb cDNAseq   TTGTTCAGACGATGGTTTTTGGAGTAAAGAGAAACCAAAGTGTGTGGAAATTTCATGCA
pRBB9FH410#2.1        TTGTTCAGACGATGGTTTTTGGGGTAAAGAGAAACCAAAGTGTGTGGAAATTTCATGCA 710        720        730        740        750        760
                        |          |          |          |          |          |
huCFH 4.4kb cDNAseq   AATCCCCAGATGTTATAAATGGATCTCCTATATCTCAGAAGATTATTTATAAGGAGAAT
pRBB9FH410#2.1        AATCCCCAGATGTTATAAATGGATCTCCTATATCTCAGAAGATTATTTATAAGGAGAAT 770        780        790        800        810        820
                        |          |          |          |          |          |
huCFH 4.4kb cDNAseq   GAACGATTTCAATATAAATGTAACATGGGTTATGAATACAGTGAAAGAGGAGATGCTGT
pRBB9FH410#2.1        GAACGATTTCAATATAAATGTAACATGGGTTATGAATACAGTGAAAGAGGAGATGCTGT 830        840        850        860        870        880
                        |          |          |          |          |          |
huCFH 4.4kb cDNAseq   ATGCACTGAATCTGGATGGCGTCCGTTGCCTTCATGTGAAGAAAAATCATGTGATAATC
pRBB9FH410#2.1        ATGCACTGAATCTGGATGGCGTCCGTTGCCTTCATGTGAAGAAAAATCATGTGATAATC 890        900        910        920        930        940
                        |          |          |          |          |          |
huCFH 4.4kb cDNAseq   CTTATATTCCAAATGGTGACTACTCACCTTTAAGGATTAAACACAGAACTGGAGATGAA
pRBB9FH410#2.1        CTTATATTCCAAATGGTGACTACTCACCTTTAAGGATTAAACACAGAACTGGAGATGAA 950        960        970        980        990       1000
                        |          |          |          |          |          |
huCFH 4.4kb cDNAseq   ATCACGTACCAGTGTAGAAATGGTTTTTATCCTGCAACCCGGGGAAATACAGCCAAATG
pRBB9FH410#2.1        ATCACGTACCAGTGTAGAAATGGTTTTTATCCTGCAACCCGGGGAAATAC 1010       1020       1030       1040       1050       1060
                        |          |          |          |          |          |
huCFH 4.4kb cDNAseq   CACAAGTACTGGCTGGATACCTGCTCCGAGATGTACCTTGAAACCTTGTGATTATCCAG
pRBB9FH410#2.1
```

*Fig. 6A*

```
              130       140       150       160       170       180
               |         |         |         |         |         |
CFH-RF3        FTLTGGNVFEYGVKAVYTCNEGYQLLGEINYRECDTDGWTNDIPICEVVKCLPVTAPENG
pRBB9FH410#2,1-RF1              TCNEGYQLLGEINYRECDTDGWTNDIPICEVVKCLPVTAPENG 190       200       210       220       230       240
               |         |         |         |         |         |
CFH-RF3        KIVSSAMEPDREYHFGQAVRFVCNSGYKIEGDEEMHCSDDGFWSKEKPKCVEISCKSPDV
pRBB9FH410#2,1-RF1 KIVSSAMEPDREYHFGQAVRFVCNSGYKIEGDEEMHCSDDGFWGKEKPKCVEISCKSPDV 250       260       270       280       290       300
               |         |         |         |         |         |
CFH-RF3        INGSPISQKIIYKENERFQYKCNMGYEYSERGDAVCTESGWRPLPSCEEKSCDNPYIPNG
pRBB9FH410#2,1-RF1 INGSPISQKIIYKENERFQYKCNMGYEYSERGDAVCTESGWRPLPSCEEKSCDNPYIPNG 310       320       330       340       350       360
               |         |         |         |         |         |
CFH-RF3        DYSPLRIKHRTGDEITYQCRNGFYPATRGNTAKCTSTGWIPAPRCTLKPCDYPDIKHGGL
pRBB9FH410#2,1-RF1 DYSPLRIKHRTGDEITYQCRNGFYPATRGNTAKCTSTGWIPAPRCTLKPCDYP
```

*Fig. 6B*

```
                            2900      2910      2920      2930      2940      2950
                             |         |         |         |         |         |
huCFH 4.4kb cDNAseq    CATGGTGTTGTAGCTCACATGTCAGACAGTTATCAGTATGGAGAAGAAGTTACGTACAA
pRBS3FH2910#2.1                              GTCAGACAGTTATCAGTATGGAGAAGAAGTTACGTACAA
pRBS3FH2910#3.1                              GTCAGACAGTTATCAGTATGGAGAAGAAGTTACGTACAA
pRBS3FH2910#4.1

2960      2970      2980      2990      3000
                          |         |         |         |         |
huCFH 4.4kb cDNAseq    ATGTTTTGAAGGTTTTGGAATTGATGGGCCTGCAATTGCAAAATGCTTAGGAGAAAAAT
pRBS3FH2910#2.1        ATGTTTTGAAGGTTTTGGAATTGATGGGCCTGCAATTGCAAAATGCTTAGGAGAAAAAT
pRBS3FH2910#3.1        ATGTTTTGAAGGTTTTGGAATTGATGGGCCTGCAATTGCAAAATGCTTAGGAGAAAAAT
pRBS3FH2910#4.1

3010      3020      3030      3040      3050      3060
                   |         |         |         |         |         |
huCFH 4.4kb cDNAseq    GGTCTCACCCTCCATCATGCATAAAAACAGATTGTCTCAGTTTACCTAGCTTTGAAAAT
pRBS3FH2910#2.1        GGTCTCACCCTCCATCATGCATAAAAACAGATTGTCTCAGTTTACCTAGCTTTGAAAAT
pRBS3FH2910#3.1        GGTCTCACCCTCCATCATGCATAAAAACAGATTGTCCCAGTTTACCTAGCTTTGAAAAT
pRBS3FH2910#4.1                                             GTTTGCCTAGCTTTGAAAAT 3070      3080      3090      3100      3110      3120
                          |         |         |         |         |         |
huCFH 4.4kb cDNAseq    GCCATACCCATGGGAGAGAAGAAGGATGTGTATAAGGCGGGTGAGCAAGTGACTTACAC
pRBS3FH2910#2.1        GCCATACCCATGGGAGAGAAGAAGGATTTGTATAAGGCGGGTGAGCAAGTGACTTACAC
pRBS3FH2910#3.1        GCCATACCCATGGGAGAGAAGAAGGTTTTGTATAAGGCGGGTGAGCAAGTGACTTACAC
pRBS3FH2910#4.1        GCCATACCCATGGGAGAGAAGAAGGATTTGTATAAGGCGGGTGAGCCAGTGACTTACAC 3130      3140      3150      3160      3170      3180
                   |         |         |         |         |         |
huCFH 4.4kb cDNAseq    TTGTGCAACATATTACAAAATGGATGGAGCCAGTAATGTAACATGCATTAATAGCAGAT
pRBS3FH2910#2.1        TTGTGCAACATATTACAAAATGGATGGAGCCAGTAATGTAACATGCATTAATAGCAGAT
pRBS3FH2910#3.1        TTGTGCAACATATTGCCAAATGGATGGAGCCAGTAATGTAACATGCATTAATAGCAGAT
pRBS3FH2910#4.1        TTGTGCAACATATTACAAAATGGATGGAGCCAGTAATGTAACATGCATTAATAGCAGAT 3190      3200      3210      3220      3230      3240
                          |         |         |         |         |         |
huCFH 4.4kb cDNAseq    GGACAGGAAGGCCAACATGCAGAGACACCTCCTGTGTGAATCCGCCCACAGTACAAAAT
pRBS3FH2910#2.1        GGACAGGAAGGCCAACATGCAGAGACACCTCCTGTGTGAATCCGCCCACAGTACAAAAT
pRBS3FH2910#3.1        GGACAGGAAGGCCAACATGCAGAGACACCTCCTGTGTGAATCCGCCCACAGTACAAAAT
pRBS3FH2910#4.1        GGACAGGAAGGCCAACATGCAGAGACACCTCCTGTGTGAATCCGCCCACAGTACAAAAT 3250      3260      3270      3280      3290      3300
                          |         |         |         |         |         |
huCFH 4.4kb cDNAseq    GCTTATATAGTGTCGAGACAGATGAGTAAATATCCATCTGGTGAGAGAGTACGTTATCA
pRBS3FH2910#2.1        GCTTATATAGTGTCGAGACAGATGAGTAAATATCCATCTGGTGAGAGAGTACGTTATCA
pRBS3FH2910#3.1        GCTTATATAGTGTCGAGACAGATGAGTAAATATCCATCTGGTGAGAGAGTACGTTATCA
pRBS3FH2910#4.1        GCTTATATAGTGTCGAGACAGATGAGTAAATATCCATCTGGTGAGAGAGTACGTTATCA 3310      3320      3330      3340      3350      3360
                          |         |         |         |         |         |
huCFH 4.4kb cDNAseq    ATGTAGGAGCCCTTATGAAATGTTTGGGGATGAAGAAGTGATGTGTTTAAATGGAAACT
pRBS3FH2910#2.1        ATGTAGGAGCCCTTATGAAATGTTTGGGGATGAAGAAGTGATGTGTTTAAATGGAAACT
pRBS3FH2910#3.1        ATGTAGGAGCCCTTATGAAATGTTTGGGGATGAAGAAGTGATGTGTTTAAATGGAAACT
pRBS3FH2910#4.1        ATGTAGGAGCCCTTATGAAATGTTTGGGGATGAAGAAGTGATGTGTTTAAATGGAAACT
```

*Fig. 7A-1*

```
                         3370      3380      3390      3400      3410      3420
                           |         |         |         |         |         |
huCFH 4.4kb cDNAseq  GGACGGAACCACCTCAATGCAAAGATTCTACAGGAAAATGTGGGCCCCCTCCACCTATT
pRBS3FH2910#2.1      GGACGGAACCACCTCAATGCAAAGATTCTACAGGAAAATGTGGGCCCCCTCCACCTATT
pRBS3FH2910#3.1      GGACGGAACCACCTCAATGCAAAGATTCTACAGGAAAATGTGGGCCCCCTCCACCTATT
pRBS3FH2910#4.1      GGACGGAACCACCTCAATGCAAAGATTCTACAGGAAAATGTGGGCCCCCTCCACCTATT 3430      3440      3450      3460      3470      3480
                           |         |         |         |         |         |
huCFH 4.4kb cDNAseq  GACAATGGGGACATTACTTCATTCCCGTTGTCAGTATATGCTCCAGCTTCATCAGTTGA
pRBS3FH2910#2.1      GACAATGGGGACATTACTTCA
pRBS3FH2910#3.1      GACAATGGGGACATTACTTCATTCCCGTTGTCAGTATATGCTCCAGCTTCATCAGTTGA
pRBS3FH2910#4.1      GACAATGGGGACATTACTTCATTCCCGTTGTCAGTATATGCTCCAGCTTCATCAGTTGA 3490      3500      3510      3520      3530      3540
                           |         |         |         |         |         |
huCFH 4.4kb cDNAseq  GTACCAATGCCAGAACTTGTATCAACTTGAGGGTAACAAGCGAATAACATGTAGAAATG
pRBS3FH2910#2.1
pRBS3FH2910#3.1      GTACCAATGCCAGAACTTGTATCAACTTGAGGGTAACAAGCGAATAACATGTAGAAATG
pRBS3FH2910#4.1      GTACCAATGCCAGAACTTGTATCAACTTGAGGGTAACAAGCGAATAACATGTAGAAATG 3550      3560      3570      3580      3590
                           |         |         |         |         |
huCFH 4.4kb cDNAseq  GACAATGGTCAGAACCACCAAAATGCTTACATCCGTGTGTAATATCCCGAGAAATTATG
pRBS3FH2910#2.1
pRBS3FH2910#3.1      GACAATGGTCAGAACCACCAAAATGCTTACATCCGTGTGTAATATCCCGAGAAATTATG
pRBS3FH2910#4.1      GACAATGGTCAGAACCACCAAAATGCTTACATCCGTGTGTAATATCCCGAGAAATTATG 3600      3610      3620      3630      3640      3650
                  |         |         |         |         |         |
Contig# 1       GAAAATTATAACATAGCATTAAGGTGGACAGCCAAACAGAAGCTTTATTCGAGAACAGG
huCFH 4.4kb cDNAseq GAAAATTATAACATAGCATTAAGGTGGACAGCCAAACAGAAGCTTTATTCGAGAACAGG
pRBS3FH2910#2.1
pRBS3FH2910#3.1
pRBS3FH2910#4.1  GAAAATTATAACATAGCATTAAGGTGGACAGCCAAACAG
```

*Fig. 7A-2*

```
                              930       940       950       960       970       980
                               |         |         |         |         |         |
Contig# 1
CFH RF3                       GFRISEENETTCYMGKWSSPPQCEGLPCKSPPEISHGVVAHMSDSYQYGEEVTYKCFE
pRBS3FH2910#2.1-RF2                                                  SDSYQYGEEVTYKCFE
pRBS3FH2910#3.1 RF2                                                  SDSYQYGEEVTYKCFE
pRBS3FH2910#4.-RF3

990      1000      1010      1020      1030      1040
                               |         |         |         |         |         |
CFH RF3                       GFGIDGPAIAKCLGEKWSHPPSCIKTDCLSLPSFENAIPMGEKKDVYKAGEQVTYTCA
pRBS3FH2910#2.1-RF2           GFGIDGPAIAKCLGEKWSHPPSCIKTDCLSLPSFENAIPMGEKKDLYKAGEQVTYTCA
pRBS3FH2910#3.1-RF2           GFGIDGPAIAKCLGEKWSHPPSCIKTDCPSLPSFENAIPMGEKKVLYKAGEQVTYTCA
pRBS3FH2910#4.1-RF3                                   LPSFENAIPMGEKKDLYKAGEPVTYTCA 1050      1060      1070      1080      1090      1100
                               |         |         |         |         |         |
CFH RF3                       TYYKMDGASNVTCINSRWTGRPTCRDTSCVNPPTVQNAYIVSRQMSKYPSGERVRYQC
pRBS3FH2910#2.1-RF2           TYYKMDGASNVTCINSRWTGRPTCRDTSCVNPPTVQNAYIVSRQMSKYPSGERVRYQC
pRBS3FH2910#3.1 RF2           TYCQMDGASNVTCINSRWTGRPTCRDTSCVNPPTVQNAYIVSRQMSKYPSGERVRYQC
pRBS3FH2910#4.1-RF3           TYYKMDGASNVTCINSRWTGRPTCRDTSCVNPPTVQNAYIVSRQMSKYPSGERVRYQC 1110      1120      1130      1140      1150      1160
                               |         |         |         |         |         |
CFH RF3                       RSPYEMFGDEEVMCLNGNWTEPPQCKDSTGKCGPPPPIDNGDITSFPLSVYAPASSVE
pRBS3FH2910#2.1-RF2           RSPYEMFGDEEVMCLNGNWTEPPQCKDSTGKCGPPPPIDNGDITS
pRBS3FH2910#3.1 RF2           RSPYEMFGDEEVMCLNGNWTEPPQCKDSTGKCGPPPPIDNGDITSFPLSVYAPASSVE
pRBS3FH2910#4.1-RF3           RSPYEMFGDEEVMCLNGNWTEPPQCKDSTGKCGPPPPIDNGDITSFPLSVYAPASSVE 1170      1180      1190      1200      1210
                               |         |         |         |         |
CFH RF3                       YQCQNLYQLEGNKRITCRNGQWSEPPKCLHPCVISREIMENYNIALRWTAKQKLYSRT
pRBS3FH2910#2.1-RF2
pRBS3FH2910#3.1 RF2           YQCQNLYQLEGNKRITCRNGQWSEPPKCLHPCVISREIM
pRBS3FH2910#4.1-RF3           YQCQNLYQLEGNKRITCRNGQWSEPPKCLHPCVISREIMENYNIALRWTAKQ
```

*Fig. 7B*

```
                          2540      2550      2560      2570      2580      2590
                            |         |         |         |         |         |
huCFH 4.4kb cDNAseq  CACAATATGACAACCACACTGAATTATCGGGATGGAGAAAAAGTATCTGTTCTTTGCCA
pZS3FH2576#3                                                       GTATCTGTTCTTTGCCA
pZS3FH2576#1/11                                                    GTATCTGTTCTTTGCCA 2600      2610      2620      2630      2640      2650
                            |         |         |         |         |         |
huCFH 4.4kb cDNAseq  AGAAAATTATCTAATTCAGGAAGGAGAAGAAATTACATGCAAAGATGGAAGATGGCAGT
pZS3FH2576#3         AGAAAATTATCTAATTCAGGAAGGGGAAGAAATTACATGCAAAGATGGAAGATGGCAGT
pZS3FH2576#1/11      AGAAAATTATCTAATTCAGGAAGGAGAAGAAATTACATGCAAAGATGGAAGATGGCAGT 2660      2670      2680      2690      2700      2710
                            |         |         |         |         |         |
huCFH 4.4kb cDNAseq  CAATACCACTCTGTGTTGAAAAAATTCCATGTTCACAACCACCTCAGATAGAACACGGA
pZS3FH2576#3         CAATACCACTCTGTGTTGAAAAAATTCCATGTTCACAACCACCTCAGATAGAACACGGA
pZS3FH2576#1/11      CAATACCACTCTGTGTTGAAAAAATTCCATGTTCACAACCACCTCAGATAGAACACGGA 2720      2730      2740      2750      2760      2770
                            |         |         |         |         |         |
huCFH 4.4kb cDNAseq  ACCATTAATTCATCCAGGTCTTCACAAGAAAGTTATGCACATGGGACTAAATTGAGTTA
pZS3FH2576#3         ACCATTAATTCATCCAGGTCTTCACAAGAAATTTATGCACATGGGACTAAATTGAGTTA
pZS3FH2576#1/11      ACCATTAATTCATCCAGGTCTTCACAAGAAATTTATGCACATGGGACTAAATTGAGTTA 2780      2790      2800      2810      2820      2830
                            |         |         |         |         |         |
huCFH 4.4kb cDNAseq  TACTTGTGAGGGTGGTTTCAGGATATCTGAAGAAAATGAAACAACATGCTACATGGGAA
pZS3FH2576#3         TACTTGTGAGGGTGGTTTCAGGATATCTGAAGAAAATGAAACAACATGCTACATGGGAA
pZS3FH2576#1/11      TACTTGTGAGGGTGGTTTCAGGATATCTGAAGAAAATGAAACAACATGCTACATGGGAA 2840      2850      2860      2870      2880      2890
                            |         |         |         |         |         |
huCFH 4.4kb cDNAseq  AATGGAGTTCTCCACCTCAGTGTGAAGGCCTTCCTTGTAAATCTCCACCTGAGATTTCT
pZS3FH2576#3         AATGGAGTTCTCCACCTCAGTGTGAAGGCCTTCCTTGTAAATCTCCACCTGAGATTTCT
pZS3FH2576#1/11      AATGGAGTTCTCCACCTCAGTGTGAAGGCCTTCCTTGTAAATCTCCACCTGAGATTTCT 2900      2910      2920      2930      2940      2950
                            |         |         |         |         |         |
huCFH 4.4kb cDNAseq  CATGGTGTTGTAGCTCACATGTCAGACAGTTATCAGTATGGAGAAGAAGTTACGTACAA
pZS3FH2576#3         CATGGTGTTGTAGCTCACATGTCAGACAGTTATCAGTATGGAGAAGAAGTTACGTACAA
pZS3FH2576#1/11      CATGGTGTTGTAGCTCACATGTCAGACAGTTATCAGTATGGAGAAGAAGTTACGTACAA 2960      2970      2980      2990      3000
                            |         |         |         |         |
huCFH 4.4kb cDNAseq  ATGTTTTGAAGGTTTTGGAATTGATGGGCCTGCAATTGCAAAATGCTTAGGAGAAAAAT
pZS3FH2576#3         ATGTTTTGAAGGTT
pZS3FH2576#1/11      ATGTTTTGAAGGTT
```

*Fig. 8A*

```
                          830       840       850       860       870       880
                          |         |         |         |         |         |
CFH RF3              NCSMAQIQLCPPPPQIPNSHNMTTTLNYRDGEKVSVLCQENYLIQEGEEITCKDGRWQS
pZS3FH2576#1/11 RF1                                    VSVLCQENYLIQEGEEITCKDGRWQS
pZS3FH2576#3 RF1                                       VSVLCQENYLIQEGEEITCKDGRWQS 890       900       910       920       930       940
                          |         |         |         |         |         |
CFH RF3              IPLCVEKIPCSQPPQIEHGTINSSRSSQESYAHGTKLSYTCEGGFRISEENETTCYMGK
pZS3FH2576#1/11 RF1  IPLCVEKIPCSQPPQIEHGTINSSRSSQEIYAHGTKLSYTCEGGFRISEENETTCYMGK
pZS3FH2576#3 RF1     IPLCVEKIPCSQPPQIEHGTINSSRSSQEIYAHGTKLSYTCEGGFRISEENETTCYMGK 950       960       970       980       990       1000
                          |         |         |         |         |         |
CFH RF3              WSSPPQCEGLPCKSPPEISHGVVAHMSDSYQYGEEVTYKCFEGFGIDGPAIAKCLGEKW
pZS3FH2576#1/11 RF1  WSSPPQCEGLPCKSPPEISHGVVAHMSDSYQYGEEVTY
pZS3FH2576#3 RF1     WSSPPQCEGLPCKSPPEISHGVVAHMSDSYQYGEEVTY
```

*Fig. 8B*

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (xi) SEQUENCE DESCRIPTION: SEQ ID NO:1:

```
Glu Asp Cys Asn Xaa Leu Pro Pro Arg Xaa Asn Thr
1               5                   10
```

(2) INFORMATION FOR SEQ ID NO:2:

(i) SEQUENCE CHARACTERISTICS:
      (A) LENGTH: 17 amino acids
      (B) TYPE: amino acid
      (C) STRANDEDNESS: single
      (D) TOPOLOGY: linear (xi) SEQUENCE DESCRIPTION: SEQ ID NO:2:

```
Gly Pro Tyr Phe Pro Val Ala Val Gly Lys Tyr Tyr Xaa Tyr Tyr Xaa
1               5                   10                  15
Asp
```

(2) INFORMATION FOR SEQ ID NO:3:

(i) SEQUENCE CHARACTERISTICS:
      (A) LENGTH: 24 amino acids
      (B) TYPE: amino acid
      (C) STRANDEDNESS: single
      (D) TOPOLOGY: linear (xi) SEQUENCE DESCRIPTION: SEQ ID NO:3:

```
Arg Pro Tyr Phe Pro Val Ala Val Gly Lys Tyr Tyr Ser Xaa Tyr Xaa
1               5                   10                  15
Asp Glu Xaa Phe Xaa Xaa Xaa Ser
```

20

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:4:

Ser Ser Gln Glu Ser Tyr Ala His Gly Thr Lys
1               5                  10

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:5:

Glu Asp Cys Asn Glu Leu Pro Pro Xaa Arg Asn Thr Glu Ile Leu Xaa
1               5                  10                  15

Gly Ser Trp Asp
            20

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:6:

Arg Pro Tyr Phe Pro Val Val Ala Val Gly Lys Tyr Tyr Ser Tyr Tyr
1               5                  10                  15

Xaa Asp Glu His Phe Glu Xaa Pro
            20

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:7:

Ser Leu Gly Asn Val Ile Met Val Gly Arg Lys Gly Glu Trp Val Ala
1               5                  10                  15

Leu Asn Pro Leu Arg Lys
            20

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:8:

Arg Pro Tyr Phe Pro Val Ala Val Gly Lys Tyr
1               5                  10

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

TCGTTCATTC TCCTTAT                                        17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

GCTGGTAAAT GTCCTCT                                        17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:11:

ATGTAATGAG GGGTATC                                        17

(2) INFORMATION FOR SEQ ID NO:12:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:12:

Arg Pro Tyr Phe Pro Val Ala Val Gly Lys Tyr Tyr Ser Tyr Tyr Cys
1              5                    10                15

Asp (2) INFORMATION FOR SEQ ID NO:13:

(i) SEQUENCE CHARACTERISTICS:
        (A) LENGTH: 24 amino acids
        (B) TYPE: amino acid
        (C) STRANDEDNESS:
        (D) TOPOLOGY: linear (xi) SEQUENCE DESCRIPTION: SEQ ID NO:13:

Arg Pro Tyr Phe Pro Val Ala Val Gly Lys Tyr Tyr Ser Tyr Tyr Cys
1              5                    10                15

Asp Glu His Phe Glu Thr Pro Ser
                  20

(2) INFORMATION FOR SEQ ID NO:14:

(i) SEQUENCE CHARACTERISTICS:
        (A) LENGTH: 21 amino acids
        (B) TYPE: amino acid
        (C) STRANDEDNESS:

(D) TOPOLOGY: linear (xi) SEQUENCE DESCRIPTION: SEQ ID NO:14:

Glu Asp Cys Asn Glu Leu Pro Pro Arg Arg Asn Thr Glu Ile Leu Thr
1               5                   10                  15

Gly Ser Trp Ser Asp
            20

(2) INFORMATION FOR SEQ ID NO:15:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:15:

Arg Pro Tyr Phe Pro Val Ala Val Gly Lys Tyr Tyr Ser Tyr Tyr Cys
1               5                   10                  15

Asp Glu His Phe Glu Thr Pro
            20

(2) INFORMATION FOR SEQ ID NO:16:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:16:

Ser Leu Gly Asn Val Ile Met Val Cys Arg Lys Gly Glu Trp Val Ala
1               5                   10                  15

Leu Asn Pro Leu Arg Lys
            20

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:17:

TCTGGATAAT CACAAGGTTT C                                           21

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:18:

GTCAGACAGT TATCAGTATG GAGAAGAAG                                   29

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:19:

-continued

CTGTTTGGCT GTCCACCTTA ATGCTATG                                    28

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

ACATGTAATG AGGGGTATCA A                                           21

(2) INFORMATION FOR SEQ ID NO:21:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (xi) SEQUENCE DESCRIPTION: SEQ ID NO:21:

ACATGTAATG AGGGGTATCA ATTGCTAGGT GAGATTAATT ACCGTGAATG TGACACAGAT   60

GGATGGACCA ATGATATTCC TATATGTGAA GTTGTGAAGT GTTTACCAGT GACAGCACCA  120

GAGAATGGAA AAATTGTCAG TAGTGCAATG GAACCAGATC GGGAATACCA TTTTGGACAA  180

GCAGTACGGT TTGTATGTAA CTCAGGCTAC AAGATTGAAG GAGATGAAGA AATGCATTGT  240

TCAGACGATG GTTTTTGGAG TAAAGAGAAA CCAAAGTGTG TGGAAATTTC ATGCAAATCC  300

CCAGATGTTA TAAATGGATC TCCTATATCT CAGAAGATTA TTTATAAGGA GAATGAACGA  360

TTTCAATATA AATGTAACAT GGGTTATGAA TACAGTGAAA GAGGAGATGC TGTATGCACT  420

GAATCTGGAT GGCGTCCGTT GCCTTCATGT GAAGAAAAAT CATGTGATAA TCCTTATATT  480

CCAAATGGTG ACTACTCACC TTTAAGGATT AAACACAGAA CTGGAGATGA AATCACGTAC  540

CAGTGTAGAA ATGGTTTTTA TCCTGCAACC CGGGGAAATA CAGCCAAATG CACAAGTACT  600

GGCTGGATAC CTGCTCCGAG ATGTACCTTG AAACCTTGTG ATTATCCAG             649

(2) INFORMATION FOR SEQ ID NO:22:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (xi) SEQUENCE DESCRIPTION: SEQ ID NO:22:

ACATGTAATG AGGGGTATCA ATTGCTAGGT GAGATTAATT ACCGTGAATG TGACACAGAT   60

GGATGGACCA ATGATATTCC TATATGTGAA GTTGTGAAGT GTTTACCAGT GACAGCACCA  120

GAGAATGGAA AAATTGTCAG TAGTGCAATG GAACCAGATC GGGAATACCA TTTTGGACAA  180

GCAGTACGGT TTGTATGTAA CTCAGGCTAC AAGATTGAAG GAGATGAAGA AATGCATTGT  240

TCAGACGATG GTTTTTGGGG TAAAGAGAAA CCAAAGTGTG TGGAAATTTC ATGCAAATCC  300

CCAGATGTTA TAAATGGATC TCCTATATCT CAGAAGATTA TTTATAAGGA GAATGAACGA  360

TTTCAATATA AATGTAACAT GGGTTATGAA TACAGTGAAA GAGGAGATGC TGTATGCACT  420

GAATCTGGAT GGCGTCCGTT GCCTTCATGT GAAGAAAAAT CATGTGATAA TCCTTATATT  480

CCAAATGGTG ACTACTCACC TTTAAGGATT AAACACAGAA CTGGAGATGA AATCACGTAC  540

CAGTGTAGAA ATGGTTTTTA TCCTGCAACC CGGGGAAATA C                     581

(2) INFORMATION FOR SEQ ID NO:23:

(i) SEQUENCE CHARACTERISTICS:
        (A) LENGTH: 240 amino acids
        (B) TYPE: amino acid
        (C) STRANDEDNESS:
        (D) TOPOLOGY: linear (xi) SEQUENCE DESCRIPTION: SEQ ID NO:23:

```
Phe Thr Leu Thr Gly Gly Asn Val Phe Glu Tyr Gly Val Lys Ala Val
 1               5                  10                  15

Tyr Thr Cys Asn Glu Gly Tyr Gln Leu Leu Gly Glu Ile Asn Tyr Arg
                20                  25                  30

Glu Cys Asp Thr Asp Gly Trp Thr Asn Asp Ile Pro Ile Cys Glu Val
            35                  40                  45

Val Lys Cys Leu Pro Val Thr Ala Pro Glu Asn Gly Lys Ile Val Ser
 50                  55                  60

Ser Ala Met Glu Pro Asp Arg Glu Tyr His Phe Gly Gln Ala Val Arg
 65                  70                  75                  80

Phe Val Cys Asn Ser Gly Tyr Lys Ile Glu Gly Asp Glu Glu Met His
                85                  90                  95

Cys Ser Asp Asp Gly Phe Trp Ser Lys Glu Lys Pro Lys Cys Val Glu
            100                 105                 110

Ile Ser Cys Lys Ser Pro Asp Val Ile Asn Gly Ser Pro Ile Ser Gln
        115                 120                 125

Lys Ile Ile Tyr Lys Glu Asn Glu Arg Phe Gln Tyr Lys Cys Asn Met
130                 135                 140

Gly Tyr Glu Tyr Ser Glu Arg Gly Asp Ala Val Cys Thr Glu Ser Gly
145                 150                 155                 160

Trp Arg Pro Leu Pro Ser Cys Glu Glu Lys Ser Cys Asp Asn Pro Tyr
                165                 170                 175

Ile Pro Asn Gly Asp Tyr Ser Pro Leu Arg Ile Lys His Arg Thr Gly
            180                 185                 190

Asp Glu Ile Thr Tyr Gln Cys Arg Asn Gly Phe Tyr Pro Ala Thr Arg
        195                 200                 205

Gly Asn Thr Ala Lys Cys Thr Ser Thr Gly Trp Ile Pro Ala Pro Arg
210                 215                 220

Cys Thr Leu Lys Pro Cys Asp Tyr Pro Asp Ile Lys His Gly Gly Leu
225                 230                 235                 240
```

(2) INFORMATION FOR SEQ ID NO:24:

(i) SEQUENCE CHARACTERISTICS:
        (A) LENGTH: 216 amino acids
        (B) TYPE: amino acid
        (C) STRANDEDNESS:
        (D) TOPOLOGY: linear (xi) SEQUENCE DESCRIPTION: SEQ ID NO:24:

```
Thr Cys Asn Glu Gly Tyr Gln Leu Leu Gly Glu Ile Asn Tyr Arg Glu
 1               5                  10                  15

Cys Asp Thr Asp Gly Trp Thr Asn Asp Ile Pro Ile Cys Glu Val Val
                20                  25                  30

Lys Cys Leu Pro Val Thr Ala Pro Glu Asn Gly Lys Ile Val Ser Ser
            35                  40                  45

Ala Met Glu Pro Asp Arg Glu Tyr His Phe Gly Gln Ala Val Arg Phe
 50                  55                  60

Val Cys Asn Ser Gly Tyr Lys Ile Glu Gly Asp Glu Glu Met His Cys
```

```
                65                  70                  75                  80
Ser Asp Asp Gly Phe Trp Gly Lys Glu Lys Pro Lys Cys Val Glu Ile
                85                  90                  95
Ser Cys Lys Ser Pro Asp Val Ile Asn Gly Ser Pro Ile Ser Gln Lys
               100                 105                 110
Ile Ile Tyr Lys Glu Asn Glu Arg Phe Gln Tyr Lys Cys Asn Met Gly
               115                 120                 125
Tyr Glu Tyr Ser Glu Arg Gly Asp Ala Val Cys Thr Glu Ser Gly Trp
               130                 135                 140
Arg Pro Leu Pro Ser Cys Glu Glu Lys Ser Cys Asp Asn Pro Tyr Ile
145                150                 155                 160
Pro Asn Gly Asp Tyr Ser Pro Leu Arg Ile Lys His Arg Thr Gly Asp
               165                 170                 175
Glu Ile Thr Tyr Gln Cys Arg Asn Gly Phe Tyr Pro Ala Thr Arg Gly
               180                 185                 190
Asn Thr Ala Lys Cys Thr Ser Thr Gly Trp Ile Pro Ala Pro Arg Cys
               195                 200                 205
Thr Leu Lys Pro Cys Asp Tyr Pro
               210                 215

(2) INFORMATION FOR SEQ ID NO:25:

(i) SEQUENCE CHARACTERISTICS:
        (A) LENGTH: 767 base pairs
        (B) TYPE: nucleic acid
        (C) STRANDEDNESS: single
        (D) TOPOLOGY: linear (xi) SEQUENCE DESCRIPTION: SEQ ID NO:25:

CATGGTGTTG TAGCTCACAT GTCAGACAGT TATCAGTATG AGAAGAAGT TACGTACAAA       60

TGTTTTGAAG GTTTTGGAAT TGATGGGCCT GCAATTGCAA AATGCTTAGG AGAAAAATGG     120

TCTCACCCTC CATCATGCAT AAAAACAGAT TGTCTCAGTT TACCTAGCTT TGAAAATGCC    180

ATACCCATGG GAGAGAAGAA GGATGTGTAT AAGGCGGGTG AGCAAGTGAC TTACACTTGT    240

GCAACATATT ACAAAATGGA TGGAGCCAGT AATGTAACAT GCATTAATAG CAGATGGACA    300

GGAAGGCCAA CATGCAGAGA CACCTCCTGT GTGAATCCGC CCACAGTACA AAATGCTTAT    360

ATAGTGTCGA GACAGATGAG TAAATATCCA TCTGGTGAGA GAGTACGTTA TCAATGTAGG    420

AGCCCTTATG AAATGTTTGG GGATGAAGAA GTGATGTGTT TAAATGGAAA CTGGACGGAA    480

CCACCTCAAT GCAAAGATTC TACAGGAAAA TGTGGGCCCC CTCCACCTAT TGACAATGGG    540

GACATTACTT CATTCCCGTT GTCAGTATAT GCTCCAGCTT CATCAGTTGA GTACCAATGC    600

CAGAACTTGT ATCAACTTGA GGGTAACAAG CGAATAACAT GTAGAAATGG ACAATGGTCA    660

GAACCACCAA AATGCTTACA TCCGTGTGTA ATATCCCGAG AAATTATGGA AAATTATAAC    720

ATAGCATTAA GGTGGACAGC CAAACAGAAG CTTTATTCGA GAACAGG                  767

(2) INFORMATION FOR SEQ ID NO:26:

(i) SEQUENCE CHARACTERISTICS:
        (A) LENGTH: 532 base pairs
        (B) TYPE: nucleic acid
        (C) STRANDEDNESS: single
        (D) TOPOLOGY: linear (xi) SEQUENCE DESCRIPTION: SEQ ID NO:26:

GTCAGACAGT TATCAGTATG AGAAGAAGT TACGTACAAA TGTTTTGAAG GTTTTGGAAT       60

TGATGGGCCT GCAATTGCAA AATGCTTAGG AGAAAAATGG TCTCACCCTC CATCATGCAT    120
```

```
AAAAACAGAT TGTCTCAGTT TACCTAGCTT TGAAAATGCC ATACCCATGG GAGAGAAGAA      180

GGATTTGTAT AAGGCGGGTG AGCAAGTGAC TTACACTTGT GCAACATATT ACAAAATGGA      240

TGGAGCCAGT AATGTAACAT GCATTAATAG CAGATGGACA GGAAGGCCAA CATGCAGAGA      300

CACCTCCTGT GTGAATCCGC CCACAGTACA AAATGCTTAT ATAGTGTCGA GACAGATGAG      360

TAAATATCCA TCTGGTGAGA GAGTACGTTA TCAATGTAGG AGCCCTTATG AAATGTTTGG      420

GGATGAAGAA GTGATGTGTT TAAATGGAAA CTGGACGGAA CCACCTCAAT GCAAAGATTC      480

TACAGGAAAA TGTGGGCCCC CTCCACCTAT TGACAATGGG GACATTACTT CA             532

(2) INFORMATION FOR SEQ ID NO:27:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (xi) SEQUENCE DESCRIPTION: SEQ ID NO:27:

GTCAGACAGT TATCAGTATG GAGAAGAAGT TACGTACAAA TGTTTTGAAG GTTTTGGAAT       60

TGATGGGCCT GCAATTGCAA AATGCTTAGG AGAAAAATGG TCTCACCCTC CATCATGCAT      120

AAAAACAGAT TGTCCCAGTT TACCTAGCTT TGAAAATGCC ATACCCATGG GAGAGAAGAA      180

GGTTTTGTAT AAGGCGGGTG AGCAAGTGAC TTACACTTGT GCAACATATT GCCAAATGGA      240

TGGAGCCAGT AATGTAACAT GCATTAATAG CAGATGGACA GGAAGGCCAA CATGCAGAGA      300

CACCTCCTGT GTGAATCCGC CCACAGTACA AAATGCTTAT ATAGTGTCGA GACAGATGAG      360

TAAATATCCA TCTGGTGAGA GAGTACGTTA TCAATGTAGG AGCCCTTATG AAATGTTTGG      420

GGATGAAGAA GTGATGTGTT TAAATGGAAA CTGGACGGAA CCACCTCAAT GCAAAGATTC      480

TACAGGAAAA TGTGGGCCCC CTCCACCTAT TGACAATGGG GACATTACTT CATTCCCGTT      540

GTCAGTATAT GCTCCAGCTT CATCAGTTGA GTACCAATGC CAGAACTTGT ATCAACTTGA      600

GGGTAACAAG CGAATAACAT GTAGAAATGG ACAATGGTCA GAACCACCAA AATGCTTACA      660

TCCGTGTGTA ATATCCCGAG AAATTATG                                        688

(2) INFORMATION FOR SEQ ID NO:28:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (xi) SEQUENCE DESCRIPTION: SEQ ID NO:28:

GTTTGCCTAG CTTTGAAAAT GCCATACCCA TGGGAGAGAA GAAGGATTTG TATAAGGCGG       60

GTGAGCCAGT GACTTACACT TGTGCAACAT ATTACAAAAT GGATGGAGCC AGTAATGTAA      120

CATGCATTAA TAGCAGATGG ACAGGAAGGC CAACATGCAG AGACACCTCC TGTGTGAATC      180

CGCCCACAGT ACAAAATGCT TATATAGTGT CGAGACAGAT GAGTAAATAT CCATCTGGTG      240

AGAGAGTACG TTATCAATGT AGGAGCCCTT ATGAAATGTT TGGGGATGAA GAAGTGATGT      300

GTTTAAATGG AAACTGGACG GAACCACCTC AATGCAAAGA TTCTACAGGA AAATGTGGGC      360

CCCCTCCACC TATTGACAAT GGGGACATTA CTTCATTCCC GTTGTCAGTA TATGCTCCAG      420

CTTCATCAGT TGAGTACCAA TGCCAGAACT TGTATCAACT TGAGGGTAAC AAGCGAATAA      480

CATGTAGAAA TGGACAATGG TCAGAACCAC CAAAATGCTT ACATCCGTGT GTAATATCCC      540

GAGAAATTAT GGAAAATTAT AACATAGCAT TAAGGTGGAC AGCCAAACAG                 590
```

(2) INFORMATION FOR SEQ ID NO:29:

(i) SEQUENCE CHARACTERISTICS:
        (A) LENGTH: 290 amino acids
        (B) TYPE: amino acid
        (C) STRANDEDNESS:
        (D) TOPOLOGY: linear (xi) SEQUENCE DESCRIPTION: SEQ ID NO:29:

```
Gly Phe Arg Ile Ser Glu Glu Asn Glu Thr Thr Cys Tyr Met Gly Lys
 1               5                  10                  15

Trp Ser Ser Pro Pro Gln Cys Glu Gly Leu Pro Cys Lys Ser Pro Pro
                20                  25                  30

Glu Ile Ser His Gly Val Val Ala His Met Ser Asp Ser Tyr Gln Tyr
            35                  40                  45

Gly Glu Glu Val Thr Tyr Lys Cys Phe Glu Gly Phe Gly Ile Asp Gly
50                  55                  60

Pro Ala Ile Ala Lys Cys Leu Gly Glu Lys Trp Ser His Pro Pro Ser
65                  70                  75                  80

Cys Ile Lys Thr Asp Cys Leu Ser Leu Pro Ser Phe Glu Asn Ala Ile
                85                  90                  95

Pro Met Gly Glu Lys Lys Asp Val Tyr Lys Ala Gly Glu Gln Val Thr
            100                 105                 110

Tyr Thr Cys Ala Thr Tyr Tyr Lys Met Asp Gly Ala Ser Asn Val Thr
            115                 120                 125

Cys Ile Asn Ser Arg Trp Thr Gly Arg Pro Thr Cys Arg Asp Thr Ser
130                 135                 140

Cys Val Asn Pro Pro Thr Val Gln Asn Ala Tyr Ile Val Ser Arg Gln
145                 150                 155                 160

Met Ser Lys Tyr Pro Ser Gly Glu Arg Val Arg Tyr Gln Cys Arg Ser
                165                 170                 175

Pro Tyr Glu Met Phe Gly Asp Glu Glu Val Met Cys Leu Asn Gly Asn
            180                 185                 190

Trp Thr Glu Pro Pro Gln Cys Lys Asp Ser Thr Gly Lys Cys Gly Pro
            195                 200                 205

Pro Pro Pro Ile Asp Asn Gly Asp Ile Thr Ser Phe Pro Leu Ser Val
            210                 215                 220

Tyr Ala Pro Ala Ser Ser Val Glu Tyr Gln Cys Gln Asn Leu Tyr Gln
225                 230                 235                 240

Leu Glu Gly Asn Lys Arg Ile Thr Cys Arg Asn Gly Gln Trp Ser Glu
                245                 250                 255

Pro Pro Lys Cys Leu His Pro Cys Val Ile Ser Arg Glu Ile Met Glu
            260                 265                 270

Asn Tyr Asn Ile Ala Leu Arg Trp Thr Ala Lys Gln Lys Leu Tyr Ser
            275                 280                 285

Arg Thr
290
```

(2) INFORMATION FOR SEQ ID NO:30:

(i) SEQUENCE CHARACTERISTICS:
        (A) LENGTH: 177 amino acids
        (B) TYPE: amino acid
        (C) STRANDEDNESS:
        (D) TOPOLOGY: linear (xi) SEQUENCE DESCRIPTION: SEQ ID NO:30:

```
Ser Asp Ser Tyr Gln Tyr Gly Glu Glu Val Thr Tyr Lys Cys Phe Glu
  1               5                  10                  15

Gly Phe Gly Ile Asp Gly Pro Ala Ile Ala Lys Cys Leu Gly Glu Lys
             20                  25                  30

Trp Ser His Pro Pro Ser Cys Ile Lys Thr Asp Cys Leu Ser Leu Pro
         35                  40                  45

Ser Phe Glu Asn Ala Ile Pro Met Gly Glu Lys Lys Asp Leu Tyr Lys
 50                      55                  60

Ala Gly Glu Gln Val Thr Tyr Thr Cys Ala Thr Tyr Lys Met Asp
 65                  70                  75                  80

Gly Ala Ser Asn Val Thr Cys Ile Asn Ser Arg Trp Thr Gly Arg Pro
                 85                  90                  95

Thr Cys Arg Asp Thr Ser Cys Val Asn Pro Pro Thr Val Gln Asn Ala
                100                 105                 110

Tyr Ile Val Ser Arg Gln Met Ser Lys Tyr Pro Ser Gly Glu Arg Val
            115                 120                 125

Arg Tyr Gln Cys Arg Ser Pro Tyr Glu Met Phe Gly Asp Glu Glu Val
130                 135                 140

Met Cys Leu Asn Gly Asn Trp Thr Glu Pro Pro Gln Cys Lys Asp Ser
145                 150                 155                 160

Thr Gly Lys Cys Gly Pro Pro Pro Ile Asp Asn Gly Asp Ile Thr
                165                 170                 175

Ser
```

(2) INFORMATION FOR SEQ ID NO:31:

(i) SEQUENCE CHARACTERISTICS:
    (A) LENGTH: 229 amino acids
    (B) TYPE: amino acid
    (C) STRANDEDNESS:
    (D) TOPOLOGY: linear (xi) SEQUENCE DESCRIPTION: SEQ ID NO:31:

```
Ser Asp Ser Tyr Gln Tyr Gly Glu Glu Val Thr Tyr Lys Cys Phe Glu
  1               5                  10                  15

Gly Phe Gly Ile Asp Gly Pro Ala Ile Ala Lys Cys Leu Gly Glu Lys
             20                  25                  30

Trp Ser His Pro Pro Ser Cys Ile Lys Thr Asp Cys Pro Ser Leu Pro
         35                  40                  45

Ser Phe Glu Asn Ala Ile Pro Met Gly Glu Lys Lys Val Leu Tyr Lys
 50                      55                  60

Ala Gly Glu Gln Val Thr Tyr Thr Cys Ala Thr Tyr Cys Gln Met Asp
 65                  70                  75                  80

Gly Ala Ser Asn Val Thr Cys Ile Asn Ser Arg Trp Thr Gly Arg Pro
                 85                  90                  95

Thr Cys Arg Asp Thr Ser Cys Val Asn Pro Pro Thr Val Gln Asn Ala
                100                 105                 110

Tyr Ile Val Ser Arg Gln Met Ser Lys Tyr Pro Ser Gly Glu Arg Val
            115                 120                 125

Arg Tyr Gln Cys Arg Ser Pro Tyr Glu Met Phe Gly Asp Glu Glu Val
130                 135                 140

Met Cys Leu Asn Gly Asn Trp Thr Glu Pro Pro Gln Cys Lys Asp Ser
145                 150                 155                 160

Thr Gly Lys Cys Gly Pro Pro Pro Ile Asp Asn Gly Asp Ile Thr
                165                 170                 175

Ser Phe Pro Leu Ser Val Tyr Ala Pro Ala Ser Ser Val Glu Tyr Gln
```

|     |     |     |
| --- | --- | --- |
|     | 180 | 185 | 190 |

Cys Gln Asn Leu Tyr Gln Leu Glu Gly Asn Lys Arg Ile Thr Cys Arg
      195                  200                205

Asn Gly Gln Trp Ser Glu Pro Pro Lys Cys Leu His Pro Cys Val Ile
210                    215                220

Ser Arg Glu Ile Met
225

(2) INFORMATION FOR SEQ ID NO:32:

(i) SEQUENCE CHARACTERISTICS:
        (A) LENGTH: 196 amino acids
        (B) TYPE: amino acid
        (C) STRANDEDNESS:
        (D) TOPOLOGY: linear (xi) SEQUENCE DESCRIPTION: SEQ ID NO:32:

Leu Pro Ser Phe Glu Asn Ala Ile Pro Met Gly Glu Lys Lys Asp Leu
1              5                    10                15

Tyr Lys Ala Gly Glu Pro Val Thr Tyr Thr Cys Ala Thr Tyr Tyr Lys
           20                  25              30

Met Asp Gly Ala Ser Asn Val Thr Cys Ile Asn Ser Arg Trp Thr Gly
        35                  40              45

Arg Pro Thr Cys Arg Asp Thr Ser Cys Val Asn Pro Pro Thr Val Gln
   50                 55              60

Asn Ala Tyr Ile Val Ser Arg Gln Met Ser Lys Tyr Pro Ser Gly Glu
65              70                75              80

Arg Val Arg Tyr Gln Cys Arg Ser Pro Tyr Glu Met Phe Gly Asp Glu
           85                  90              95

Glu Val Met Cys Leu Asn Gly Asn Trp Thr Glu Pro Pro Gln Cys Lys
             100               105            110

Asp Ser Thr Gly Lys Cys Gly Pro Pro Pro Ile Asp Asn Gly Asp
        115                120              125

Ile Thr Ser Phe Pro Leu Ser Val Tyr Ala Pro Ala Ser Ser Val Glu
130              135                140

Tyr Gln Cys Gln Asn Leu Tyr Gln Leu Glu Gly Asn Lys Arg Ile Thr
145                150              155           160

Cys Arg Asn Gly Gln Trp Ser Glu Pro Pro Lys Cys Leu His Pro Cys
           165                  170            175

Val Ile Ser Arg Glu Ile Met Glu Asn Tyr Asn Ile Ala Leu Arg Trp
           180                185              190

Thr Ala Lys Gln
        195

(2) INFORMATION FOR SEQ ID NO:33:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (xi) SEQUENCE DESCRIPTION: SEQ ID NO:33:

CACAATATGA CAACCACACT GAATTATCGG GATGGAGAAA AAGTATCTGT TCTTTGCCAA     60

GAAAATTATC TAATTCAGGA AGGAGAAGAA ATTACATGCA AAGATGGAAG ATGGCAGTCA    120

ATACCACTCT GTGTTGAAAA AATTCCATGT TCAACCAC CTCAGATAGA ACACGGAACC    180

ATTAATTCAT CCAGGTCTTC ACAAGAAAGT TATGCACATG GGACTAAATT GAGTTATACT    240

```
TGTGAGGGTG GTTTCAGGAT ATCTGAAGAA AATGAAACAA CATGCTACAT GGGAAAATGG      300

AGTTCTCCAC CTCAGTGTGA AGGCCTTCCT TGTAAATCTC CACCTGAGAT TTCTCATGGT      360

GTTGTAGCTC ACATGTCAGA CAGTTATCAG TATGGAGAAG AAGTTACGTA CAAATGTTTT      420

GAAGGTTTTG GAATTGATGG GCCTGCAATT GCAAAATGCT TAGGAGAAAA AT              472
```

(2) INFORMATION FOR SEQ ID NO:34:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (xi) SEQUENCE DESCRIPTION: SEQ ID NO:34:

```
GTATCTGTTC TTTGCCAAGA AAATTATCTA ATTCAGGAAG GGGAAGAAAT TACATGCAAA      60

GATGGAAGAT GGCAGTCAAT ACCACTCTGT GTTGAAAAAA TTCCATGTTC ACAACCACCT     120

CAGATAGAAC ACGGAACCAT TAATTCATCC AGGTCTTCAC AAGAAATTTA TGCACATGGG     180

ACTAAATTGA GTTATACTTG TGAGGGTGGT TTCAGGATAT CTGAAGAAAA TGAAACAACA     240

TGCTACATGG GAAAATGGAG TTCTCCACCT CAGTGTGAAG GCCTTCCTTG TAAATCTCCA     300

CCTGAGATTT CTCATGGTGT TGTAGCTCAC ATGTCAGACA GTTATCAGTA TGGAGAAGAA     360

GTTACGTACA AATGTTTTGA AGGTT                                           385
```

(2) INFORMATION FOR SEQ ID NO:35:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (xi) SEQUENCE DESCRIPTION: SEQ ID NO:35:

```
GTATCTGTTC TTTGCCAAGA AAATTATCTA ATTCAGGAAG GAGAAGAAAT TACATGCAAA      60

GATGGAAGAT GGCAGTCAAT ACCACTCTGT GTTGAAAAAA TTCCATGTTC ACAACCACCT     120

CAGATAGAAC ACGGAACCAT TAATTCATCC AGGTCTTCAC AAGAAATTTA TGCACATGGG     180

ACTAAATTGA GTTATACTTG TGAGGGTGGT TTCAGGATAT CTGAAGAAAA TGAAACAACA     240

TGCTACATGG GAAAATGGAG TTCTCCACCT CAGTGTGAAG GCCTTCCTTG TAAATCTCCA     300

CCTGAGATTT CTCATGGTGT TGTAGCTCAC ATGTCAGACA GTTATCAGTA TGGAGAAGAA     360

GTTACGTACA AATGTTTTGA AGGTT                                           385
```

(2) INFORMATION FOR SEQ ID NO:36:

(i) SEQUENCE CHARACTERISTICS:
        (A) LENGTH: 177 amino acids
        (B) TYPE: amino acid
        (C) STRANDEDNESS:
        (D) TOPOLOGY: linear (xi) SEQUENCE DESCRIPTION: SEQ ID NO:36:

```
Asn Cys Ser Met Ala Gln Ile Gln Leu Cys Pro Pro Pro Gln Ile
 1               5                  10                  15

Pro Asn Ser His Asn Met Thr Thr Thr Leu Asn Tyr Arg Asp Gly Glu
                20                  25                  30

Lys Val Ser Val Leu Cys Gln Glu Asn Tyr Leu Ile Gln Glu Gly Glu
            35                  40                  45

Glu Ile Thr Cys Lys Asp Gly Arg Trp Gln Ser Ile Pro Leu Cys Val
    50                  55                  60
```

Glu Lys Ile Pro Cys Ser Gln Pro Pro Gln Ile Glu His Gly Thr Ile
65                  70                  75                  80

Asn Ser Ser Arg Ser Ser Gln Glu Ser Tyr Ala His Gly Thr Lys Leu
                85                  90                  95

Ser Tyr Thr Cys Glu Gly Gly Phe Arg Ile Ser Glu Glu Asn Glu Thr
            100                 105                 110

Thr Cys Tyr Met Gly Lys Trp Ser Ser Pro Pro Gln Cys Glu Gly Leu
        115                 120                 125

Pro Cys Lys Ser Pro Pro Glu Ile Ser His Gly Val Val Ala His Met
    130                 135                 140

Ser Asp Ser Tyr Gln Tyr Gly Glu Glu Val Thr Tyr Lys Cys Phe Glu
145                 150                 155                 160

Gly Phe Gly Ile Asp Gly Pro Ala Ile Ala Lys Cys Leu Gly Glu Lys
                165                 170                 175

Trp (2) INFORMATION FOR SEQ ID NO:37:

(i) SEQUENCE CHARACTERISTICS:
        (A) LENGTH: 123 amino acids
        (B) TYPE: amino acid
        (C) STRANDEDNESS:
        (D) TOPOLOGY: linear (xi) SEQUENCE DESCRIPTION: SEQ ID NO:37:

Val Ser Val Leu Cys Gln Glu Asn Tyr Leu Ile Gln Glu Gly Glu Glu
1               5                   10                  15

Ile Thr Cys Lys Asp Gly Arg Trp Gln Ser Ile Pro Leu Cys Val Glu
            20                  25                  30

Lys Ile Pro Cys Ser Gln Pro Pro Gln Ile Glu His Gly Thr Ile Asn
        35                  40                  45

Ser Ser Arg Ser Ser Gln Glu Ile Tyr Ala His Gly Thr Lys Leu Ser
    50                  55                  60

Tyr Thr Cys Glu Gly Gly Phe Arg Ile Ser Glu Glu Asn Glu Thr Thr
65                  70                  75                  80

Cys Tyr Met Gly Lys Trp Ser Ser Pro Pro Gln Cys Glu Gly Leu Pro
                85                  90                  95

Cys Lys Ser Pro Pro Glu Ile Ser His Gly Val Val Ala His Met Ser
            100                 105                 110

Asp Ser Tyr Gln Tyr Gly Glu Glu Val Thr Tyr
        115                 120

(2) INFORMATION FOR SEQ ID NO:38:

(i) SEQUENCE CHARACTERISTICS:
        (A) LENGTH: 123 amino acids
        (B) TYPE: amino acid
        (C) STRANDEDNESS:
        (D) TOPOLOGY: linear (xi) SEQUENCE DESCRIPTION: SEQ ID NO:38:

Val Ser Val Leu Cys Gln Glu Asn Tyr Leu Ile Gln Glu Gly Glu Glu
1               5                   10                  15

Ile Thr Cys Lys Asp Gly Arg Trp Gln Ser Ile Pro Leu Cys Val Glu
            20                  25                  30

Lys Ile Pro Cys Ser Gln Pro Pro Gln Ile Glu His Gly Thr Ile Asn
        35                  40                  45

Ser Ser Arg Ser Ser Gln Glu Ile Tyr Ala His Gly Thr Lys Leu Ser

-continued

```
                50                      55                      60
Tyr Thr Cys Glu Gly Gly Phe Arg Ile Ser Glu Glu Asn Glu Thr Thr
65                      70                      75                      80

Cys Tyr Met Gly Lys Trp Ser Ser Pro Pro Gln Cys Glu Gly Leu Pro
                85                      90                      95

Cys Lys Ser Pro Pro Glu Ile Ser His Gly Val Val Ala His Met Ser
                100                     105                     110

Asp Ser Tyr Gln Tyr Gly Glu Glu Val Thr Tyr
            115                 120
```

METHODS AND COMPOSITIONS FOR SCREENING FOR OR MODULATING A TUMOR ASSOCIATED ANTIGEN This application claims the benefit of U.S. Provisional Applications 60/015,083, filed Apr. 9, 1996 and 60/038,614, filed Mar. 6, 1997.

TECHNICAL FIELD

The present invention is generally directed toward screening for or modulating a tumor associated antigen. The invention is more particularly related to detecting a complement Factor H-related protein, or a nucleic acid molecule encoding such a protein, associated with the presence of cancer, and to modulating the presence or activity of such a protein.

BACKGROUND OF THE INVENTION

The detection of new tumors or the recurrence of tumors remains an unfulfilled goal of humankind, despite enormous expenditures of both financial and human resources over the last twenty-five plus years. A number of cancers are treatable if detected at an early stage, but unfortunately go undetected in many patients for lack of a reliable screening procedure. For illustrative purposes, background for a particular cancer, bladder cancer, is described in more detail and is representative of cancers in need of new approaches, which the invention disclosed herein provides.

Bladder cancer is the fifth most common cancer in the United States. The American Cancer Society estimated that a total of 52,000 new cases would be detected in 1994 and that there would be 10,000 deaths resulting from this disease. Bladder cancer is more common in men than in women by a ratio of approximately three to one and has been shown to be highly associated with smoking as well as exposure to certain dyes. Carcinoma of the urinary bladder is the fourth most common malignancy among American men, and the eighth among women. Transitional cell carcinoma (TCC) is the most common type of bladder cancer representing greater than 90% of all cases. The remaining cases are squamous cell carcinomas (7%), adenocarcinomas (2%), and undifferentiated carcinomas (1%).

The diagnosis and management of TCC is often performed as follows. The patient presenting with such symptoms as hematuria or dysuria in the absence of infection undergoes a cystoscopy at which time the tumor is visualized. Although this procedure is invasive and unpleasant, it is highly accurate in predicting malignancy and is, thus, considered the gold standard. Urine cytology (i.e., the identification of tumor cells in voided urine) is also performed, and the combined results of the two methods may lead to an increase in sensitivity over that of cystoscopy alone. This is due to the fact that cytology occasionally allows detection of tumors which are not visible during cystoscopy, for example, flat tumors of the bladder (TIS) or those in the upper end of the bladder or the upper urinary tract.

Transurethral biopsy and resection are then usually performed with this procedure removing the apparent lesion as well as providing information as to the grade and stage of the tumor. The tumor is typically graded from G0 to G4 in decreasing state of differentiation. As with most cancers, the less differentiated the tumor the more aggressive the disease. With respect to stage or extent of invasion, TCC's of the bladder may be classified as superficial papillary (Ta and T1), muscle invasive (T2 and greater), or the relatively uncommon tumor in situ (TIS). The extent of invasion dictates the type of therapeutic approach employed and the follow-up procedures to monitor for disease recurrence.

Individuals with invasive TCC (Stage T2, T3, and T4) typically have poor prognoses. They are usually treated by radical cystectomy; however, in some cases the patient is unable to tolerate this surgery and is treated by radiation therapy or chemotherapy instead. This latter subgroup is monitored for disease recurrence by cystoscopy and urine cytology.

Approximately 75% of TCC patients are initially diagnosed as having either Ta or T1 disease. In part because bladder cancer is multifocal, initial resection and treatment of these patients is curative in less than half of the cases. Although patients presenting with Ta TCC usually recur, their tumors tend to be low grade, and only 10–15% of the tumors will progress to muscle invasive disease. In contrast, T1 patients will progress 30–50% of the time. Superficial TCC is usually treated by transurethral resection, intravesical therapy, or fulguration, and follow-up is usually by cystoscopy and voided urine cytology.

As mentioned above, current practice includes a preliminary diagnosis of TCC by cystoscopy and urine cytology, confirmatory diagnosis and staging and grading by biopsy, and routine follow-up of superficial and some invasive TCC by cystoscopy and urine cytology. Recurrence, especially within the first 12 months, is common, even when tumors have been diagnosed and treated prior to invasion of the bladder muscle. Therefore, patients with superficial TCC are typically monitored every three months for the first two years and, if there is no recurrence, every six months during the following year. Because cystoscopy is invasive and unpleasant and because urine cytology, although highly specific, is of variable reliability in detecting recurrence, there is a significant need for alternative diagnostic approaches.

Accordingly, there is a need in the art for a non-invasive diagnostic method with reliability in detecting occurrence or recurrence. The present invention fulfills this need and further provides other related advantages.

SUMMARY OF THE INVENTION

Briefly stated, the present invention provides a variety of methods and compositions for screening for cancer, and for treating tumor cells. The screening methods and compositions may be used on a one-time basis when cancer is suspected or on a periodic basis, e.g., to monitor an individual with an elevated risk of acquiring or reacquiring cancer.

In one aspect, the present invention provides a method of screening for a cancer comprising the step of detecting the presence of a tumor-associated human complement Factor H-related antigen or a nucleic acid molecule encoding the antigen, the nucleic acid molecule characterized by the ability of the nucleic acid molecule to hybridize under moderate stringency with the primer pair 42M/1040RT or the primer pair 2910M/3610RT.

Preferred embodiments of the methods for either aspect include detection of the antigen based on immunological properties, physical properties, enzymatic properties or combinations thereof, and detection of a nucleic acid molecule encoding the antigen by amplification of the molecule.

In a related aspect, the present invention provides a method of treating a tumor cell comprising the step of modulating a tumor-associated human complement Factor H-related antigen or a nucleic acid molecule encoding the antigen, the nucleic acid molecule characterized by the ability of the nucleic acid molecule to hybridize under moderate stringency with the primer pair 42M/1040RT or the primer pair 2910M/3610RT.

These and other aspects of the present invention will become evident upon reference to the following detailed description and attached drawings.

BRIEF DESCRIPTION OF THE DRAWINGS

FIG. 6A shows a partial DNA sequence from clone pRBB9FH410 (SEQ ID NO: 22) and

FIG. 6B the corresponding deduced amino acid sequence (SEQ ID NO: 24), as compared to the DNA and amino acid sequences for human CFH (SEQ ID NOS: 21 and 23, respectively).

FIG. 7A shows three partial DNA sequences from clone pRBS3FH2910 (SEQ ID NOS: 26–28) and FIG. 7B the corresponding deduced amino acid sequences (SEQ ID NOS: 30–32), as compared to the DNA and amino acid sequences for human CFH (SEQ ID NOS: 25 and 29, respectively).

FIG. 8A shows two partial DNA sequences from clone pZS3FH2576 (SEQ ID NOS: 24 and 35) and FIG. 8B the corresponding deduced amino acid sequences (SEQ ID NOS: 37 and 38), as compared to the DNA and amino acid sequences for human CFH (SEQ ID NOS: 33 and 36, respectively).

DETAILED DESCRIPTION OF THE INVENTION

Figure 1:
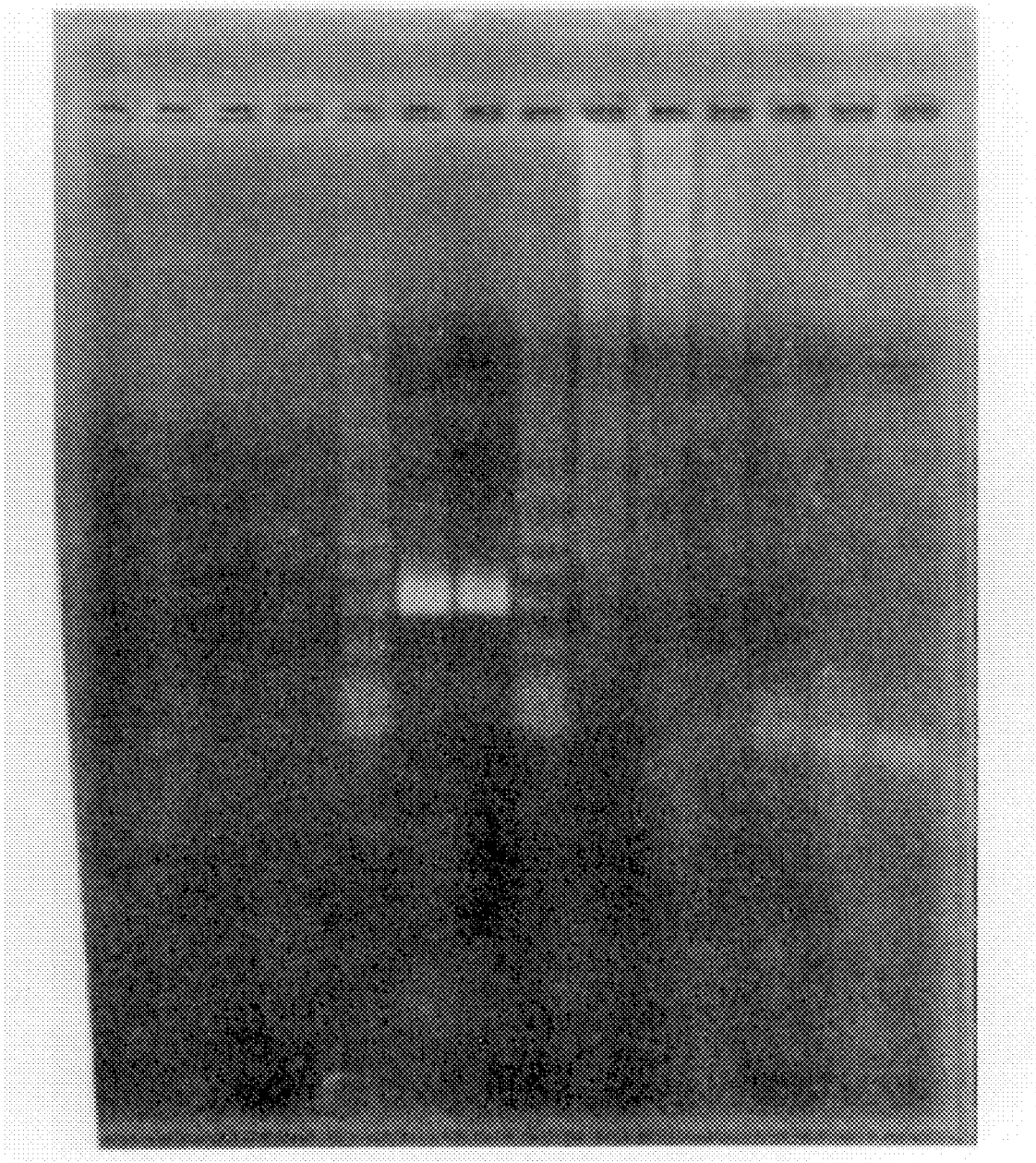
FIG. 1 shows the gel electrophoresis of the first-step RT-PCR amplification products, with lanes 1 to 10 beginning at the right side of the gel as lane 1. Lane 1: X44.1 mRNA; Lane 2: HTB-5 mRNA; Lane 3: HTB-9 mRNA; Lanes 4, 5, 6 same targets as 1, 2, 3 respectively except the RT primer was OligodT$_{16}$. Lanes 7 and 10, DNA molecular weight markers at 2000, 1500, 1000, 700, 500, 400, 300, 200, 100, and 50 base pairs. Lanes 8 and 9 are PAW 109, the kit positive control, at the expected size of 311 base pairs.

As noted above, the present invention is directed, in one aspect, toward methods of screening for cancer. As disclosed in the present invention, a protein antigen has been found to be associated with the presence of cancer ("tumor-associated") and found to survive in detectable concentrations in samples from warm-blooded animals, such as humans. The present disclosure describes, for example, the purification of a tumor-associated antigen from cancer patients, the generation of antibodies to the antigen, the characterization of the antigen by physical and biological properties, the development of immunoassays and non-immunoassays for the detection of the antigen or a nucleic acid molecule encoding the antigen, the evaluation of samples from normal individuals and cancer patients, demonstration of the production of the antigen by cancer cells, the determination that the antigen corresponds to protein products related to human complement Factor H, and the inhibition of biological activity of the antigen.

A wide variety of cancers may be screened. Representative examples of such cancers include urogenital, renal, head/neck and lung. Urogenital cancers include bladder, cervical and prostate. Head/neck cancers include cancers of the oral cavity, mouth and esophagus. As used herein, the term "screening for" includes detecting, monitoring or diagnosing. It will be evident to those in the art that if one wishes to screen for a particular type of cancer, this choice will guide the selection of a particular source of cell, tissue or sample to be tested. A sample in general may be a liquid or solid (e.g., cellular) sample taken from a tissue or organ, or after having been in contact with a tissue or organ. For example, a prostate sample includes a sample taken from a prostate or after having been in contact with a prostate. Representative types of prostate samples include prostate scraping and prostate tissue biopsy. A head/neck sample includes a sample taken from a head/neck or after having been in contact with a head/neck. Representative types of head/neck samples include swabs, scrapings and tissue biopsy of the oral cavity and esophagus. A lung sample includes a sample taken from a lung or after having been in contact with a lung. Representative types of lung samples include bronchial wash, sputum and tissue biopsy of the lung. A bladder sample includes a sample taken from a bladder or after having been in contact with a bladder. Representative types of bladder samples include urine, bladder wash, bladder scraping and bladder tissue biopsy. Urine may be voided or pre-voided (i.e., in a bladder). Urine may be removed from a bladder by using, for example, a catheter or a needle. A cervical sample includes a sample taken from a cervix or after having been in contact with a cervix. Representative types of cervical samples include cervical swab, cervical wash, cervical scraping and cervical tissue biopsy. Pretreatment of a sample may be desirable. For example, in the case of urine samples neutralizing the pH with buffer may be desirable.

The detection, isolation, characterization and identification of a protein antigen present in specimens derived from patients with cancer, but absent in specimens from normal individuals, indicates that this antigen is either a product of the cancer cells or is for some other reason present in specimens from these patients. If the antigen is expressed by cancer cells, it may be present in the supernatants taken from cultured human cancer cell lines at levels adequate to be measured by enzyme immunoassay specific for the antigen. cDNA derived by reverse transcriptase-polymerase chain reaction (RT-PCR) amplification from mRNA isolated from the same cancer cells can be used as well to provide evidence for expression of the gene which encodes for a product which is identical or very similar to the identified antigen. As disclosed herein, both types of experimental approaches confirm the expression of the antigen by cancer cell lines (e.g., bladder, cervical, renal and prostate cancer cell lines).

The tumor-associated protein antigen of the present invention has been determined, by sequence comparisons, surprisingly to be human complement Factor H-related. As cancer cells may produce more than one form of the protein, as used herein the term "human complement Factor H-related" refers to the human complement Factor H protein and variants thereof. The variants may be the result of mutations, alternate splicing or recombination events that alter nucleic acid molecules encoding human complement Factor H. In general, the amino acid sequence identity between a human complement Factor H-related protein from a tumor cell and human complement Factor H will be at least about 50%. More typically, the amino acid sequence identity will be at least about any integer from (and including) 50% to 100%, such as at least about 55%, 60%, 65%, 70%, 75%, 80%, 85%, 90% or 95% identity. Variants that are nearly identical to human complement Factor H have at least about 85% or 90% identity. As used herein, amino acid sequence "identity" is determined by the alignment of amino acid sequences and establishment of identical amino acid residues using the program GeneJockey II (1993) for Macintosh (Philip L. Taylor, published by Biosoft, Cambridge, UK). The program is run in the amino acid homology mode, using program default parameters. In the comparison of two sequences aligned by the program, the percent identity is calculated only for those positions where there is an amino acid residue present in both of the two sequences. In addition, a nucleic acid molecule encoding for a human complement Factor H-related protein will typically hybridize under moderately stringent conditions to one or the other or both of two primer pairs (42M/1040RT or 2910M/3610RT), as described below. This reflects conservation of certain sequences (disclosed herein) for tumor-associated human complement Factor H-related antigen. A protein may generally be identified as a tumor-associated human complement Factor H-related antigen based on the ability of a nucleic acid molecule encoding the protein to hybridize under moderately stringent conditions to one or the other or both of two primer pairs (42M/1040RT or 2910M/3610RT), as described below. Based on the disclosure herein, in combination with the methodologies known in the art, it will be evident to those in the art whether a protein is a tumor-associated human complement Factor H-related antigen, or whether a nucleic acid molecule encodes such a protein.

The antigen may be isolated in substantially pure form. Briefly, for example, urine samples of bladder cancer patients are clarified (e.g., by centrifugation) and concentrated (e.g., by hollow fiber concentrator). The concentrated sample is chromatographed on heparin agarose, and bound material eluted using a linear buffered NaCl gradient. Pooled fractions are concentrated. Purity can be assessed by sodium dodecyl sulfate-polyacrylamide gel electrophoresis ("SDS-PAGE") with appropriate protein stains. Alternatively, the antigen may be purified using an antibody against the antigen, as described for example below.

Following isolation of antigen, the polypeptide constituents may be identified. Typically, polypeptides are resolved by separation (e.g., by gel electrophoresis) under denaturing conditions (e.g., sodium dodecyl sulfate). Approximate molecular weights of polypeptides are assigned by comparison of their mobility to the mobility of polypeptides of known molecular weights on SDS-PAGE. Isolated antigen yields from certain cancers, for example, a band with an apparent molecular weight of approximately 151,000 on SDS-PAGE under reducing conditions (i.e., in the presence of DTT which is 1,4-dithiothreitol). Rather unusually, this band exhibits a lower apparent molecular weight (of approximately 138,000) on SDS-PAGE under non-reducing conditions (i.e., in the absence of a reducing agent). This somewhat anomalous electrophoretic behavior provides a convenient means for identifying the antigen.

Purified antigen, partially purified antigen or biological samples containing antigen may be used to produce antibodies that specifically bind to the antigen. Antibodies that specifically bind are those with an affinity of about $10^6$ liters/mol or greater. Either polyclonal antibodies or monoclonal antibodies may be generated. Polyclonal antibodies may be produced by immunization of an animal and subsequent collection of its sera. It is generally preferred to follow the initial immunization with one or more booster immunizations prior to sera collection. Monoclonal antibodies are generally produced by the method of Kohler and Milstein (*Nature* 256:495–497, 1975; *Eur. J. Immunol.* 6:511–519, 1976). Briefly, the lymph nodes and/or spleens of an animal injected with antigen in pure or impure form are fused with myeloma cells to form hybrid cell lines ("hybridomas" or "clones"). Each hybridoma secretes a single type of immunoglobulin specific for the antigen and, like the myeloma cells, has the potential for indefinite cell division.

Antigen in pure or impure form ("immunogen") is used for the immunization. Preferably, the animals are immunized with at least 100 ng each of the immunogen, most preferably greater than 500 ng each. For immunization, the immunogen may be adsorbed to a solid phase matrix, preferably to nitrocellulose paper. The paper is then introduced into the animal. Techniques for introduction of the adsorbed antigen preparation include implantation (U.S. Pat. No. 4,689,220) or solubilization of the solid phase and injection of the solubilized material (Knudsen, *Anal. Biochem.* 147:285–288, 1985). The solid phase matrix may be solubilized in an appropriate organic solvent (e.g., DMSO) and either mixed with adjuvant or saline, or injected directly.

Alternatively, the immunogen may be injected in the absence of a solid matrix and/or adjuvant. Injection or implantation may be intraperitoneal, intra-foot pad, subcutaneous, intramuscular or intravenous, but preferably intraperitoneal. The animals may also be injected with antigen complexed with adjuvant, such as Freund's adjuvant. Single or multiple booster immunizations are used. Between one and seven days prior to the fusion date, preferably on days one through four, intravenous injections of the immunogen may be given daily.

Between one and seven days, preferably four days, after the administration of the final booster immunization, spleens or portions thereof are harvested from the immunized animals. At this time, the lymph nodes may also be harvested and included in the cell preparation. The harvested organs are minced using techniques which disrupt the structure of the organ, but which are not detrimental to the lymphocytes. The organs are preferably minced with scissors, passed through a mesh screen and mixed with growth medium to enrich the preparation for lymphocytes. The minced and strained tissue is harvested by centrifugation, then mixed with growth medium to form a cell suspension. The red blood cells may be lysed by adding a hypotonic or hypertonic solution to the cell suspension. A preferred method for cell lysis is to add distilled water to the suspensions and quickly return the suspensions to an isotonic state with a hypertonic sodium chloride solution. Any remaining tissue may be removed by filtration through gauze.

The harvested cell suspension is then mixed with a myeloma cell line, preferably one which is syngeneic with the immunized animal. Myeloma cell lines from various species are widely available through, for example, American Type Culture Collection (ATCC), Rockville, Md. Myeloma cell lines commonly used include P3X63Ag8 (ATCC TIB 9), SP2/0-Ag14 (ATCC CRL 1581), FO (ATCC CRL 1646) and 210-RCY-Ag1 (Galfre et al., *Nature* 277:131, 1979).

The myeloma cells are cultured in an appropriate mammalian cell growth medium, a variety of which are generally known in the art and available from commercial sources. Mammalian cell lines are routinely grown between 36° C. and 40° C. under conditions which maintain an optimal pH between 6.0 and 8.0, preferably about pH 7.2. pH may be maintained through the use of a variety of buffer systems known in the art. A preferred buffer system involves growing the cells in a bicarbonate buffer in a humidified incubator containing $CO_2$, preferably about 7% $CO_2$.

The fusion between the lymphocytes from the immunized animal and the myeloma cells may be carried out by a variety of methods described in the literature. These methods include the use of polyethylene glycol (PEG) (Brown et al., *J. Biol. Chem.* 255:4980–4983, 1980) and electrofusion (Zimmerman and Vienken, *J. Membrane Biol.* 67:165–182, 1982). An electrofusion generator is commercially available from Biotechnologies and Experimental Research, Inc., San Diego, Calif.

Following the fusion, the cells are plated into multi-well culture plates, preferably 96-well plates. A reagent which selectively allows for the growth of the fused myeloma cells over the unfused cells is added to the culture medium. A preferred selection technique uses HAT (hypoxanthine, aminopterin, thymidine) selection. Other selection techniques may also be used depending on the myeloma cell line chosen.

Alternative methods of producing monoclonal antibodies utilize in vitro immunization techniques. Lymphocytes may be harvested from lymphoid organs, such as spleen or lymph nodes, or from whole blood as peripheral blood lymphocytes. The lymphocytes are put into culture in the presence of the appropriate immunogen. Often immunostimulatory polypeptides will be added to the culture medium concurrently. At various times following the culturing of the lymphocytes in vitro, the lymphocytes are harvested and fused with a myeloma cell line as described above.

Other techniques for producing and maintaining antibody secreting lymphocyte cell lines in culture include viral transfection of the lymphocyte to produce a transformed cell line which will continue to grow in culture. Epstein-Barr virus (EBV) has been used for this technique. EBV transformed cells do not require fusion with a myeloma cell to allow continued growth in culture.

Thymocytes may be used as a feeder layer to condition the medium for the fused cells. Alternatively, peritoneal macrophages or non-immune spleen cells may be used as a feeder layer. Another alternative is to use conditioned medium from thymocytes or macrophages. Thymocytes may be prepared from juvenile mice less than 8 weeks old. The thymus glands are harvested and minced using techniques which disrupt the thymus gland but are not detrimental to the thymocytes. This procedure is preferably carried out using scissors to mince the tissue, followed by passage of the tissue through a mesh screen. The minced and strained cell material is then harvested by centrifugation. Cell suspensions are made using growth medium. Any remaining connective tissue may be removed by filtration through gauze.

At an appropriate time following the day the cells are fused, the fused cells (hybridomas) are then analyzed for the production of antibody against the antigen. This "screening" can be done by a wide variety of techniques, including Western blot, ELISA, immunoprecipitation, effect on biological activity assays and immunocytochemical staining. These techniques and others are well described in the literature. (See, for example, J. G. R. Hurrell (ed.), *Monoclonal Hybridoma Antibodies: Techniques and Applications*, CRC Press Inc., Boca Raton, Fla., 1982.) Introduction of a screening procedure permits further definition of antibodies of useful reactivity. For example, antigen purified from a biological sample of a patient with a bladder cancer may be used in any of the above-named techniques to define antibodies which react, for example, to determinants which are common to patients with the disease.

Hybridomas which secrete antibodies of interest are maintained in culture. The cells are expanded in culture and at the same time may be cloned in such a manner as to obtain colonies originating from single cells. This provides for the monoclonal nature of the antibodies obtained from the hybridomas. A wide variety of techniques exist for cloning cells, including limiting dilution, soft agar cloning and fluorescence-activated cell sorting.

Once clones of cells are obtained, they are re-assayed for the production of the antibody of interest. These cells are then expanded in culture to allow for the production of larger amounts of the antibody. Methods for expansion of the cells include maintaining the cells in culture, placement of the cells in a bioreactor or other type of large-scale cell culture environment, or culturing the cells using various agar or gelatin carrier matrices. Antibodies are then isolated from the cell culture media.

Antibodies may be purified from conditioned media or ascites fluid by a variety of methods known in the art. These methods include ammonium sulfate precipitation, ion exchange chromatography (see Hurrell, ibid.) and high pressure liquid chromatography using a hydroxylapatite support (Stanker et al., *J. Immunol. Methods* 76:157, 1985). A preferred method for purifying antibodies from conditioned media or ascites fluid utilizes a commercially available Protein A-Sepharose® CL-4B column or Protein G Sepharose® (Pharmacia, Piscataway, N.J.; Sigma, St. Louis, Mo.) or ABX mixed ion exchange resin (J T Baker, Phillipsburg, N.J.). Antibodies may be purified with these columns using conditions suggested by the manufacturer.

As disclosed herein, the antigen which is found to be associated with the presence of cancer may be detected in a wide variety of ways, including by detecting the antigen itself or a nucleic acid molecule encoding the antigen. Methods for detecting the presence (i.e., qualitative or quantitative) of the antigen include those based on its physical properties, immunological properties, enzymatic properties and combinations thereof. For example, regarding physical properties, the antigen's unique polypeptide mobility on SDS-PAGE under reducing and non-reducing conditions may be exploited for a determination as to whether antigen is present in a sample. More specifically, for example, as described herein, a polypeptide with an apparent molecular weight on SDS-PAGE of about 151,000 under reducing conditions exhibits a lower molecular weight of about 138,000 under non-reducing conditions.

Alternatively, the presence of antigen may be detected by immunological means. The means for detecting the presence of antigen may be in a direct or indirect test format. In a direct test format, that which is observed or measured is proportional to (i.e., directly reflective of) antigen present in a sample. Conversely, in an indirect test format, that which is observed or measured is inversely proportional to (i.e., indirectly reflective of) antigen present in a sample. Indirect formats include competitive and inhibition assay formats. As used herein, the term "antibody" includes both polyclonal and monoclonal antibodies; and may be an intact molecule, a fragment thereof, or a functional equivalent thereof, and may be genetically engineered. Examples of antibody fragments include $F(ab')_2$, Fab', Fab and Fv. Detection may be, for example, by Western blot analysis utilizing antigen immobilized on nitrocellulose or Immobilon or similar matrix, in conjunction with specific antibodies to the antigen. Detection can also be achieved by immunoassay. In one embodiment, antigen is isolated from a sample and contacted with an appropriate detection antibody. Antigen may be isolated by capture on a solid support (e.g., heparin agarose) or with a "capture" antibody prior to or simultaneous with a "detection" antibody. In another embodiment, immunocomplexes are formed between an antibody and antigen, without prior purification of the antigen. Incubation of a sample with an antibody is under conditions and for a time sufficient to allow immunocomplexes to form. Detection of antigen by immunological means is also amenable to quantification where it is desired to determine the amount of antigen.

Detection of one or more immunocomplexes formed between antigen and an antibody specific for the antigen may be accomplished by a variety of known techniques, including radioimmunoassays (RIA) and enzyme linked immunosorbent assays (ELISA).

The immunoassays known in the art include the double monoclonal antibody sandwich immunoassay technique of David etal. (U.S. Pat. No. 4,376,110); monoclonal-polyclonal antibody sandwich assays (Wide et al., in Kirkham and Hunter (eds.), *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al. , *J. Biol. Chem.* 255:4980–4983, 1980); enzyme-linked immunosorbant assays as described by, for example, Raines and Ross (*J. Biol. Chem.* 257:5154–5160, 1982); immunocytochemical techniques, including the use of fluorochromes (Brooks et al. , *Clin. Exp. Immunol.* 39: 477, 1980); and neutralization of activity (Bowen-Pope et al. , *Proc. Natl. Acad. Sci. USA* 81:2396–2400, 1984). In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876.

For detection purposes, the antibodies may either be labeled or unlabeled. When unlabeled, the antibodies find use in agglutination assays. In addition, unlabeled antibodies can be used in combination with other labeled antibodies (second antibodies) that are reactive with the antibody, such as antibodies specific for immunoglobulin. Alternatively, the antibodies can be directly labeled. Where they are labeled, the reporter group can include radioisotopes, fluorophores, enzymes, luminescers, or visible particles (e. g. , colloidal gold and dye particles). These and other labels are well known in the art and are described, for example, in the following U.S. Pat. Nos. 3,766,162; 3,791,932; 3,817,837; 3,996,345; and 4,233,402.

Typically in an ELISA assay the target antigen (for a competitive or inhibition assay format) or immobilized capture antibody is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing antigen. The sample can be applied neat, or, more often, it can be diluted, usually in a buffered solution which contains a small amount (0.1%–5.0% by weight) of protein, such as BSA, NGS, or BLOTTO. After incubating for a sufficient length of time to allow specific binding to occur, the well is washed to remove unbound protein and then incubated with a detection antibody labeled with a reporter group, or an anti-immunoglobulin antibody labeled with a reporter group. The reporter group can be chosen from a variety of enzymes, including horseradish peroxidase, betagalactosidase, alkaline phosphatase, and glucose oxidase. Sufficient time is allowed for specific binding to occur, the well is again washed to remove unbound conjugate, and the substrate for the enzyme is added. Color is allowed to develop and the optical density of the contents of the well is determined visually or instrumentally.

In one preferred embodiment of the present invention, a reporter group is bound to the detection antibody. The step of detecting an immunocomplex involves removing substantially any unbound antibody and then detecting the presence or absence of the reporter group.

In another preferred embodiment, a reporter group is bound to a second antibody capable of binding to the antibody specific for antigen. The step of detecting an immunocomplex involves (a) removing substantially any unbound antibody, (b) adding the second antibody, (c) removing substantially any unbound second antibody and then (d) detecting the presence or absence of the reporter group. Where the antibody specific for the fragment is derived from a mouse, the second antibody is an anti-murine antibody.

In a third preferred embodiment for detecting an immunocomplex, a reporter group is bound to a molecule capable of binding to the immunocomplex. The step of detecting involves (a) adding the molecule, (b) removing substantially any unbound molecule, and then (c) detecting the presence or absence of the reporter group. An example of a molecule capable of binding to the immunocomplex is protein A.

It will be evident to one skilled in the art that a variety of methods for detecting the immunocomplex may be employed within the present invention. Reporter groups suitable for use in any of the methods include radioisotopes, fluorophores, enzymes, luminescers, and visible particles (e.g., colloidal gold and dye particles).

As disclosed herein, this antigen, which is associated with the presence of cancer, is bound by complement factor fragment C3b. Therefore, C3b may be used in assays (such as those described above) that utilize a capture molecule and a detection molecule for detecting antigen. For example, C3b may be immobilized on a solid support and used to capture antigen when contacted with a sample containing antigen. Another molecule which is specific for antigen, such as an antibody, may be used to detect any antigen bound to immobilized C3b. It may be desirable to wash the immobilized C3b, after introducing a sample suspected of containing antigen, prior to and/or subsequent to contacting with a detection molecule. Alternatively, this antigen possesses enzyme cofactor activity, e.g., whereby it acts as a cofactor for the digestion of C3b by Factor I of the complement system. Therefore, the presence of antigen may be determined by contacting a sample (suspected of containing antigen) with C3b and Factor I, and assaying for the digestion of C3b. In the presence of antigen and Factor I, the C3b α' fragment at a molecular weight of about 108,000 disappears with the concurrent appearance of fragments with molecular weights of 67,000 and 47,000. This digestion may be detected by a variety of ways, including SDS-PAGE.

Alternatively, rather than detecting the antigen itself, a nucleic acid molecule encoding the antigen can be detected. Such a nucleic acid molecule may be a deoxyribonucleic acid (DNA) or a ribonucleic acid (RNA). Generally, a nucleic acid molecule encoding for the antigen is detected by amplification of the nucleic acid. A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing ligase chain reaction ("LCR") or polymerase chain reaction ("PCR") (see U.S. Pat. Nos. 4,683,195, 4,683,202, and 4,800,159) (see also U.S. Pat. No. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, *Appl. Environ. Microbiol.* 60:348–352, 1994). PCR may also be used in combination with reverse dot-blot hybridization (Iida et al., *FEMS Microbiol. Lett.* 114:167–172, 1993). PCR products may be quantitatively analyzed by incorporation of dUTP (Dupláa et al., *Anal. Biochem.* 212:229–236, 1993), and samples may be filter sampled for PCR-gene probe detection (Bej et al., *Appl. Environ. Microbiol.* 57:3529–3534, 1991).

Primers for the amplification of a selected sequence should be selected from sequences that are highly specific to the antigen and form stable duplexes with the target sequence. The primers should also be non-complementary, especially at the 3' end, should not form dimers with themselves or other primers, and should not form secondary structures or duplexes with other regions of DNA. In general, primers (such as those described in greater detail below) of about 18 to 30 nucleotides are preferred, and can be easily synthesized using techniques well known in the art. PCR products, and other nucleic acid amplification products, may be quantitated using techniques known in the art (Dupláa et al., *Anal. Biochem.* 212:229–236, 1993; Higuchi et al., *Bio/Technology* 11:1026–1030).

A preferred embodiment involves assaying for the presence of specific messenger RNA (mRNA) encoding the antigen. More specifically, for example, as described herein, a cell sample may be lysed and the mRNA isolated, amplified and examined for the presence of mRNA specific for the antigen. A variety of procedures may be used to detect the presence of antigen-specific mRNA. A particularly preferred method includes RT-PCR (Reverse Transcriptase based Polymerase Chain Reaction) amplification of mRNA.

Detecting the presence of antigen in a cell, tissue or sample has a variety of uses. For example, the present invention may be used for diagnostic purposes to screen warm-blooded animals, such as humans, for cancer (or a particular cancer depending upon the source of the particular cell, tissue or sample). Similarly, the present invention may be used to monitor warm-blooded animals. In particular, a preferred use is to follow patients who have been previously diagnosed and treated for cancer. Patients who are in remission (or may in fact be cured) can be monitored for the reappearance of cancer. It will be evident to those in the art that it may be desirable to use the present invention in conjunction with one or more other tests for cancer (or a particular cancer) to confirm positive or negative results obtained from use of the present invention.

The unexpected presence of a complement Factor H-related protein in cell culture supernatants from epithelial cancer cells (Example VI, Table 7), and the demonstration that its mRNA is produced by cancer cells (Example VI, Table 7), suggest that it plays a significant role in cancer biology. Data presented below (Example III.F) demonstrate that a biological activity of the antigen is to accelerate the complement Factor I-mediated degradation of C3b. The role of C3b in vivo is the assembly of the membrane attack complex (MAC) prior to lysis of an appropriate target. Because these proteins are members of the Alternative Complement Pathway, cell lysis may take place independent of the presence of circulating antibodies to any of the cancer cell antigens. Although not wishing to be bound by theory, in view of the activity of the antigen described herein, its production by cancer cells may locally promote the degradation of C3b, thereby inhibiting the formation of the MAC and preventing tumor cell lysis by complement. Since the production of the antigen by tumor cells may afford a survival advantage, interrupting the production of the antigen or blocking its decay accelerator activity restores susceptibility of the tumor to complement-mediated cell lysis, thus offering a new approach to cancer therapy.

Irrespective of the exact function(s) of the complement Factor H-related protein in tumor biology, the present invention provides for the modulation of the antigen as a means for treating cancers. It will be evident to those of ordinary skill in the art that the antigen may be modulated in a variety of ways. A preferred method of interrupting the production of the antigen is by use of DNA, or PNA (peptide nucleic acid), constructs with base sequence complementary to the antigen's mRNA. Such an approach is generically termed antisense technology. Typically, the complement Factor H antisense DNA is inserted into an appropriate vector (virus) which delivers it to the tumor cells. Once inside the target cells, the antisense construct would specifically bind to mRNA coding for the complement Factor H-related protein, thereby preventing its translation. Primary among the other methods which could be used to interrupt production of the antigen would be the use of specific molecules which block the transcription of the specific gene or genes coding for the complement Factor H-related protein. Chemicals designed to block the ability of the tumor cell to produce antigen would preferably be delivered in the vicinity of the tumor, rather than systemically, since systemic introduction of such materials could decrease the normal production of complement Factor H by the liver, compromising the host's ability to regulate complement activity. In modulation of antigen production, it is desired to eliminate the production of all complement Factor H-related protein by tumor cells.

Another approach to antigen modulation is to use reagents to inhibit the activity of complement Factor H activity. Unlike inhibition of antigen production, the dosage used with these reagents should preferably result in an inhibition of 70%–95% of the Factor H activity. One family of such inhibitors-monoclonal antibodies, or fragments which bind the antigen at a site which blocks its ability to degrade C3b—is presented as a representative example of modulation of antigen activity as an approach to cancer therapy (Example VII). In this example, certain antibodies which bind antigen are shown to accelerate the complement-mediated lysis of rabbit red blood cells and HL-60, a human tumor cell line. With these reagents, as with those described above, delivery should preferably be administered to the tumor site, rather than systemically. For the antibodies described above, reagent affinities should be at least about $10^6$ liters/mole and doses should be within the range of about 0.01 μg/kg body weight to 10 mg/kg body weight. In addition, the preferred type of tumor to be treated in this manner would be distinctly separate from the circulatory system, since blood itself contains high concentrations of complement Factor H. An antibody may be replaced by, or supplemented with, any peptide or other organic molecule which specifically binds to complement Factor H-related protein and blocks its biological activity.

The following examples are offered by way of illustration and not by way of limitation.

EXAMPLES

Example I

DEVELOPMENT OF MONOCLONAL ANTIBODIES

A. Antigen

The antigen source for immunization was a pool of Heparin-Agarose fractionated urines from clinically diagnosed bladder cancer patients. (The purification method is described in detail in Example III.A.1. below.) Twenty-four hour urine samples were centrifuged in a Beckman centrifuge (Fullerton, Calif.), Model #J2-21, S/N 5539, using a JA-10 rotor at 6,000 rpm for 20 minutes. The clarified urine sample was then concentrated using an Amicon stirred cell, 76 mm, (cat# 5124) fitted with a YM30 membrane MWCO 30,000 dalton (Amicon, cat# 13742) or a Microgon hollow fiber concentrator, 50,000 MWCO (cat# M15S-260-01N) to approximately 100× concentration. The concentrated sample was diluted 1:1 with 25 mM Tris-HCl pH 7.4 and loaded onto a column of Heparin-Affigel (BioRad, Richmond, Calif., cat# 153-6173), equilibrated in 25 mM Tris-HCl pH 7.4, at a flow rate of 2.0 mL/min. The sample was followed with equilibration buffer until the $A_{280}$ elution profile returned to background. Bound material was eluted with a linear NaCl gradient from 0 to 250 mM NaCl in 25 mM Tris-HCl pH 7.4, followed by 50 mL of 250 mM NaCl, 25 mM Tris-HCl, pH 7.4, and finally 20 mL of a 10× PBS, pH 7.4, solution. Five mL fractions were collected and fractions from the trailing half of the elution peak were pooled. Pooled fractions were concentrated with an Amicon stirred cell, 43 mm (cat# 5122), fitted with a YM30 membrane, MWCO 30,000 dalton (cat# 13722). Fractions comprising the pooled antigen are shown below:

|  | Pool I |
| --- | --- |
| Patient 1 | fractions 13–31 |
| Patient 1 | fractions 14–30 |
| Patient 2 | fractions 11–19 |
| Patient 3 | fractions 11–24 |
|  | Pool II (1.5 mg/mL) |
| Pool I | 1 mL |
| Patient 2 | fractions 11–19 1 mL |
| Patient 3 | fractions 11–24 1 mL |
| Patient 4 | fractions 11–20 1 mL |

B. Immunizations

Five female BALB/c mice, of 8–10 weeks of age, were immunized intraperitoneally with 0.2 mL of a 1:1 emulsion of Pool II in Freund's Complete Adjuvant (Difco, Detroit, Mich.). Three weeks later, booster immunizations of 0.1 mL containing 10 μg of protein of an emulsion in incomplete Freund's Adjuvant was administered to the rear footpads and peritoneum. Ten days later each mouse was sampled for antibody response via retro-orbital bleeds and the sera were tested via an ELISA described below for titers. Mouse number 340 showed the highest titer and was chosen for fusion four days after boosting in the footpads and peritoneum with 15 μg of Pool II in phosphate buffered saline.

C. Fusion

Four days after the last immunization animal # 340 was sacrificed, the popliteal and inguinal lymph nodes and the spleen were collected and used for fusion. Fusion was carried out by a modification of the method of Fazekas De St. Groth and Scheidigger, *J. Immunol. M.* 35:1–21, 1980. The parent hybridoma line FO (ibid.), obtained from the ATCC, was used for fusion, at a ratio of one to five lymphocytes. PEG-DMSO (Sigma, St. Louis, Mo.) fusogen was used, and the cells plated out in Iscove's Modified Dulbecco's Medium (IMDM) with penicillin-streptomycin and hypoxanthine/thymidine (HT) supplement at a density of $2 \times 10^4$ cells/well with $2.58 \times 10^3$ peritoneal macrophages from unimmunized BALB/C mice added as feeders. The fusion was divided into two parts, in the first part forty-eight 96 well plates were seeded at the above density in media containing 1% fetal bovine serum (FBS). The second part consisted of 49 plates seeded at the same density in media containing 10% FBS. A total of 97 plates, or 9,312 wells were used. The plates were incubated at 37° C. in 7% $CO_2$ at 100% humidity. The next day 100 μl of selective media consisting of IMDM-HT with 2× methotrexate ($8 \times 10^{-7}$ M) and appropriate FBS concentration was added. The plates were returned to the incubator and not disturbed for six days. On day seven the plates were removed from the incubator and approximately 150 μl of media was removed via aspiration with a sterile eight place manifold. Complete IMDM with HT and appropriate FBS was added to each well using a Brinkman eight place pipette. The plates were returned to the incubator for another five to six days before screening. The fusion plates were examined each morning for wells showing growth levels suitable for screening, and were analyzed that day.

Within one week of the fusion, the plates containing the 1% FBS medium were clearly lagging in growth, and were therefore supplemented to 10% FBS. Thereafter, those wells selected from the plates initially plated in 1% FBS were designated as MOFI-followed by a number indicating the order of selection, those from the 10% FBS plates were designated with the MOFX prefix.

D. Post-Fusion Cell Culture

Wells selected via the screening assays were immediately transferred to 24 well plates containing 1 mL of complete IMDM containing 10% FBS. A sample of cells was also used to immediately re-clone the hybridomas by a serial limiting dilution procedure. This consisted of transferring a 10 μl sample of cells from the chosen well of the 96 well plate to the first well of a fresh 96 well plate previously filled with 100 μl of complete IMDM with 10% of a cloning supplement prepared from murine macrophages and thymocytes (Condimed, Boehringer-Mannheim Corp., Indianapolis, Ind.). Cells from the first well were serially diluted in the first column of wells by transferring 100 μl from the first well to the second, then from the second to the third, etc. The remaining 100 μl removed from the last well of the column is transferred back to the first well. The wells of the first column were then serially diluted across the plate by transfer of 50 μl of cell suspension using an 8 place pipette. Finally, 100 μl of cloning media was added to each well, and the plates incubated for approximately two weeks before subclones were ready for re-screening. Following growth in the 24 well plates, the clones were transferred to six well plates with 5–6 mL of culture media, the plates were incubated until near confluent growth was observed. A sample of the cells were removed for storage in a cryogenic freezer in 5% DMSO in FBS, and the remaining cells were transferred to a T-75 flask with 10 mL media for producing spent media for further testing.

E. Stabilization of Subclones

Subclones were again subjected to testing via ELISA (described below) incorporating an additional urine from a patient diagnosed as TCC+. Typically all subclones of a given original-evaluated well showed similar binding patterns and levels. Those showing loss of antibody production in all subclones were discarded, while those displaying loss in any examined subclone were subjected to another subcloning. This was repeated until all subclones showed comparable levels of expression. Nomenclature for each level of subcloning consisted of appending to the clone designation a period followed by the number of the selected subclone.

F. Assays

The titer assay was carried out by coating Pool II (Example I.A., above) antigen adjusted to 4 μg/mL in 0.1 M carbonate buffer, pH 9.6, directly to polystyrene plates. Each well received 50 μl of coating solution and the plate was covered and incubated at 37° C. for 2 hours, after which time it was washed twice with phosphate buffered saline (PBS) in a Denley strip well washer. The plate was blocked by the addition of 100 μl of a 1% gelatin hydrolysate, 2% sucrose solution in 50 mM Tris-HCl, pH 7.5, at 37° C. for 1 ½ hours (all reagents from Sigma). Following blocking, the plate was again washed twice with PBS, then two-fold serial dilutions of mouse serum, starting at 1:100, into 10% normal horse serum in PBS, were added row-wise to the plate at 50 μl per well. The plate was incubated at 37° C. for 1 hour, washed 4 times in PBS, and 50 μl of affinity purified goat anti-mouse IgG- horseradish peroxidase (HRP) conjugate (Tago, Burlingame, Calif.) diluted 1:5000 in 10% horse serum in PBS added to each well. This was allowed to incubate for 1 hour at 37° C. The plate was washed with PBS 4 times, and 50 μl of substrate (K-Blue, ELISA Technologies, Lexington, Ky.) was added and the plate allowed to develop for 10 minutes at room temperature before stopping the reaction via the addition of 100 μl of 2M phosphoric acid solution in water (Sigma). The optical density of the wells were read at 450 and at 410 nm in a BioTek EL311 plate reader. Readings which were off scale at 450 nm were calculated from the corresponding reading at 410 nm by the method of Madersbacher and Berger, *J. Immunol. M.* 138:121–124, 1991.

The fusion was screened for antibody production by use of the following fusion screen. Antibody binding was tested with: (a) two clinically diagnosed patient urines, stages T2III and T3III , (diluted 1:80), (b) two pools of normal human urines (diluted 1:15), (c) human type IV collagen (diluted to 4 μg/mL), all dilutions in 25 mM Tris-HCl, and (d) pooled human red blood cells (Gamma Biologicals, Houston, Tex.) diluted into PBS and coated onto poly-lysine coated plates. All plates were blocked by washing with PBS with 0.1% Tween-20, and by the dilution of the media samples 1:5 into complete IMDM containing 10% FBS. Supernatant fluid (70 μL) of the wells chosen for screening were transferred to a well of a 96 well plate. To each well, 280 μl of diluent was added, and 50 μl was distributed to the test plate wells. The remaining steps of the assay were as for the titer assay, with the exception that the conjugate used was human serum adsorbed goat anti-mouse IgG-HRP conjugate (Kirkegaard and Perry Labs (KPL), Gaithersburg, Md.) diluted 1:5000 in 10% normal goat serum in PBS for all except the RBC plates. For the latter, an alkaline phosphatase conjugate of a similar antibody was used (KPL, Gaithersburg, Md.) followed by use of PNPP (p-nitrophenyl phosphate) substrate. Controls were used for each assay, negative control was fresh IMDM with 10% FBS, positive controls were monoclonal anti-human collagen (Sigma C1926), and monoclonal anti-hIgA (A1.1.2.4, Bard Diagnostic Sciences, Inc., Redmond, Wash.), both of which showed high binding to all test antigens except the red blood cells. Criteria for selection were high binding to cancer urine plates (OD>1), low binding to normal urines and other test antigens (OD<0.5). Others which showed high antibody levels in different patterns with respect to the test antigens were also selected for potential research uses.

Subclones were screened by several assays. First, the fusion assay was again used then, following expansion in culture of selected subclones, an abbreviated ELISA was employed using normal urine pool I and the two advanced stage urines used in the fusion assay. The testing was carried out at dilutions of 1:10 and 1:100 for the early subclones, and an additional dilution of 1:1000 for the later subclones. In several of the subclone assays the addition of urine from a patient with a lower grade cancer was included.

From the 9,312 wells plated in the fusion, a total of 880 wells showing growth were screened, with a total of 94 X series and 24 I series clones selected for further work.

Analysis of the fusion via Poisson distribution, suggested that there was a 4.6% probability that any well showing growth contained 2 or more clones, or 5 to 6 of the total clones being multiclonal. Of the 118 clones selected, 37-X and 8-I series were eventually lost due to instability or lack of growth without feeder cells.

A total of 32 subclones were selected based on selectivity of antibody binding to cancer positive urines versus the normal urines and on retention of assay OD with dilution of culture supernatant to select for high affinity and good production level. Samples of spent culture media from the following clones were evaluated for their potential utility in a clinical assay for the antigen described in Example III: I-7.3, I-8.2, I-10.2, I-11.1, I-12.2, I-17.3, X-4.1, X-13.1, X-13.2, X-22.2, X-28.1, X-44.1, X-49.1, X-49.2, X-50.3, X-52.1, X-53.2, X-55.1, X-56.3, X-59.1, X-60.2, X-61.2, X-62.1, X-63.2, X-64.3, X-67.2, X-69.1, X-70.2, X-84.2, and X-87.2. A preferred monoclonal antibody pair for assays is X-13.2 (conjugate MAb) and X-52.1 (capture MAb).

Example II

DEVELOPMENT OF GOAT POLYCLONAL ANTIBODIES

A. Goat Immunization

1. Antigen

Heparin-Agarose chromatography (Example I.A., above) fractions from three TCC-positive patients were pooled and dialysed against phosphate buffered saline (PBS). Protein concentration was determined to be 2 mg/mL. Thimerosal was added to a final concentration of 0.02%, and 0.25 mL aliquots were frozen until use. Table 1 is a listing of the amounts and references of the antigens comprising Pool I.

TABLE 1

Antigen Pool I

| Patient ID | Date of Sample | Fractions | Protein Conc. | Volume Used |
|---|---|---|---|---|
| 1 | 3/29/94 | 13–31* | — | — |
| 1 | 3/30/94 | 14–30* | 3.2 mg/mL* | 0.5 mL |
| 2 | 6/6/94 | 11–19 | 0.91 mg/mL | 1.5 mL |
| 3 | 6/8/94 | 11–24 | 3.6 mg/mL | 0.7 mL |

*both sets of fractions were combined before protein determination.

2. Immunization

For immunization, a vial of antigen was thawed and mixed. An aliquot of 0.125 mL of antigen was mixed into 0.75 mL of PBS, and drawn into a 5 mL glass syringe. This syringe was attached to another such syringe containing 1 mL of Difco Freund's adjuvant, via a double-hub emulsifying needle. The first immunization was with Freund's Complete adjuvant, all others were with Freund's incomplete adjuvant. The emulsion was formed by alternately forcing the total mixture from one syringe to the other. The stability of the emulsion was tested by removing one syringe from the needle and dipping the end into a beaker of tap water. If a small amount of emulsion expressed into the water did not immediately spread over the surface, the emulsion was deemed stable. The entire amount of emulsion was collected into one syringe, which was capped and stored on ice until used. Total protein in the inoculum was 0.25 mg.

Goats (R & R Rabbitry, Inc., Stanwood, Wash.) were 5 ½ months of age and weighed approximately 34 kg. when the first immunization was administered. The second and third immunizations were given thirty and sixty days later.

B. Antibody Analysis

Serum samples were taken pre-immunization and two weeks after the second and third immunizations and were analyzed via ELISA using the antigen coated onto microplates. The assay was similar to the ELISA used for the mouse serum titer with the exception that antigen Pool I and rabbit anti-goat IgG-HRP were used and the dilution range employed was from $6 \times 10^3$ to $1.861 \times 10^6$.

The results of the assay were the following:

1. Pre-immunization sample showed no antibody titer as expected.
2. Samples after the second and third immunizations showed a maximal OD at about $3 \times 10^3$ dilution, a half maximal signal at about $8 \times 10^4$ and background at $1 \times 10^6$. The signal at a dilution of $1 \times 10^5$ was 1.4.
3. In another experiment, cross reactions were tested and rated on a scale of 0 to 4 at a serum dilution of $1 \times 10^5$, and were as follows in Table 2, with 4 being highest OD:

TABLE 2

| | |
|---|---|
| human Collagen Type IV | 0 |
| human Fibronectin | 1 |
| human Laminin | 0 |
| human Fibrinogen | 1 |
| Bovine submaxillary mucin | 0 |
| human red blood cells | 0 |
| Pool I | 4 |

(rabbit anti-goat IgG-alkaline phosphatase was substituted for the rabbit anti-goat IgG-HRP).

Example III

PURIFICATION AND CHARACTERIZATION OF ANTIGEN

A. Purification

1. Heparin-Agarose Chromatography of Urine

Twenty-four hour urine samples were centrifuged in a Beckman centrifuge, Model #J2-21, S/N 5539, using a JA-10 rotor at 6,000 rpm for 20 minutes. The clarified urine sample was then concentrated using an Amicon stirred cell, 76 mm, (cat# 5124) fitted with a YM30 membrane MWCO 30,000 daltons (Amicon, cat# 13742) or a Microgon hollow fiber concentrator, 50,000 MWCO (cat# M15S-260-01N) to approximately 100× concentration. The concentrated sample was diluted 1:1 with 25 mM Tris-HCl, pH 7.4, and loaded onto a column of Heparin-Affigel (BioRad, cat# 153–6173), equilibrated in 25 mM Tris-HCl pH 7.4, at a flow rate of 2.0 mL/min. The sample was followed with equilibration buffer until the $A_{280}$ elution profile returned to background. Bound material was eluted with a 100 mL, linear NaCl gradient from 0 to 250 mM NaCl in 25 mM Tris-HCl, pH 7.4, followed by 50 mL of 250 mM NaCl, 25 mM Tris-HCl, pH 7.4, and finally 20 mL of a 10× PBS, pH 7.4, solution. Five mL fractions were collected and fractions from the trailing half of the elution peak were pooled. Pooled fractions were concentrated with an Amicon stirred cell, 43 mm (cat# 5122), fitted with a YM30 membrane, MWCO 30,000 daltons (cat# 13722).

2. Protein A Chromatography of 24 Hour Urine

Protein A Chromatography was performed on a 24 hour urine from a TCC+ patient to determine whether this tumor antigen could be part of an immune complex. The urine (6 mL) was diluted to 12 mL with the addition of 6 mL of 20 mM sodium phosphate, pH 7.4. The diluted urine (7.3 mL) was loaded on a 1.0 mL Protein A cartridge (BioRad, Richmond, Calif., cat# 732-0093) equilibrated in 20 mM sodium phosphate, pH 7.4, at 0.5 mL/min. The flow through volume plus 5.0 mL of wash buffer was collected and labeled as "flow through" (total volume=12.3 mL). Bound material was eluted with 100 mM citrate buffer, pH 3.0, and neutralized immediately with the addition of 100 μl of a 1.0 M Tris-HCl, pH 8.0, to each 3 mL fraction. Eluted antigen was pooled (~6 mL) and the sample load, flow through, and eluted pool, at dilutions of 1:20 to 1:2560, were tested in the double monoclonal microtiter plate assay described in detail below (Example IV.B.). Approximately 97.5% of the activity loaded was contained within the flow through peak. The 2–3% activity in the eluted pool was probably due to incomplete washing. Thus, this antigen is not part of an immune complex involving IgG, and the use of immobilized Protein A would not be effective in extracting the antigen from specimens.

3. MAb 13.2 and MAb 52.1 Affinity Chromatography of 24 Hour Urine

Aliquots of 24-four hour urines were diluted 1:1 with 25 mM Tris-HCl, 250 mM NaCl, pH 7.4, and loaded onto 5 mL MAb affinity columns (BioRad A10 gel) prepared with MAb X-13.2 or MAb X-52. 1 (Example I.F.). To serve as a control for urine materials binding non-specifically to IgG, an A10 control column was prepared using Protein A-purified, normal mouse serum. Samples were loaded at 0.5 mL/min. The sample was eluted with 25 mM Tris-HCl, 250 mM NaCl, pH 7.4, until the OD280 baseline was reached. The bound material was then eluted with 100 mM glycine-HCl, pH 3.0. The eluted fractions, 5 mL each, were collected in tubes containing 100 μl of 1.0 M Tris-HCl, pH 8.0. Purity was assessed by SDS-PAGE using Novex 8–16% and/or 4–12% polyacrylamide gels under reducing and non reducing conditions, along with Novex (San Diego, Calif.) Mark XII molecular weight standards (6 to 200 kD). The gels were stained with Coomassie Blue R250 followed by silver staining and scanned using a BioRad GS7000 densitometer. Molecular weights of individual bands are estimated based on the Rf values of the molecular weight standards (Example III.C.).

B. Native Molecular Weight Estimation of the Antigen by Gel Filtration

A gel filtration column was prepared with Pharmacia Sephacryl S-300 (Pharmacia, Piscataway, N.J., Cat# 17-0599-01). Briefly, deionized water is added to S-300 gel to form a 50% slurry and added to a 1.0 L vacuum flask. The slurry was degassed by gently swirling the slurry while pulling a vacuum. The degassed gel was then poured into a 2.6×100 cm, Pharmacia XK glass chromatography column (cat# 19-0147-01) and packed at a 4.0 mL/min flow rate. The column bed was then equilibrated with 10 to 20 volumes of PBS containing 0.05% sodium azide and fitted with a Pharmacia column flow adapter (cat# 19-0688-01).

A set of gel filtration standards (BioRad cat# 151-1901), with a range of 1.3 to 670 kD was dissolved in column equilibration buffer (PBS), filtered through a 0.45 μm Acrodisc, and loaded onto the column at 0.7 mL/min. The elution profile of the absorbance at a 280 nm wavelength was recorded at 2.0 cm/hr. A high molecular weight aggregate eluted at the column void volume (Vo). Each protein peak had its elution volume (Ve) determined by multiplying the time of elution of the maximum absorbance by the flow rate. A linear calibration curve was generated by graphing the Ve/Vo of the standard proteins vs. the logs of their molecular weights. Molecular weight estimates of the samples' peaks were made using the linear equation generated by the calibration curve.

A twenty-four hour urine from a TCC+ patient was concentrated using an Amicon stirred cell, fitted with a 43 mm, YM30 membrane (MWCO 30,000 dalton) (cat# 5122). The urine was concentrated 300× to ~0.5 mL and loaded onto the XK S300 column at 0.7 mL/min and 7 minute fractions were collected. The individual fractions were tested in the double monoclonal assay (described in Example IV.B.) to detect the presence of the antigen. A range of native molecular weights for the active fractions was calculated as 267 kD to 395 kD.

C. Subunit Molecular Weights of the Components of Affinity-Purified Antigen by SDS-PAGE MAb X-13.2.1 affinity purified urine antigen (Example III.A.3.) was applied, in the presence or absence of dithiothreitol (DTT; reducing sample buffer), onto a Novex discontinuous, 8% polyacrylamide, two well gel. A reference well contained Novex Mark XII SDS-PAGE molecular weight (MW) standards. Gels were electrophoresed at 125 V constant until the sample front reached within ~0.5 cm of the bottom of the gel. The gel's protein bands were then transferred to PVDF and stained with Coomassie Blue R250.

Rf values were calculated for the Mark XII individual molecular weight standards by dividing the distance the band moved through the resolving gel by the distance of the sample front from the top of the resolving gel. A linear standard curve was established by plotting Rf values versus log MW for each MW standard. Sample bands' molecular weights were estimated by calculating their Rf values and entering these values (yi) in the standard curve equation.

Immobilized MAb X-52.1 bound approximately 10 components with apparent molecular weights 151, 130, 87, 77, 60, 49, 39, 29, 25, and 10 kD under reducing conditions (i.e., in the presence of DTT). Only bands at 151, 130, and 39 kD appeared to be specific for the MAb X-52.1 in that the other proteins also bound to immobilized non-specific mouse IgG. Of these bands, that corresponding to a molecular weight of 151 kD is typically the most intensely staining. In contrast, immobilized MAb X-13.2 affinity purified fractions were generally cleaner than those obtained with immobilized MAb X-52.1, containing predominant bands at 151, 130, and 39 kD with only very minor contaminant bands at 77, 60, and 25 kD. Under non-reducing conditions, the monoclonal antibody-specific bands exhibited apparent molecular weights of approximately 138 kD, 121 kD, and 40 kD, with the 138 kD band being typically the most intense. The shift in apparent molecular weights of the dominant band from 138 kD to 151 kD upon reduction and the 121 kD band to 130 kD upon reduction could be due to the presence of a large number of intra-chain disulfide bonds in these molecules. This characteristic electrophoretic behavior formed the basis for the antigen assay described in Example IV.F.

D. Western Blot Analysis of Partially Purified Antigen Preparations

The urine samples purified on Heparin-Agarose (Example III.A.1.) were diluted 1:2 with SDS-PAGE 2× Sample Buffer (Novex, cat# LC 2676) in the presence dithiothreitol and heated at 100° C. in a boiling water bath for 5 minutes, then allowed to cool to room temperature. The sample preparations were loaded onto an 8–16% acrylamide, 1.0 mm thick, 10-well, discontinuous Novex SDS-PAGE gel (Novex, San Diego, Calif., cat# EC6045) and electrophoresed at 125 V constant for 190 V-h using a Novex electrophoresis chamber (Novex, cat# EI9001) and a BioRad Power Unit 500 V (cat# 165-4710). Novex SeeBlue Molecular Weight Standards (cat# LC5625) were loaded into a reference well. The SDS-PAGE bands were transferred to PVDF paper (Novex, cat# LC2002) in Novex Transfer buffer (cat# LC 3675) using a Novex Transfer apparatus (Novex, cat# EI19051) and BioRad 500 power supply at 125 mA constant for 60 minutes.

The PVDF paper was blocked with PBS containing 2% non-fat dry milk solution for 60 minutes, washed with PBS, containing Tween-20 (0.05%). MAbs are diluted in PBS-Tween to 2 μg/mL were added to the PVDF paper for 2 hours, washed with PBS-Tween, and incubated with an anti-mouse IgG alkaline phosphatase conjugate for 1 hour. The PVDF was washed with 50 mM Tris containing 5 mM $MgCl_2$ and then a NBT/BCIP substrate solution was added in the 50 mM Tris-5 mM $MgCl_2$ solution and the bands were developed.

MAb 13.2 showed three major bands at 138, 121, and 40 kD. MAb 52.1 recognized the same bands, but reacted with the 40 kD band to a greater extent and with the 121 kD band to a lesser degree than MAb X-13.2.

E. Amino Acid Sequence Determinations

1. N- Terminal Amino Acid Sequence

A 450 mL pool of three urines was initially chromatographed on a Heparin-Affigel column (2.5×16 cm), as described in Example III.A.1. The antigen containing fractions were eluted with 100 mM NaCl in 25 mM Tris-HCl buffer, pH 7.4, were pooled and 50 mL at 265 μg/mL was loaded directly onto a monoclonal affinity column, 2 mL, prepared with MAb X-13.2.1 (Section II.F.) and Affigel 10 (BioRad, cat# 153–6099). The bound antigen was eluted with a 100 mM sodium citrate, pH 2.5, and immediately neutralized with a 1.0 M Tris-HCl buffer, pH 8.0.

The MAb affinity purified antigen was diluted 1:1 with SDS-PAGE 2× Sample Buffer (Novex, cat# LC 2676) containing 2% DTT and heated at 100° C. in a boiling water bath for 5 minutes, then allowed to cool at room temperature. The sample preparation was loaded onto an 8% acrylamide, 1.0 mm thick, 2-well, discontinuous Novex SDS-PAGE gel (Novex, cat# EC6012) and electrophoresed at 125 V constant for 190 V-h using a Novex electrophoresis chamber (Novex, cat# EI9001) and a BioRad Power Unit 500 V (cat# 165-4710). BioRad SDS-PAGE Molecular Weight Standards (cat# 161-0317) were loaded into a reference well.

The gel was removed and placed in a container of 10 mM CAPSO buffer, pH 9.0, containing 0.05% SDS on a rocker platform while the gel transfer sandwich was prepared. The SDS-PAGE bands were transferred to PVDF membrane (Novex, cat# LC2002) using a Novex Transfer apparatus (Novex, cat# EI9051) and BioRad 500 power supply at 125 mA constant for 60 minutes. The PVDF membrane was removed and rinsed with deionized water and stained in a 0.1 % Coomassie Blue R-250 in 20% methanol protein staining solution for approximately 10 minutes. The stained PVDF was then destained with several changes of 30% methanol until the background stain was minimal, and was followed by extensive washing in deionized water. The PVDF membrane was then allowed to dry at room temperature on a paper towel. The stained bands of interest were excised with a clean razor blade and placed in capped tubes. The samples were carried to the University of Washington (Seattle, Wash.) for sequencing by Edman degradation. The principal amino acid sequence thus obtained was: EDCN-?LPPR?NT(SEQ ID NO: 1), where the symbol "?" indicates a residue which could not be identified.

2. Trypsin Digestion: Internal Amino Acid Sequence

A small amount (50–100 μL) of immobilized trypsin (Pierce Chemical Co., Rockford, Ill.) was added to a 600 μL Eppendorf tube along with an equal volume of PBS. After gentle mixing, the slurry was spun down at 10K rpm for about 30 seconds. The supernatant solution was pipetted off and two times the slurry volume of PBS was added, mixed and the spin repeated. This wash step was repeated twice more and the slurry brought back to the original volume with PBS.

A known quantity of antigen was added to a clean 600 μL Eppendorf tube and PBS added to bring the concentration to 0.5 mg/mL. Immobilized trypsin was added in a 1:10 E/S ratio (w/w), and the solution was gently mixed and placed on a rotator for four hours at room temperature (21–23° C. ).

Digestion patterns were visualized by SDS-PAGE using a 4–12% gradient Tris-Glycine precast gel with Tris-Glycine SDS running buffer (NOVEX, San Diego, Calif.). Samples were mixed with the appropriate amount of 4× sample load buffer, containing 4% dithiothreitol (ACS grade reagent), boiled for two minutes and then loaded on the gel. Gels were run for 240 Vhr at 125 volts constant, stained in 0.01% Coomassie R250 (BioRad, Hercules, Calif.,) in 10% acetic acid, 50% methanol for an hour and destained in 10% acetic acid, 50% methanol for about 20 minutes. Gels were transferred into water for one hour, into GelDry solution (NOVEX, San Diego, Calif.) for twenty minutes and then dried in between two sheets of DryEase mini precut cellophane (NOVEX, San Diego, Calif.) overnight. Seven fragments were observed.

Material for sequencing was prepared by digestion with trypsin as described above. Approximately 300 μg of urine antigen was digested, boiled in 1/3 volume load buffer with 4% DTT and electrophoresed on a 10% Tricine gels (NOVEX, San Diego, Calif.). The gels were rinsed (about 1–2 minutes each time) in three changes of 10 mM CAPS (Sigma Chemical Co., St. Louis, Mo.) containing 10% methanol (ACS grade reagent), pH 11.0 (blotting buffer) to remove any contaminants from the gels. The proteins were transferred onto PVDF membranes (NOVEX, San Diego, Calif.) by electroblotting in blotting buffer at 30 V constant for 1.0 hour. After blotting, the membranes were washed once with fresh blotting buffer and then stained for two minutes with 0.1% Coomassie R250 in 10% acetic acid containing 50% methanol. The blots were destained in 10% acetic acid with 50% methanol for approximately 15 minutes, rinsed three times with deionized water and then air dried. Stained portions of the blots were excised, placed in 15 mL conical tubes and stored at −20° C. until sequenced.

Sequencing was performed at the laboratory of Dr. Ken Walsh, Department of Biochemistry, University of Washington (Seattle, Wash.), and the results are shown in Table 3. Residues tentatively assigned by the operator appear in parenthesis and unassignable residues are indicated by a question mark.

TABLE 3

Sequences of Urine Antigen Tryptic Fragments

| Sample [1] | Fragment (~MW) | Sequence | SEQ ID |
|---|---|---|---|
| 1 | 128 kD | GPYFPVAVGKYY?(Y)Y?D | NO:(2) |
|  | sequence starts at CFH AA 324 | [RPYFPVAVGKYYS Y YCD] | (NO:12) |
| 2 | 79 kD | RPYFPVAVGKYYS?Y?DE?F???S | NO:(3) |

TABLE 3-continued

Sequences of Urine Antigen Tryptic Fragments

| Sample [1] | Fragment (~MW) | Sequence | SEQ ID |
|---|---|---|---|
|  | sequence starts at CFH AA 324 | [RPYFPVAVGKYYSYYCDEHFETPS] | (NO:13) |
| 3 | 46 kD | SSQESYAHGTK | NO:(4) |
|  | sequence starts at CFH AA 868 | [SSQESYAHGTK] | (NO:4) |
| 4 | 37 kD | EDCNELPP?RNTEIL?GSW-D | NO:(5) |
|  | sequence starts at CFH AA 1 | [EDCNELPPRRNTEILTGSWSD] | (NO:14) |
| 5 | 66 kD | RPYFPVVAVGKYYSYY?DEHFE?P | NO:(6) |
|  | sequence starts at CFH AA 324 | [RPYFP-VAVGKYYSYYCDEHFETP] | (NO:15) |
| 6 | 33 kD | [2]SLGNVIMV?RKGEWVALNPLRK | NO:(7) |
|  | sequence starts at CFH AA 40 | [SLGNVIMVCRKGEWVALNPLRK] | (NO:16) |
|  | sequence starts at CFH AA 324 | [3]RPYFPVAVGKY | NO:(8) |
|  |  | [RPYFPVAVGKY] | (NO:8) |

[1]Amino acid residue numbers refer to the mature CFH molecule
[2]Major protein sequence
[3]Minor protein sequence The similarity of the partial amino acid sequences of the antigen with those of the reported sequence for human complement Factor H (shown in brackets) demonstrates that the antigen detected is a member of a complement Factor H-related family of proteins as disclosed herein.

F. C3b—Decay Accelerator Activity of the Antigen

C3b was prepared from C3 (Sigma Chemical Co., St. Louis, Mo.) by trypsin digestion, using immobilized trypsin (Pierce Chemical Co., Rockford Ill.), and an enzyme to substrate (E/S) ratio of 1:25 at room temperature for fifteen minutes. The digest was spun at 10k rpm for about 30 seconds to pellet the enzyme, and the supernate removed. The supernate was checked for the presence of C3b by SDS-PAGE under reducing conditions.

Five $\mu$g each of affinity-purified antigen from either urine or serum, 5 $\mu$g Factor I (Sigma Chemical Co., St. Louis, Mo.) and 50 $\mu$g C3b (Sigma Chemical Co., St. Louis, Mo.) were incubated with gentle mixing at 37° C. for 90 minutes. Six $\mu$l of undiluted, dialyzed patient urine samples, 3 $\mu$l Factor I (FI) and 30 $\mu$l C3b were incubated as described above in a separate experiment. A small portion of each reaction mixture was boiled for two minutes with 1/3 volume 4× load buffer, 4% DTT and loaded onto a 4–12% Tris-Glycine gradient gel. Gels were run for 240 Vhr at 125 volts constant, stained in 0.01% Coomassie R250 in 10% acetic acid, 50% methanol for an hour and destained in 10% acetic acid, 50% methanol for about 20 minutes. Gels were transferred into water for one hour, into GelDry solution (NOVEX, San Diego, Calif.) for twenty minutes and dried between two sheets of DryEase mini precut cellophane (NOVEX, San Diego, Calif.) overnight.

The dried gel was analyzed with a BioRad Model GS-700 Imaging Densitometer equipped with BioRad's Molecular Analyst software and the molecular weights of the digestion fragments were estimated using Mark12 molecular weight markers as standards.

The disappearance of the C3b α' fragment at a molecular weight of 108,000 daltons and the concurrent appearance of fragments with molecular weights of 67,000, and 47,000 daltons indicate the digestion of C3b by Factor I. This digestion only occurs when mediated by a cofactor molecule, such as Complement Factor H, as was apparent in the control runs. For example C3b, when incubated with Factor I alone, does not degrade. Urine affinity purified antigen mediated the digestion of C3b by Factor I, indicating that this antigen has a functional C3b binding site and acts as a cofactor in the digestion of C3b by Factor I. TCC[+] urine samples also functioned as cofactor for the digestion of C3b by Factor I, while a normal urine sample did not.

Example IV

ASSAYS FOR THE ANTIGEN

Given the characteristics of the antigen as described above and given the disclosure herein for generating and selecting antibodies and the development of certain assays described herein to detect the antigen, a number of additional assay formats beyond those described herein for this antigen may be readily developed by those of ordinary skill in the art. Suitable assay formats include competitive formats, sandwich formats (Examples IV.A., IV.B. and IV.C), assays based on the biological or chemical properties of the antigen (Example IV.D. and IV.E.), assays based on the simultaneous binding of the antigen to a specific macromolecule (e.g., C3b) and to a monoclonal antibody (Example IV.D.), assays based on the appearance of a band of appropriate size in partially-purified specimens (Example IV.F.), and RT-PCR (Example IV.G.). A preferred format involves sandwich immunoassays and the most preferred employs a monoclonal antibody immobilized on a solid surface and a second monoclonal antibody, which recognizes an epitope distinct from that of the first, conjugated to a detection agent. That detection agent could be an enzyme (Example IV.B.), colloidal gold (Example IV.C.), or any of a number of other such agents known to those of ordinary skill in the art. These include fluorescent molecules, radioisotopes, and biotin (which would subsequently bind to avidin or strepavidin-labeled detecting agent).

A. Identifying Potential Antibody Pairs

Definitions for the section:

Indirect Assay Format: Antigen coated on plate; reaction with MAb; signal generation by Goat Anti-mouse conjugated to alkaline phosphatase (GAM-AP).

Direct Assay Format: Antigen coated on plate; reaction with and signal generation by specific MAb-AP.

Sandwich Assay Format: As usual

Initial screening of the cell culture supernatants (Example I.F.) was carried out using an ELISA in an indirect format. The assay consisted of the following in order: (1) diluted urine samples were adsorbed on a microtiter plate; (2) following washing, the microtiter plate wells were incubated with supernatants of cell cultures of the clones of interest; (3) following another wash, the plates were incubated with alkaline phosphatase-conjugated goat anti-mouse IgG; (4) following a final wash, the plates were incubated with p-nitrophenyl phosphate substrate (pNPP); and, finally, (5) the reactions were stopped by addition of concentrated EDTA to each well and the color measured at a wavelength of 410 nm on a microplate reader.

Cell culture supernatants from 32 different clones (Example I.F.) were tested against single dilutions of urine samples in the first stage of screening of this nature. The urine samples used during this first stage consisted of eight from normal individuals and eight from individuals with transitional cell carcinoma of the bladder (TCC) of various stages and grades. Still using the indirect format, supernatants from 23 clones which showed acceptably low reactivity with the normal samples (specificity=7/8 or 8/8) and generally positive reactivity with the TCC urine samples (between 6/8 and 8/8) were then further tested against serial dilutions of eight urine samples from patients with TCC of various stages and grades. Based on their behavior in this experiment with serially diluted urine samples adsorbed to the plates, twelve were selected for further study. In this experiment, plates were prepared with fixed dilutions of eight urine samples and serial dilutions (between 1/10 and 1/1280) of each of the antibodies were applied. All twelve of these showed sufficiently high reactivity that the eight TCC-positive samples were serially diluted and again assayed. The final experiment using the assay in the indirect format consisted of testing the twelve cell culture supernatants against twelve TCC-positive urine pools. Based on these initial experiments in the indirect format, all twelve antibodies were selected for further testing/screening utilizing the sandwich format of the assay.

Initial testing of antibodies conjugated to alkaline phosphatase (AP), as described in Example IV. B. 2., was carried out utilizing an assay in the direct format as follows: (1) diluted urine samples were adsorbed on a microtiter plate; (2) following washing, the plates were incubated with AP-conjugated antibodies from specific clones; (3) following a final wash, the plates were incubated with pNPP; and, finally, (4) the reactions were stopped and measured as above. Based on the results obtained from seven conjugates tested on a small number of urine samples in this manner, all seven were selected for further study in the sandwich format of the ELISA.

Thirteen monoclonal antibodies (Example I.F.) and one goat polyclonal preparation (Example II) were tested as capture antibodies in combination with the seven alkaline phosphatase conjugates in the sandwich ELISA format as follows: (1) individual capture antibodies were adsorbed on microtiter plates; (2) following washing, diluted urine samples were added to the wells and incubated to allow binding of the antigen to the antibody; (3) following another wash, single conjugates (as described in B above) were added to individual wells and incubated to allow binding to the antibody-bound antigen, if present; (4) following a final wash, the plates were incubated with pNPP; and, finally, (5) the reactions were stopped and measured as above. A total of 107 potential antibody pairs were first tested against one normal and seven TCC-positive urine samples. From these, a selection of 33 pairs were chosen to be tested against an expanded series of urines from 31 patients and one normal individual. From the results of this testing, seven antibody pairs were selected for further testing against a much expanded selection of 120 patient urine samples, but including also 20 samples from normal individuals. From this extensive testing of these seven pairs, a single monoclonal antibody pair (X52.1/X13.2-AP) was selected as the most preferred on the basis of (1) its positive response with the greatest number of samples from TCC-positive patients, (2) its negative response with the greatest number of samples from non-TCC-positive patients, and (3) low nonspecific reaction with urine samples from normal, non-diseased individuals. In addition, an alternative antibody pair was selected (X52.1/X62.1-AP).

B. Sandwich ELISA

The sandwich ELISA, utilizing the most preferred pair as selected above, was further optimized with respect to the following items: (1) coating level of capture antibody; (2) concentration of conjugate; (3) enzyme-to-antibody ratio in the conjugate; (4) reaction kinetics/incubation times; (4) composition of assay and wash buffers and of conjugate and specimen diluents; and (5) formulation of standards and controls. The assay as optimized is performed as follows:

1. Preparation of Coated Plates

The plates were coated with 150 $\mu$l per well of monoclonal antibody at a concentration of 5 $\mu$g/mL in carbonate buffer at pH 9.6. The plates were then blocked with 2% bovine serum albumin in phosphate-buffered saline at pH 7.4, followed by blocking with 4% sucrose. The sucrose solution was decanted, and the plates were dried overnight at room temperature.

2. Preparation of MAb-Alkaline Phosphatase Conjugates

Antibodies were purified by chromatography on immobilized Protein G or Protein A by standard techniques. Although antibody-enzyme conjugates could be prepared using a variety of coupling techniques (for review see Scouten, W. H., *Methods in Enzymology* 135:30–65, 1987), a minor variation of a method described by S. Hashida and E. Ishikawa (*Anal. Lett.* 18, B9:1143–1155, 1985) was used. Briefly, purified monoclonal antibodies were treated with excess N-acetylhomocysteine thiolactone (AHTL) at neutral pH to introduce reactive thiol groups, and then desalted to remove excess AHTL. Separately, alkaline phosphatase (AP) was treated with excess sulfosuccinimidyl 4-(N-maleimido-methyl) cyclohexane-1-carboxylate to introduce maleimido groups, and excess reagent was removed by desalting. The conjugates were prepared by mixing antibody and enzyme derivatives, which became covalently coupled via thioether bonds. Any excess maleimido groups were then capped by reaction with cysteamine.

3. Assay Format

A volume of 175 $\mu$l of assay buffer was pipetted into each well to be utilized in carrying out the assay. The buffer was followed by 25 $\mu$l of samples, standards, or controls, thus yielding a 1/8 dilution in the well. Incubation of the covered plate was performed at 37° C. for 60 minutes. Following washing, 200 $\mu$l of working dilution of conjugate was added to the aspirated well. The covered plate was again incubated for 60 minutes at 37° C. Following a final wash, 200 $\mu$l of pNPP substrate was pipetted into each well, and the covered plate was incubated at 37° C. for 30 minutes. After pipetting, 50 $\mu$l of stop solution into each well, the reaction mixtures in each well were measured at 410 nm.

4. Typical Results

Eighty seven urine samples were assayed by the ELISA using the format described above. These samples included 23 clinical specimens taken from patients diagnosed as currently having transitional cell carcinoma (TCC) and 64 others. The results are tabulated below in Table 4. Sensitivity is reported as the percentage of specimens from TCC-positive patients that correctly produce a positive result in the assay. Specificity is reported as the percentage of urines from individuals without TCC that correctly produce a negative result in the assay.

TABLE 4

|  | Number of Specimens | Percentage of Total |
|---|---|---|
| Sensitivity | 23 | 48% |
| Specificity |  |  |
| Healthy | 25 | 88% |
| Non-GU Disease | 15 | 87% |
| GU Malignancy | 3 | 100% |
| Other GU Disease | 10 | 70% |
| Chronic Inflammation (Urinary Tract) | 11 | 27% |

A graphical representation of the data for each specimen, expressed as Units of analyte/mL, is shown in FIG. 9. (Note that the categories correspond to those specified in the above table and that GU=Genitourinary.)

It is clear that the ELISA described here for the detection of this tumor antigen yields a positive reaction with a significant number of urine specimens taken from patients diagnosed with bladder TCC. Samples which yield negative results, although taken from TCC-positive patients, correspond to those with disease at an early stage and/or of low grade. With respect to those patients identified as having chronic inflammation, several have a history of TCC.

C. Rapid Assay

Monoclonal antibodies specific for the antigen (Example I.F.) were utilized in a lateral flow format to produce a qualitative assay for bladder cancer using urine as the specimen. The lateral flow format consisted of a colloidal gold antibody conjugate and an immobilized capture antibody on a nitrocellulose membrane. Upon interaction of the urine sample with the colloidal gold conjugate, the antigen in the urine sample formed an antigen-antibody conjugate complex. This complex migrated by capillary flow through the membrane and contacted the immobilized anti-antigen capture antibody (test zone). The capture antibody bound the antigen-antibody conjugate complex, forming a visually detectable colored signal in the test zone. Material not bound by the capture antibody continued to migrate through the membrane and contact an immobilized goat anti-mouse antibody (control zone) which bound the colloidal gold conjugate regardless of the presence of antigen, forming a visually detectable signal in the control zone.

Purified monoclonal antibody X-13.2 was conjugated to colloidal gold according to Frens (Frens, G., *Nature, Phys. Sci.* 241:20–22, 1973). Briefly, the gold sol was prepared by reduction of tetrachloroauric acid by trisodium citrate. The solution was boiled until a color change was observed. MAb X13.2 was adsorbed to the gold sol at 0.3 mg/ml for 5 minutes at pH 9. The conjugate was blocked with 0.5% BSA and washed twice with the conjugation buffer. The washed conjugate was then diluted 7-fold into 2% BSA with 50 mM Tris, pH 9, and 0.05% $NaN_3$. The washed conjugate was used to saturate strips (10.5×0.25 in.) of glass fiber mesh (Lydall, Hamptonville, N.C.). These conjugate strips were then dried overnight under reduced pressure at ambient temperature.

An airbrush sprayer was used to immobilize the capture and control antibodies on the membrane. Purified monoclonal antibody X-52.1 at 2 mg/ml was sprayed as a line onto a section of nitrocellulose membrane (8 μm pore size, 50 m×1 inch, Whatman, Fairfield, N.J.) approximately ⅜ in. from one edge of the membrane strip. A goat anti-mouse antibody (Chemicon, Temecula, Calif.) at 2 mg/ml was sprayed approximately ⅜ in. from the other edge of the membrane. The membrane was then dried overnight under reduced pressure at ambient temperature and cut into 10.5 in. strips.

Figure 10:
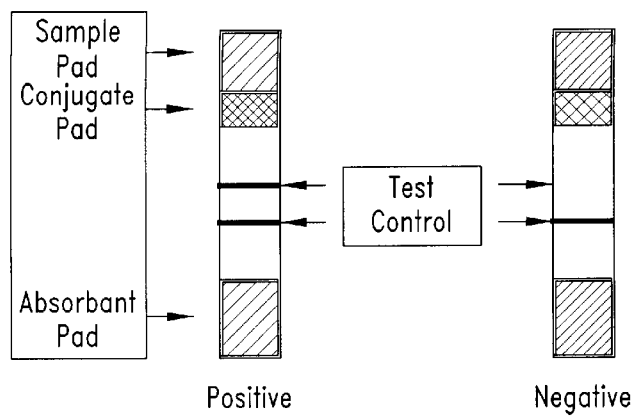
FIG. 10 shows the configuration of lateral flow assay components.

The 10.5 in. strips of coated glass fiber mesh and sprayed membrane were then assembled onto plastic cards (polypropylene, 10.5×2.25 in. ) using double-sided tape (below). The membrane was first placed near the center of the plastic card. The conjugate pad was then placed so as to overlap the membrane on the proximal side (near the x52.1 immobilized antibody) of the membrane and an absorbent cotton paper strip (Whatman, 10.5×0.75 in.) was placed so as to overlap on the distal side (near the goat anti-mouse immobilized antibody) of the membrane. Finally, a second absorbent cotton paper strip was placed in overlapping contact with the conjugate pad to accept the sample. The assembled cards were cut crosswise and the resulting small strips placed into plastic housings which provided a well for containment of the sample and a viewing window in the nitrocellulose region for reading the results. The configuration of lateral flow array components is shown in FIG. 10.

1. Results

Rapid assays were carried out by placing 250 μl of patient urine in the sample well. After 10 minutes, the results were read. A positive result will show a pink-purple line in the test zone (zone of immobilized X-52.1) and a pink-purple line in the control zone (zone of immobilized goat anti-mouse). A negative result will show no line in the test zone and a pink-purple line in the control zone. The absence of a line in the control zone indicates that the reagents in the test did not function properly and this test is invalid. Twenty three TCC-positive clinical specimens and 64 other urine specimens were assayed in the lateral flow assay. The results are given in Table 5 below. Sensitivity is reported as the percentage of TCC-positive specimens that correctly produced a positive result in the lateral flow assay. Specificity is reported as the percentage of TCC-negative urines that correctly produced a negative result in the lateral flow assay.

TABLE 5

| Sensitivity (23) | 65% |
|---|---|
| Specificity |  |
| Healthy (25) | 92% |
| Non-GU Disease (30) | 57% |
| GU Malignancy (3) | 100% |
| Other GU Disease (6) | 83% |

GU = Genitourinary

From Table 5 it is clear that the bladder cancer lateral flow assay detects a large percentage of the TCC-positive specimens tested and distinguishes bladder cancer (TCC) from other normal and disease states.

D. C3b-MAb ELISA

1. Method

Immulon 4 (Dynatech, Chantilly, Va.) microtiter strip wells were coated with 50 μl per well of 5 μg/ml trypsin treated C3 (converts C3 to C3b; see Example III.F. above for C3 source and method of activation) in 50 mM carbonate buffer, pH 9.6, either overnight at 4° C. or for two hours at 37° C. A control plate was coated with 50 μl per well of 2% BSA in PBS for two hours at 37° C. After a single wash with Tris-buffered saline (TBS) containing 0.1% Tween –20 (wash buffer), the plates were blocked with 100 μl per well of a 2% BSA solution in PBS for two hours at 37° C. and washed four times. Antigen, diluted in assay diluent (1% BSA in TBS with 0.15M $MgCl_2$, 0.15M $ZnCl_2$), was added at 50 μl per well and incubated for one hour at 37° C. The plates were washed four times and then the detection antibody (x13.2.1.1-alkaline phosphatase,) was applied at 0.25 μg/ml, 50 μl per well, and incubated at 37° C. for 30 minutes. After four washes, 50 μl per well of p-nitrophenyl phosphate (Sigma, St. Louis, Mo.) at 1 mg/ml in 1M diethanolamine (DEA) was added and the plate incubated for 30 minutes at 37° C. The reaction was stopped with 25 µl per well of stop solution (0.1 M EDTA, pH 9.8) and the plate read at 405 nm on a Dynatech MR7000 reader.

2. Results

Figure 11:
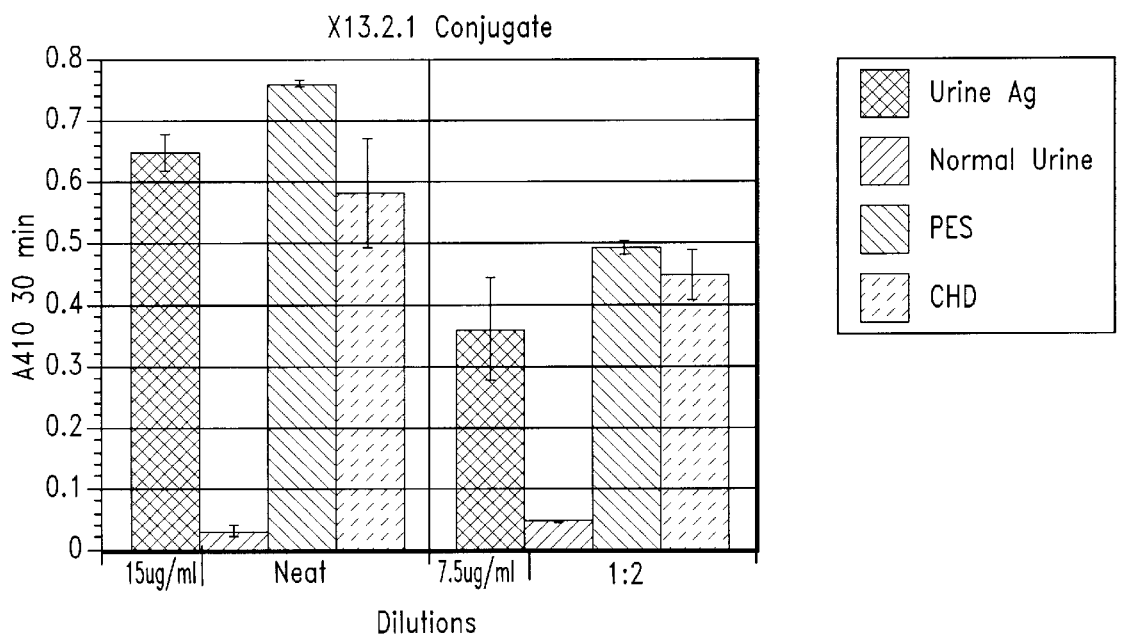
FIG. 11 presents a graphical representation of TCC+ urines and normal urines as analyzed by a C3b-MAb ELISA described herein.

As shown in FIG. 11, this assay format discriminated between TCC$^+$ urines (PES and CHD) and normal urines, yielding a positive signal for the TCC$^+$ urines.

E. C3b—Decay Accelerator Activity Assay

The assay described above in the C3b decay accelerator activity section (Example III.F.) discriminated three patient urines (all TCC$^+$) from a normal urine pool. Therefore, it may be used as an assay to indicate bladder cancer in patients.

F. SDS-PAGE Assay

The antigen partially purified by heparin agarose chromatography (Example III.A.) may also be detected by SDS-PAGE under reducing and non-reducing conditions, since it displayed a characteristic apparent molecular weight shift upon reduction (Example III.D.). As described above, the reduced antigen exhibited an apparent molecular weight (as estimated by SDS-PAGE) of ~151 kD as compared to ~138 kD under non-reducing conditions, presumably due to numerous disulfide bridges. The antigen containing peak from heparin chromatography was diluted in 2× SDS-PAGE sample buffer with and without dithiothreitol (DTT) at 5%. The samples were heated for 5 minutes in a boiling water bath and then allowed to cool at room temperature. Aliquots (2 µL) were loaded onto an 8 well, 7.5% acrylamide Pharmacia PhastGel (cat# 17-0622-01) and run on the Pharmacia PhastSystem (cat# 18-1018-23) according to manufacturer's protocol. Reduced and non-reduced samples were run on the same gel and were separated by molecular weight standards and an empty lane loaded with non-reducing 1× sample buffer. The gels were stained with Coomassie Blue R250 0.1% in 40% methanol and 10% acetic acid and then destained with 40% methanol with 10% acetic acid. Characteristic bands were seen on specimens with elevated antigen levels as detected by the ELISA (Example IV.B.).

G. RT-PCR Assay

1. Cell Lines

Several cell lines, particularly cell lines HTB-5 and HTB-9, which are derived from Transitional Cell Carcinoma (TCC) of the bladder and HeLaS3, which is derived from adenocarcinoma of the cervix (all from American Type Culture Collection, Rockville, Md.), were tested to determine whether they produce mRNA coding for the antigen. Although the method selected for cell line analysis was RT-PCR (Reverse Transcriptase based Polymerase Chain Reaction amplification of messenger RNA, mRNA), a variety of procedures used to detect the presence of specific RNA can be used. Controls were performed using PCR target materials (the PAW109 sequence) provided with commercial PCR kits, and its primers DM152 and DM151. Hybridoma cell line X-44.1 or normal human epithelial keratinocytes (Clonetics Corp., San Diego, Calif.) were chosen as the irrelevant target (Negative controls).

2. Preparation of mRNA

Preparation of mRNA was facilitated by the use of a Lysis Buffer containing: 7.5 M Guanidine HCl, 25 mM TES, 10 mM EDTA, 0.05% Taurodeoxycholate, 1 mM 2-mercaptoethanol, pH 7.5 (all reagents Molecular Biology grade from Sigma, St. Louis, Mo.). This buffer eliminated the necessity for grinding or icing samples and resulted in a stable preparation of DNA and RNA.

Cells were lysed in 1 mL lysis buffer per $10^8$ cells/mL cell culture media (IMDM, Irvine Scientific; Irvine, Calif.) supplemented with 15% FBS (Hyclone; Logan, Utah). The lysate was extracted with equal volumes of phenol and chloroform/isoamyl alcohol. The aqueous phase was aspirated and re-extracted with an equal volume of chloroform/isoamyl alcohol. The aqueous phase was precipitated with 7/13 volumes 10M LiCl (all reagents Molecular Biology Grade from Sigma Chemicals, St. Louis, Mo.). The mRNA was prepared from the total RNA produced in the previous steps using a PolyATtract kit (Promega, Madison, Wis.).

3. RT-PCR Amplification

RT-PCR amplification of antigen sequences was performed on a Perkin-Elmer 2400 Thermal Cycler using a GeneAmp PCR kit (Perkin-Elmer/Roche Molecular Systems, Branchburg, N.J.). Amplification was performed with 3 µL purified mRNA, 35 cycles, for the first amplification step of each reaction. The RT primer was designated 753RT, sequence TCGTTCATTCTCCTTAT (SEQ ID NO: 9). The PCR primer for the first reaction was designated 42M, sequence GCTGGTAAATGTCCTCT (SEQ ID NO: 10). For the nested PCR, 20 µL of product from the first PCR reaction was re-amplified for 35 cycles using the 753RT primer and primer 412M, sequence ATGTAATGAGGGG-TATC (SEQ ID NO: 11). All primer concentrations were set at 0.2 µM, and the annealing temperature was set at 48° C.

4. Results

Figure 2:
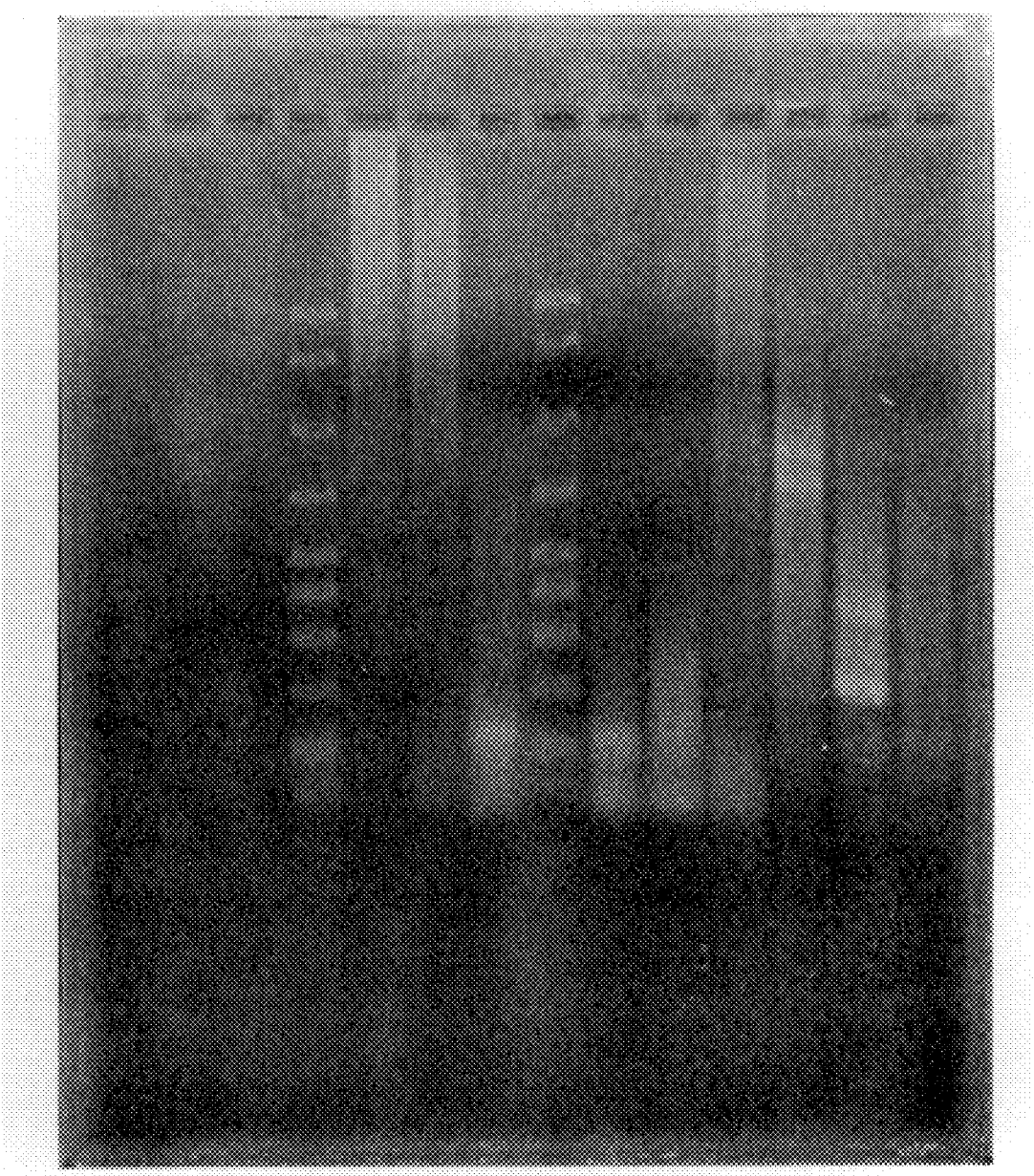
FIG. 2 shows the gel electrophoresis of the second-step PCR amplification products, with lanes 1 to 10 beginning at the right side of the gel as lane 1. Lane 1: X44.1 product (reaction 1, lane 1) with primers 753RT and 412M; Lane 2, HTB-5 product (reaction 1, lane 2) with 753RT and 412M; Lane 3, HTB-9 product (reaction 1, lane 3) with 753RT and 412M. Lane 4, PAW109 (reaction 1, lane 8) product with 753RT and 42M primers; Lane 5, X44.1 product with 753RT and 42M primers; Lane 6, HTB-5 product with 753RT and 42M primers; Lane 8, HTB-9 product with 753RT and 42M primers. Lanes 7 and 11, DNA molecular weight markers. Lane 9, PAW109 product (reaction 1, lane 8) with DM152 and DM151 primers; Lane 10, PAW109 product (reaction 1, lane 8) with 753RT and 412M primers.
Figure 3:
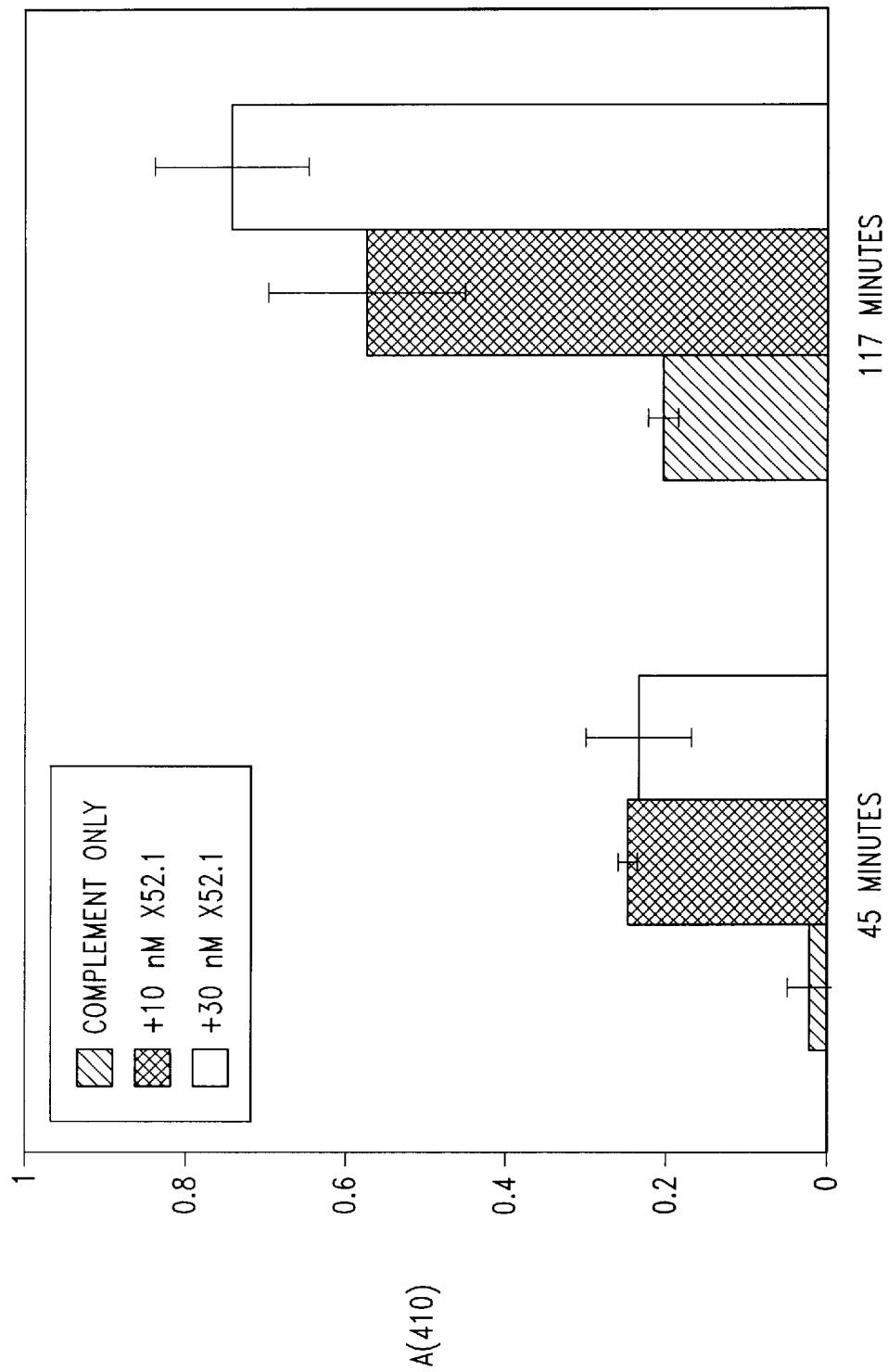
FIG. 3 shows stimulation by MAb X52.1 of the complement-mediated lysis of rabbit red blood cells. The extent of lysis is shown after 45 and 117 minutes with complement alone and in the presence of X52.1 at concentrations of 10 nNM and 30 nM.
Figure 4:
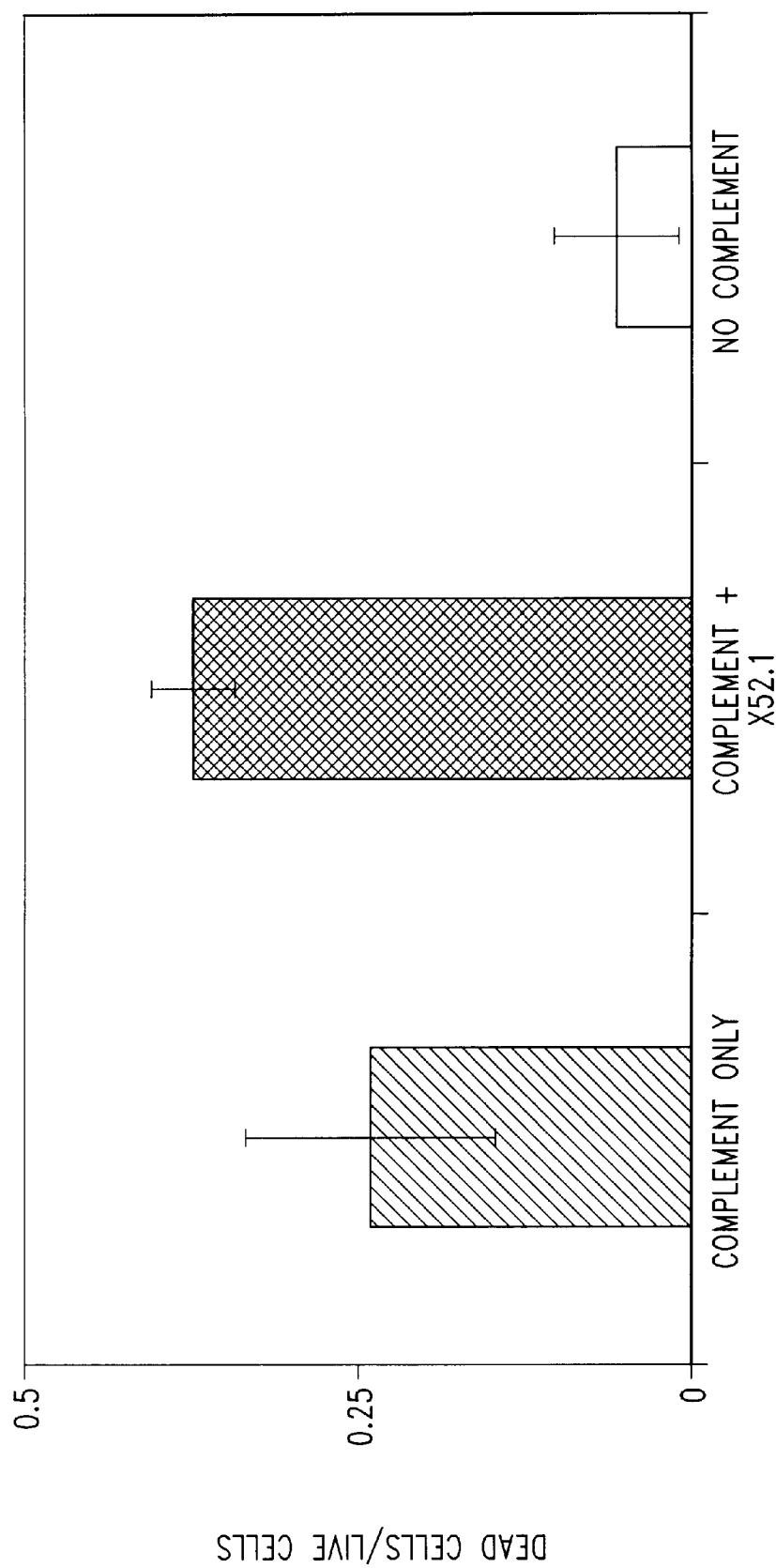
FIG. 4 shows stimulation by MAb X52.1 of the complement-mediated lysis of HL-60 human myeloid cells. The extent of lysis is shown after 120 minutes (a) with complement alone, (b) in the presence of X52.1 at a concentration of 10 nM, and (c) in the absence of complement.

Gel electrophoresis of the first-step RT-PCR products is shown in FIG. 1. Analysis of the second-step products by electrophoresis in TAE buffer (40 mM Tris-acetate, 20 mM EDTA, pH 8.3) on a 1 percent agarose gel revealed a band of the expected size, 341 bp, upon staining with ethidium bromide (FIG. 2, lane 3). Amplification of the kit positive control PAW 109 gave the expected 311 base pair product. Re-amplification of this product with the kit DM152 and 151 primers was negative, a common result when re-amplifying PCR product without changing primers.

EXAMPLE V

CERVICAL CANCER

A. Cervical Specimen Handling and Disposal

1. Preparation of tubes for cervical sample collection and transportation:

Tubes: Corning polypropylene, 4 mls, cat # SP:T4188-5, containing 100 µl of saline solution each, and were shipped to the clinical sites.

Cervical samples were collected using swabs. The swabs were inserted into the tubes and the tips broken off prior to covering the tubes for shipment.

2. Specimen Preparation prior to Assay:

Add 2 mls of 100 mM NaCl, 10 mM Tris-HCl (pH 8.0) containing 1 mM EDTA to 2 tubes and this buffer containing 0.1% Tween to the third tube. (The third sample is for investigating sample elution from the swab and may be used for other extraction buffers as needed.)

Vortex tubes for 3–5 minutes.

Pull out the swab with forceps while squeezing to the side of the tube to let all fluids out of the swab.

Recap the tubes and centrifuge for 5 minutes at 3000 rpm in a table top centrifuge.

Serially dilute the supernatant to ⅛ and 1/16 with buffer.

Add 20 µl of protease inhibitor cocktail to each tube and 20 µl of the 10% sodium azide solution. Mix well and freeze remaining supernatants at −80° C. prior to testing in ELISA.

B. ELISA

Figure 12:
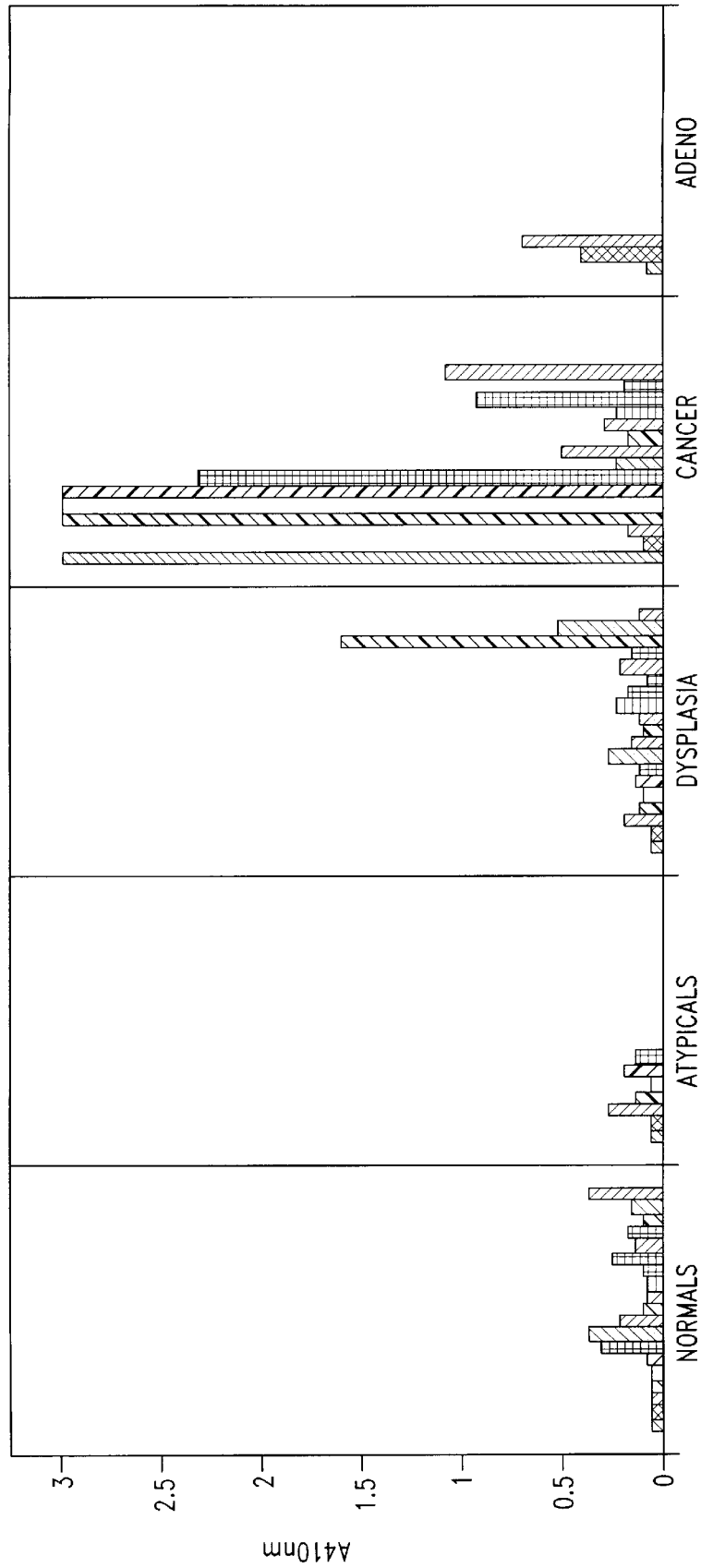
FIG. 12 presents a graphical representation for cervical specimens as analyzed by an ELISA format described herein.

Sixty-three cervical samples were tested in several EIA combinations (Example IV.B.) including the X-52.1MAb/X-13.1 ALP sandwich EIA. The following are the assay procedure and results:

1. Assay Procedure
a. EIA plates (COSTAR-Hi binding) were coated with X-52.1 MAb at 5 µg/ml in Carb/Bicarb buffer (pH 9.6), 100 µl per well, and incubated overnight at 4° C.
b. Coating buffer was discarded and the plates were blocked with 250 µl per well with 2% BSA/PBS (pH 7.4) for 2 hrs at room temp.
c. Plates were then washed once with TBS containing 0.1% Tween-20.
d. Cervical samples were thawed at room temperature, centrifuged at 3000 rpm for 5 mins, then the supernatant was diluted to 1:20 in 25 mM Tris-HCl, pH 7.8, in tubes and 100 µl of sample/diluent transferred per well to duplicate wells. The plates were sealed with plate covers and incubated at 37° C. for 2 hrs.
e. Plates were washed 4× with TBS containing 0.1% Tween-20.
f. X13.1-AP conjugate was diluted to 2 µg/ml in 1% BSA/TBS (pH 7.4) and 100 µl transferred to each well. Plates were then covered and incubated at 37° C. for 2 hrs.
g. Plates were washed 4× with 0.1% T/TBS.
h. A 1 mg/ml solution of p-NPP/1M diethanolamine was made (pH 9.8), and 100 µl was transferred to each well. Plates were sealed with plate covers and incubated at 37° C. for ½ hour.
i. Color development was stopped by adding 50 µl per well of 0.1M EDTA (pH 9.8).
j. Plates were read at 410 nm on a Dynatech MR7000
2. Results Results from the study of the cervical specimens with this assay are tabulated in Table 6 and presented graphically in FIG. 12.

TABLE 6

|  | X13.1MAb/ X52.1-AP |
| --- | --- |
| Sensitivity (cancers) n = 15 | 73% |
| Specificity (normals) n = 19 | 100% |
| % Adenocarcinoma above cutoff n = 3 | 33% |
| % Dysplasia above cutoff n = 19 | 16% |
| % Atypicals above cutoff n = 7 | 0% |
| Cutoff (Mean OD of Normals + 2SD) | 0.201 |

Example VI

PRODUCTION OF CFHRP IN CANCER

5 A. Production of CFHrp in Cancer Cell Lines
1. Detection of Antigen in Cell Culture Media by Immunossay Cell culture media were tested for the presence of antigen (complement Factor H-related protein, CFHrp) using the sandwich enzyme immunoassay as described in Example IV.B. The media tested were those taken from cell cultures used for the preparation of total cellular RNA. After removal of the cultured cells, the remaining media free of cells were then diluted, as necessary, and tested in the EIA, as described. Control experiments involved the testing of fresh media, in particular those specified by ATCC or Clonetics Corporation (San Diego, Calif.) for the cell lines or primary cultures of interest. These were typically Modified Eagle's Media containing 10% fetal bovine serum (Sigma Chemical).

2. Detection of Message for Antigen in Cancer Cells by RT-PCR cDNA was synthesized from mRNA present in preparations of total cellular RNA from cancer cell lines, using Reverse Transcriptase plus Random Hexamer primers. The concentrations of components within the reaction mixture were as follows:

| Component | Final Concentration |
| --- | --- |
| $MgCl_2$ | 5 mM |
| KCl | 50 mM |
| Tris-HCl, pH 9.0 | 10 mM |
| Triton X-100 | 0.1% v/v |
| dGTP | 1 mM |
| dATP | 1 mM |
| dCTP | 1 mM |
| dTTP | 1 mM |
| RNAsin | 1 U/µL |
| Random Hexamers | 5 µM |
| MuLV Reverse Transcriptase | 2.5 U/µL |

Sample and DEPC-treated deionized water were added to bring the reaction volume to 20 µL. Between 1 and 5 µg of total RNA was added to each reaction mixture. Typically, 2 µg is sufficient. The cDNA reaction was allowed to proceed for 90 minutes at 42° C.

PCR of huCFH and huCFHrp mRNA was performed primarily with primer pair 42M and 1040RT (TCTGGATAATCACAAGGTTTC) (SEQ ID NO: 17), and primer pair 2910M (GTCAGACAGTTATCAGTATGGAGAAGAAG) (SEQ ID NO: 18) and 3610RT (CTGTTTGGCTGTCCACCTTAATGCTATG) (SEQ ID NO: 19). In addition, the presence of the correct internal sequences were confirmed with the primer pair 410M (ACATGTAATGAGGGGTATCAA) (SEQ ID NO: 20) and 1040RT. The PCR master mix consisted of the following:

| Component | Final Concentration |
| --- | --- |
| $MgCl_2$ | 3 mM |
| KCl | 50 mM |
| Tris-HCl, pH 9.0 | 10 mM |
| TritonX-100 | 0.1% v/v |
| Taq DNA Polymerase | 2.5 U/100 µL |
| Primer Pairs: | |
| 42M/1040RT | 1–5 µM |
| or | |
| 2910M/3610RT | 1–5 µM |
| or | |
| 410M/1040RT | 1–5 µM |

PCR was performed by adding 80 µL of master mix to each cDNA reaction tube. Thermal cycling was performed in a Perkin-Elmer (Foster City, Calif.) model 2400 cycler for 40 cycles. Positive results were determined by electrophoresis (e.g., at 90 volts for 90 min. ) on 2% agarose gels, followed by staining with ethidium bromide, and destaining in deionized water.

For purposes of this application, moderate stringency hybridization and PCR amplification conditions are defined as those performed at the calculated melting temperature (Tm) of the probe/primer with the target. The recommended formula for calculating Tm, and its limitations, are well known in the art (i.e., are found in Sambrook, J., Fritsch, E. F. and T. Maniatis, *Molecular Cloning*, 2d Edition, Cold Spring Harbor Laboratory press, pp. 9.51–9.52, 1989). High stringency conditions are defined within this application as hybridization/amplification performed at least 4° C. above the calculated Tm.

Using primer pair 42M/1040RT, CFHrp are detected at moderate (52° C.) to high stringency (56° C.) conditions, based on the homology of the cDNA to that of the primers identified in this application. Using primer pair 2910M/3610RT, CHFrp are detected at moderate (67° C.) to high stringency (72° C.) conditions, based on the homology of the cDNA to the primer pair. For internal CDNA sequence, using the primer pair 410M/1040RT, CFHrp are detected at moderate (48° C.) to high stringency (56° C.) conditions.

For PCR studies, DEPC-treated deionized water, Taq polymerase, RNAsin, and MuLV Reverse Transcriptase were from Promega Corporation (Madison, Wis.). Primers were synthesized by Midland Certified Reagents (Midland, Tex.) and were purified by anion-exchange chromatography. Agarose gels and ethidium bromide were from Sigma. All other reagents were obtained from Perkin-Elmer.

3. Results a. Antigen Production and mRNA in Various Cell Lines

Table 7 illustrates that a wide variety of human cancer cells from established lines express CFHrp tumor antigen as determined by presence of immunologically active antigen in the cell culture media and the appropriate mRNA within the cells. Myeloid lines, a human colon cancer line, and normal human epithelial keratinocytes (a primary culture, not an established cell line) are negative for antigen expression by both assay methods used. In contrast, many bladder, renal, cervical and prostate cancer cell lines produce this tumor antigen.

TABLE 7

Production of huCFH by Various Cell Lines

| Cell Line | Tumor Source | sEIA (Media) | RT-PCR |
|---|---|---|---|
| RCC7860 | Renal Cell Ca. | Neg | ++ |
| ACHN | Renal Cell Ca. | Neg | (+) |
| Pastor | Renal Cell Ca. | + | ++ |
| 769P | Renal Cell Ca. | + | ++ |
| CAKI-1 | Renal Clear Cell | Neg | (+) |
| HL60 | Myeloid | Neg | Neg |
| LSI74T | Colon Adeno Ca. | Neg | Neg |
| T24 | TCC, Bladder | 3+ | ++ |
| 5637 | Primary Bladder CA | Neg | + |
| RT4 | Papillary Bladder CA | 3+ | ++ |
| J82 | TCC, Bladder | 3+ | (+) |
| 486P | TCC, Bladder | 3+ | ++ |
| HTB5 | TCC, Bladder | Neg | + |
| HTB9 | TCC, Bladder | 2+ | ++ |
| DU145 | Prostate Ca. | ND | + |
| PC3 | Prostate Ca. | ND | + |
| LNCaP | Prostate Ca. | ND | (+) |
| HeLaS3 | Cervical Adeno Ca. | 4+ | ++ |
| HTB33 | Cervical | ND | + |
| C4I | Cervical | ND | + |
| DMEM/10% FBS | Cell Culture Media (not exposed to human cells) | Neg | NA |
| NHEK | Normal human epithelial keratinocytes, NOT an established cell line | Neg | Neg |
| X44.1 | mouse hybridoma | Neg | Neg |
| X52.1 | mouse hybridoma | Neg | Neg |
| X13.2 | mouse hybridoma | Neg | Neg |

NA, not applicable; ND, not determined b. Analysis of RT-PCR Amplification Products Total RNA was set at 3 μg and 40 cycles of amplification were performed. Annealing temperatures were set at 50° C. for 42M1040RT pairs, 56° C. for 410M1040RT and 70° C. for 2910M3610RT. The 42M1040RT product expressed with mRNA from cervical adenocarcinoma HeLaS3 cells is of the expected size for a human CFH-derived product and includes the 5' UTR or CFH, to which the 42M primer hybridizes. A second upstream primer, designated 410M (ACATGTAATGAGGGGTATCAA) (SEQ ID NO: 20) and also derived from the huCFH sequence (GenBank Accession number Y00716), also yields a product of expected size and restriction map from HeLaS3 cells. In addition, RT-PCR of total RNA from TCC bladder cancer cell line HTB9 yields a cDNA of an appropriate size and restriction map using the 410M1040RT primer pair. The same primer pair yields no amplicon at the expected size for the colon adenocarcinoma line LS174T, myeloblastoma line HL-60 or normal human epithelial keratinocytes (NHEK). The experiments with preparations of HeLaS3 and HTB9 total RNA utilizing the 42M1040RT primer pair produced not only cDNA of the expected size, but also amplicons of unexpected sizes at 800 base pairs and, just above the limit of detectability, at 450, 480 and 1400 base pairs. In contrast, under the same conditions, the LS 174T cell line produces only cDNA of incorrect sizes at 800, 450 and 420 base pairs, as well as an amplicon of 1200 base pairs which is at the limit of detectability.

Alterations in the CFH gene product are not restricted to the 5' end of the molecule. Although amplification of the downstream portion of the HeLaS3 cDNA with CFH primers 2910M (GTCAGACAGTTATCAGTATGGAGAAGAAG) (SEQ ID NO: 18) and 3610RT (CTGTTTGGCTGTCCACCTTAATGCTATG) (SEQ ID NO: 19) yielded amplicons of the expected size, the same primer pair yielded no amplicon with RNA from LS174T. Furthermore, both NHEK and HL-60 lines remained negative for the expression of CFHrp.

Figure 5:
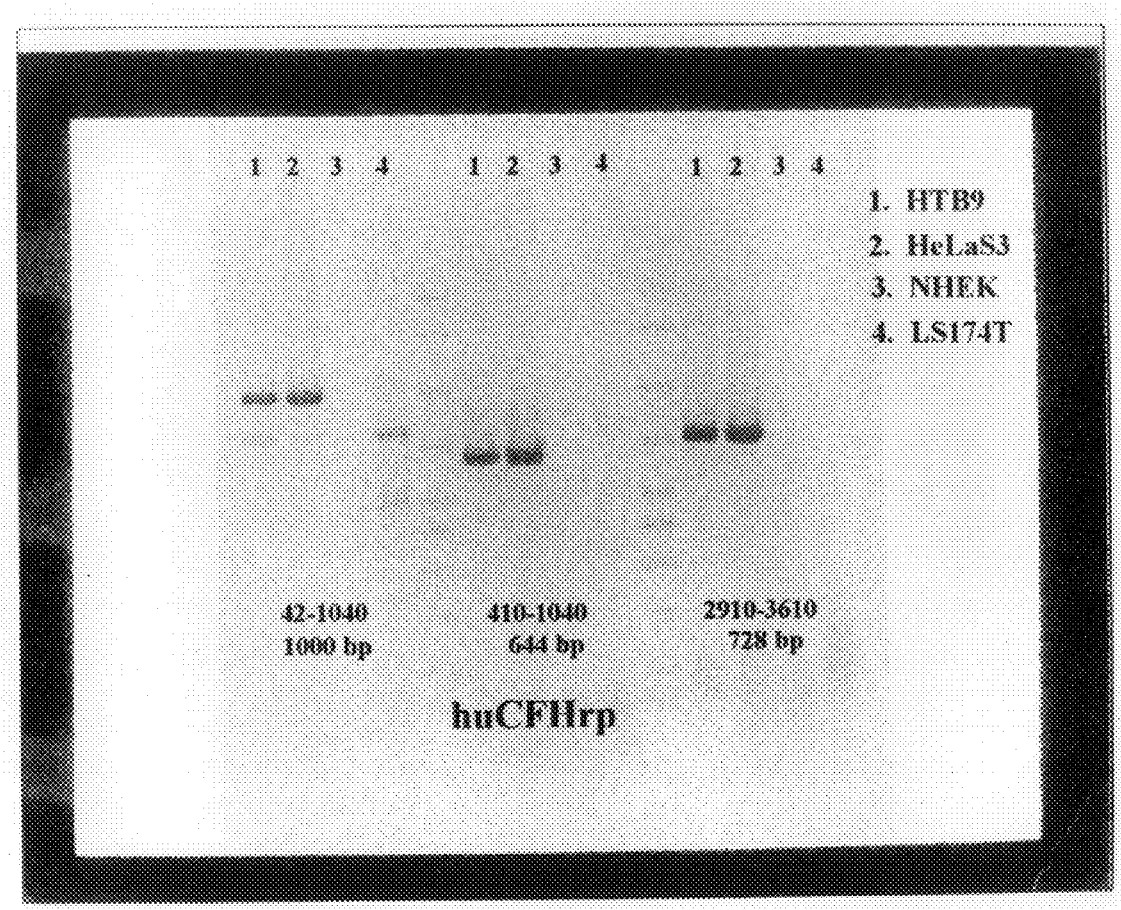
FIG. 5 shows the gel electrophoresis of amplification products resulting from RT-PCR performed with three primer sets derived from human complement Factor H (lanes 1 to 10 beginning at the left side of the gel with the left side set of numbers 1–4 on the Figure representing lanes 1–4, the middle set of numbers 1–4 representing lanes 6–9 with lane 5 preceding, and the right side set of numbers 1–4 representing lanes 11–14 with lane 10 preceding). Lane 1: HTB-9 product with primers 1040RT and 42M; Lane 2: HeLaS3 product with primers 1040RT and 42M; Lane 3: NHEK product with primers 1040RT and 42M; Lane 4: LS174T product with primers 1040RT and 42M; Lane 6: HTB-9 product with primers 1040RT and 410M; Lane 7: HeLaS3 product with primers 1040RT and 410M; Lane 8: NHEK product with primers 1040RT and 410M; Lane 9: LS174T product with primers 1040RT and 410M; Lane 11: HTB-9 product with primers 3610RT and 2910M; Lane 12: HeLaS3 product with primers 3610RT and 2910M; Lane 13: NHEK product with primers 3610RT and 2910M; Lane 14: LS174T product with primers 3610RT and 2910M; Lanes 5 and 10: DNA molecular weight markers.
Figure 9A:
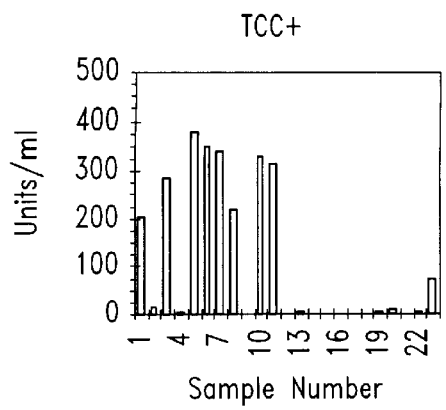
FIGS. 9A–9E present a graphical representation for urine samples as analyzed by an ELISA format described herein. The data is expressed as units of analyte/mL. The categories are TCC+ (FIG. 9A), Healthy (FIG. 9B), Non-GU Disease (FIG. 9C), GU Malignancy and Other GU Diseases (FIG. 9D), and Chronic Inflammation (FIG. 9E).
Figure 9B:
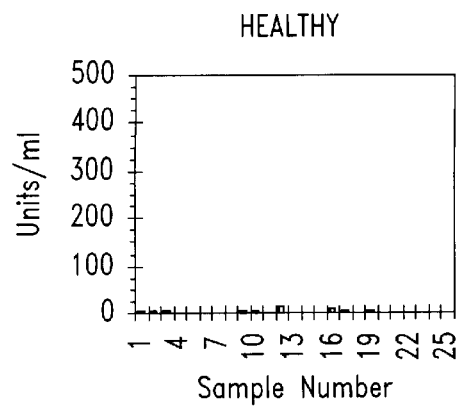
Figure 9C:
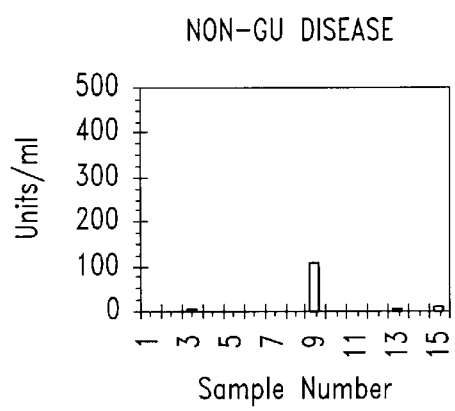
Figure 9D:
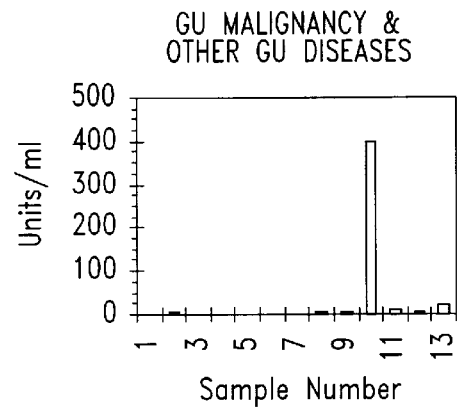
Figure 9E:
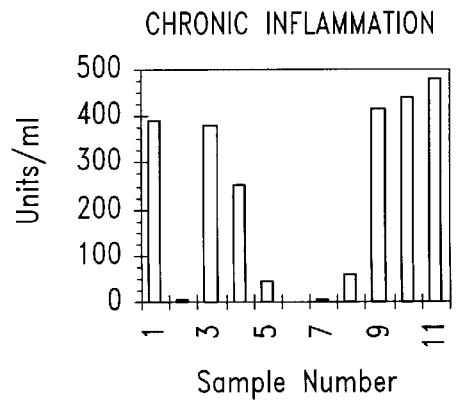

FIG. 5 shows the gel electrophoresis of amplification products resulting from RT-PCR performed with three primer sets derived from human complement Factor H (lanes 1 to 10 beginning at the left side of the gel with the left side set of numbers 1–4 on the Figure representing lanes 1–4, the middle set of numbers 1–4 representing lanes 6–9 with lane 5 preceding, and the right side set of numbers 1–4 representing lanes 11–14 with lane 10 preceding). Lane 1: HTB-9 product with primers 1040RT and 42M; Lane 2: HeLaS3 product with primers 1040RT and 42M; Lane 3: NHEK product with primers 1040RT and 42M; Lane 4: LS 174T product with primers 1040RT and 42M; Lane 6: HTB-9 product with primers 1040RT and 410M; Lane 7: HeLaS3 product with primers 1040RT and 410M; Lane 8: NHEK product with primers 1040RT and 410M; Lane 9: LS174T product with primers 1040RT and 410M; Lane 11: HTB-9 product with primers 3610RT and 2910M; Lane 12: HeLaS3 product with primers 3610RT and 2910M; Lane 13: NHEK product with primers 3610RT and 2910M; Lane 14: LS174T product with primers 3610RT and 2910M; Lanes 5 and 10: DNA molecular weight markers.

B. Method of Cloning cDNA Coding for CFHrp

A cDNA of the appropriate size and restriction pattern for human CFH was prepared from mRNA isolated from the HeLaS3 human cervical adenocarcinoma cell line. This cDNA, prepared with primers 42M and 1040RT, was blunt-end cloned into pBluescript SK (Stratagene, La Jolla, Calif.).

1. Cloning and Sequencing a. PCR product, in a total volume of 73 μL, was purified using a Prep-A-Gene DNA purification kit (Stratagene). To the product in solution, 360 μL of the purification kit binding buffer and 20 μL of Prep-A-Gene DNA binding matrix were added. Purification was then performed according to the protocol described in the package insert.

DNA concentration was estimated by running 2 μL of the purified material on a 2% agarose gel (Sigma) and comparing its intensity to the intensity of a standard (Sigma) of known concentration.

b. To ensure that the PCR product had blunt ends, the ends were filled in using the PCR Polishing Kit (Stratagene). 1 μL of dNTP mix and 1 μL of Pfu Polymerase were added to 7 μL of purified PCR product to which had been added 1 μL of 10× Pfu Polymerase Buffer. The reaction mixture was incubated at 72° C. for 30 minutes. Polished reactions were stored at −80° C. until use. No further purification was required.

c. In order to yield blunt ends, 20 μg of pBluescript SK− was digested with 30 units of Eco RV in a 100 μL reaction volume containing 6 mM Tris-HCl, pH 7.9, 6 mM MgCl$_2$, 150 mM NaCl, and 1 mM DTT. The reaction mixture was incubated overnight (16–18 hours) at 37° C.

d. Phenol extraction of the digested plasmid was performed by adding an equal volume of Buffer-Saturated Phenol (Sigma) and vortexing to mix. The mixture was centrifuged at 5000 rpm for 5 minutes to separate the phases. The upper aqueous phase was removed and transferred to a new tube.

To the aqueous solution were added 50 μL phenol and 50 μL chloroform:isoamyl alcohol (24:1). The phases were mixed by vortexing and separated as above. The upper aqueous phase was removed and transferred to a new tube. This aqueous phase was again extracted with 100 ul of chloroform:isoamyl alcohol. The phases were separated as before, and the upper aqueous phase was removed and transferred to a fresh tube.

e. In order to precipitate DNA from the aqueous solution, 0.5 volumes of 7.5 M ammonium acetate (pH 5.5) and 2 volumes of ethanol were added and incubated at −20° C. for 1 hour. DNA was pelleted by centrifugation at 12,000×G for 20 minutes. The ethanol was carefully decanted. The DNA pellet was washed with 500 μL of 70% ethanol and then pelleted and supernatant decanted as above.

The DNA pellet was allowed to air dry by inverting the tube until just dry by visual inspection and was then resuspended in water (Molecular Biology Grade, Sigma).

f. 10 μg of digested pBluescript DNA was dephosphorylated with 500 units of Calf Intestinal Alkaline Phosphatase by incubating at 37° C. for 15 minutes in a total volume of 100 μL, containing 0.05 M Tris-HCl, pH 9.3, 1 mM MgCl$_2$, 0.1 mM ZnCl$_2$ and 1 mM Spermidine. Another 500 units of alkaline phosphatase was added and reaction was incubated at 56° C. for 45 minutes. The reaction mixture was then incubated at 65° C. for 1 hour to inactivate the alkaline phosphatase. The reaction mixture was extracted with phenol and chloroform and then precipitated with ethanol, as described in step (d).

g. Ligation of vector and insert was performed using the two-step ligation procedure described by S. Damak and D. W. Bullock (*BioTechniques* 15(3):448–452, 1993). In the first step of the ligation process, vector and insert were mixed together at vector:insert ratio of 1:4. 150 nmol of polished insert was mixed with 36 nmol of vector in a 10 μL volume containing 0.05 M Tris, 0.025 M MgCl$_2$, 0.5 mM ATP, 1 mM DTT, 1 unit of T4 DNA Ligase and 10 units of EcoRV. The reaction was incubated at room temperature for 2 hours For the second part of the ligation process, 190 μL of a solution containing 0.05 M Tris, 0.025 M MgCl$_2$, 0.5 mM ATP, 1 mM DTT, and 19 units of T4 DNA Ligase was added to the reaction mixture from the first step and incubated at room temperature overnight (16–18 hours).

h. Transformation of competent *E. Coli* was initiated by first thawing frozen competent DH5 (Stratagene) cells in an ice water bath.

1.7 mL microfuge tubes were labelled and placed on ice. When thawed, 50 μL of the competent cells was pipetted into the labelled tubes. 5 μL of the ligation reaction mixture was added to the tube containing the competent cells. The tube was flicked briefly to mix and incubated on ice for 30 minutes. This tube containing the competent cell/ligation mixture was then incubated at 37° C. for 20 seconds. A 0.95 mL volume of LB broth (Sigma) was added and tubes were incubated at 37° C. for 1 hour with shaking at 225 rpm. 200 μL of cell mixture was spread, using sterile spreaders, onto the surface of an LB agar plate containing 50 μg/ml Ampicillin, 25 μg/ml X-Gal and 60 μg/ml IPTG (all reagents from Sigma). Plates were covered and incubated at 37° C. overnight (16–18 hours). White colonies were selected and screened by purifying the plasmid DNA and then performing restriction analysis.

i. All DNA sequencing was performed on ABI Prism sequencers (Perkin-Elmer, Foster City, Calif.) in the laboratory of Dr. Leroy Hood, Center for Molecular Biotechnology, University of Washington, Seattle, Wash.

Results

Table 8 is a tabulation of observed differences between the clone sequences (for DNA encoding complement Factor H-related protein) and the published sequence for DNA encoding human complement Factor H (CFH).

TABLE 8

Apparent Differences Between Clone and Human CFH Sequences

| Clone | RNA Source | DNA Position Number | DNA Change | Mature Protein Position Number | Amino Acid Change |
|---|---|---|---|---|---|
| pRBB9FH410#2.1 | HTB9 | 672 | A to G | 181 | S to G |
| pRBS3FH2910#2.1 | Hela S3 | 3096 | G to T | 989 | V to L |
| pRBS3FH2910#3.1 | Hela S3 | 3046 | T to C | 972 | L to P |
| | | 3094 | A to G | 988 | D to V |
| | | 3096 | G to T | 989 | V to L |
| | | 3142 | A to G | 1004 | Y to C |
| | | 3144 | A to C | 1005 | K to Q |
| pRBS3FH2910#4.1 | Hela S3 | 3053 | A to G | 974 | No Change |
| | | 3096 | G to T | 989 | V to L |
| | | 3115 | A to C | 995 | Q to P |
| pZS3FH2576#3 | Hela S3 | 2621 | A to G | 830 | No Change |
| | | 2746 | G to T | 872 | S to I |
| pZS3FH2576#1/11 | Hela S3 | 2746 | G to T | 872 | S to I |

FIG. 6A shows a partial DNA sequence from clone pRBB9FH410 and FIG. 6B the corresponding amino acid sequence, as compared to the DNA and amino acid sequences for human CFH. FIG. 7A shows three partial DNA sequences from clone pRBS3FH2910 and FIG. 7B the corresponding amino acid sequences, as compared to the DNA and amino acid sequences for human CFH. FIG. 8A shows two partial DNA sequences from clone pZS3FH2576 and FIG. 8B the corresponding amino acid sequences, as compared to the DNA and amino acid sequences for human CFH.

2. Generation and Use of Riboprobes a. A riboprobe for use in in situ hybridization was prepared from the same clone. Restriction digestion of the clone was performed with Ava II (New England Biolabs, Beverly, Mass.) following the manufacturer's instructions. The resulting cDNA corresponded to map positions 457–1057 of huCFH (GenBank sequence number YM00716). The cDNA product was purified by electrophoresis on a 1% agarose TAE gel (Sigma). A digoxin-labelled ribonucleic acid antisense probe was prepared with T7 RNA polymerase, using a commercial kit (Boehringer-Mannheim, Indianapolis, Ind.) and following the instructions in the package insert. Unlabelled RNA for probe competition was synthesized in a similar manner using a kit from Ambion (Austin, Tex.) following the manufacturer's instructions.

b. The resulting Riboprobes were purified by precipitation with an equal volume of absolute ethanol and were then redissolved in ribonuclease-free water to final concentrations of either 101 nM for the digoxigenin-labelled probe or 10 uM for the unlabelled probe.

c. Pathology tissue specimens were prepared for staining by snap freezing in liquid nitrogen. The frozen pellets were sectioned on a cryostat microtome (Bartles & Stout) and then fixed in (−20° C.) acetone (Sigma) for 15 minutes. Fixed sections were placed on a slide and kept wet in APK buffer (Ventana, Tucson, Az.) until the hybridization process was begun.

d. For tissue staining, 1 $\mu$L of stock riboprobe was diluted into 500 $\mu$L of hybridization solution, consisting of 2× Denhardt's solution supplemented with 60% (w/v) formamide, 12.5% dextran sulfate, 10 mM Tris, 1 mM EDTA, 1 mM DTT, 375 mM NaCl, 0.3% Triton X100, and containing 2 mg tRNA (all reagents from Sigma). Final concentration of the digoxigenin-labelled RNA probe was 0.3 nM.

e. Staining was performed on an ES GenII slide processor (Ventana, Tucson, Ariz.), using reagent packs and buffers from the manufacturer, with detection by HRP-conjugated anti-mouse antibody. Hybridization solution containing the riboprobe was applied manually and processed wet. Following denaturation for 2 minutes at 65° C., hybridization was carried out at 40° C. for 120 minutes. Three washes were performed at 55° C. sequentially with 1× SSC (150 mM sodium chloride, 15 mM sodium citrate, pH 7.0–7.5) 0.5× SSC and 0.1× SSC. Slides were then reacted with anti-digoxigenin antibody following the manufacturer's instructions (Boehringer Mannheim).

f. A specificity control was performed by application of riboprobe stock containing a 100-fold excess of riboprobe that had not been labeled with digoxigenin.

Results

The target tissues subjected to staining with the riboprobe were serial sections from normal and cancerous human bladder (transitional cells) and from normal and cancerous human prostate. All tissue sections, both normal and cancerous, were from a single bladder or a single prostate.

Specificity of tissues staining was established by competition of digoxigenin labelled probe binding with a 100-fold excess of unlabelled probe. Only sections from TCC+ bladder cancer stained with the HeLaS3 generated probe sequence.

Example VII

INHIBITION OF ANTIGEN BIOLOGICAL ACTIVITY BY MABS

A. In Vitro Protection of C3b by Anti-CFH Related Protein MAbs

As shown in Example III.F the complement Factor H-related activity of antigen can be mimicked by complement Factor H itself. For experimental clarity, therefore, Factor H and Factor I were used to degrade C3b and illustrate the protective actions of anti-Factor H-related protein MAbs.

Reactions were performed by incubating 1 $\mu$g of Factor H with either 15 or 30 $\mu$g of each of three MOF MAbs (X52.1; X87.2; X13.2), in 20 $\mu$L of phosphate-buffered saline for 30 minutes at 37° C., followed by the addition of 7.5 $\mu$g of C3b and 5 $\mu$g of Factor I into each reaction tube (final reaction volume 32.5 $\mu$L). (C3b was generated from C3 by the method of Pangbum, M. K., and Mueller-Eberhard, H. J., *Biochemistry* 22:178–185, 1983.) The mixture was then incubated on a rotator at 37° C. for 1 hour. Results were determined by SDS-PAGE of the reaction mixtures under reducing conditions (50 mM DTT) on a 4–12% gradient gel (Novex, San Diego, Calif.). (Unless specified otherwise, all reagents are from Sigma, St. Louis; Mo.) The gel was scanned with a GelDoc scanner (BioRad, Hercules, Calif.). The intensities of the bands measured in this way were converted to percentage of C3b remaining. The control lane containing the reaction mixture in the absence of MAb was used to represent 100 percent degradation, while the lane containing the reaction mixture with no Factor H was used to represent 0 percent degradation.

Results

The results derived from scanning the gel are summarized in Table 8. These results demonstrate that MAbs X13.2 and X87.2 are able to block the Factor H-related protein antigen-mediated degradation of complement component C3b in vitro.

B. Activation of Cell Lysis by the Alternate Complement Pathway by MAbs Specific for the Antigen Standard guinea pig complement was treated with 5 mM EGTA to chelate calcium. Then 5 mM $MgCl_2$, which is required for the activity of the alternative complement pathway (ACP), was added. The mixture was incubated for 20 minutes at 37° C., then added to $7\times10^9$ rabbit red blood cells (RBC) and further incubated at 37° C. After 45 minutes and again after 117 minutes, hemolysis was determined by measuring the $A_{450}$ and comparing the values to those determined for control reactions, which had received either no complement or no MAb. Measurements were performed on a Dynatech (Chantilly, Va.) MR5000 96-well microplate reader. Hemolysis was determined in the absence or presence of MAb X52.1. When included, the MAb was used at a concentration in the reaction mixture of 10 nM or 30 nM (FIG. 3). All reagents and materials were purchased from Sigma.

A second experiment was performed under the same conditions as the RBC lysis, but the target cells were HL-60 ($1\times10^8$ cells), a human mycloid cell line. MAb concentration was set to 10 nM, and lysis was read after 120 minutes as described above (FIG. 4).

Results

Although MAb X52.1 was not effective in the format used in Example VII.A above, perhaps due to a lower affinity for Factor H, it was highly effective in promoting lysis of RBCs or HL-60 cells. RBC lysis was dependent on the concentration of MAb and the duration of incubation. Since X52.1 does not bind to RBCs or HL-60 cells, and since HL-60 cells do not produce Factor H, the mechanism of action of cell lysis must be the binding of X52.1to the Factor H in the added guinea pig complement and resulting inhibition of the C3 stabilization activity of the Factor H.

In summary, MAb X52.1, which specifically binds antigen and CFH, but does not bind red blood cells, Factor I or C3b, can promote the ACP-mediated lysis of RBCs. The concentrations required to do this are achievable physiologically (10 nM, or approximately 1.5 $\mu$g/mL).

TABLE 9

Inhibition of C3b Degradation in the
Presence of Anti-Antigen MAbs

| Sample | Quantity of Sample | C3b Remaining (Percent) |
|---|---|---|
| Control, No MAb | Standard | 0 |
| X52.1 | 15 μg | 0 |
| X52.1 | 30 μg | 0 |
| X87.2 | 15 μg | 24.7 |
| X87.2 | 30 μg | 54.9 |
| X13.2 | 15 μg | 62.0 |
| X13.2 | 30 μg | 54.0 |
| Control, No Factor H | Standard | 100 |

All publications and patent applications mentioned in this specification are herein incorporated by reference to the same extent as if each individual publication or patent application was specifically and individually incorporated by reference.

From the foregoing, it will be appreciated that, although specific embodiments of the invention have been described herein for purposes of illustration, various modifications may be made without deviating from the spirit and scope of the invention.

We claim:

1. A method of screening for a cancer comprising the step of detecting the presence of a tumor-associated human complement Factor H-related antigen or a nucleic acid molecule encoding said antigen in a sample, said nucleic acid molecule characterized by the ability of the cDNA of said nucleic acid molecule to hybridize at 50° C. with the primer pair 42M/1040RT or at 67° C. with the primer pair 2910M/3610RT to form hybrids which are amplifiable by PCR amplification.

2. A method according to claim 1 wherein the method comprises the step of detecting the presence of the antigen.

3. A method according to claim 1 wherein the method comprises the step of detecting the presence of a nucleic acid molecule encoding the antigen.

4. A method according to claim 1, 2 or 3 wherein the cancer is urogenital or renal cancer.

5. A method according to claim 4 wherein the urogenital cancer is bladder, cervical or prostate cancer.

6. A method according to claim 1, 2 or 3 wherein the antigen is further characterized by the ability to bind complement fragment C3b.

7. A method according to claim 1, 2 or 3 wherein the antigen is further characterized by the ability to bind to heparin agarose.

8. A method according to claim 1, 2 or 3 wherein the antigen is further characterized by the presence of a polypeptide with a molecular weight of 138,000 which shifts to a molecular weight of 151,000 in the presence of a disulfide reducing agent, as estimated by sodium dodecyl sulfate-polyacrylamide gel electrophoresis.

9. A method according to claim 1, 2 or 3 wherein the antigen is further characterized by at least two of: (1) the ability to bind complement fragment C3b, (2) the ability to bind to heparin agarose, and (3) the presence of a polypeptide with a molecular weight of 138,000 which shifts to a molecular weight of 151,000 in the presence of a disulfide reducing agent, as estimated by sodium dodecyl sulfate-polyacrylamide gel electrophoresis.

* * * * *